United States Patent [19]

Weidmann et al.

[11] Patent Number: 5,428,046
[45] Date of Patent: Jun. 27, 1995

[54] ACYLSULFONAMIDO- AND SULFONAMIDOPYRIDINE-2-CARBOXYLIC ACID ESTERS AND THEIR PYRIDINE N-OXIDES, PROCESSES FOR THEIR PREPARATION AND THEIR USE AS MEDICAMENTS

[75] Inventors: Klaus Weidmann, Kronberg/Ts; Martin Bickel, Bad Homburg; Volkmar Günzler-Pukall, Marburg; Karl-Heinz Baringhaus, Liederbach, all of Germany

[73] Assignee: Hoechst Aktiengesellschaft, Frankfurt, Germany

[21] Appl. No.: 124,683

[22] Filed: Sep. 22, 1993

[30] Foreign Application Priority Data

Oct. 2, 1992 [DE] Germany .................. 42 33 124.2

[51] Int. Cl.⁶ ............... C07D 213/81; A61K 31/44
[52] U.S. Cl. ..................... 514/356; 514/344; 514/345; 514/352; 546/286; 546/290; 546/299; 546/310; 546/316
[58] Field of Search ............... 546/316, 286, 290, 299, 546/310; 514/356, 344, 345, 352

[56] References Cited

U.S. PATENT DOCUMENTS 5,037,839  8/1991  Bickel .................. 514/354

FOREIGN PATENT DOCUMENTS 3432094  6/1986  Germany .................. 546/314
3703962  8/1988  Germany .................. 546/314
3703963  8/1988  Germany .................. 546/314

OTHER PUBLICATIONS

R. I. Dowell & E. M. Hadley, Journal of Medicinal Chemistry, 35, 800 (1992), entitled "Novel Inhibitors of Prolyl 4–Hydroxylase".

H. Tucker and D. F. Thomas, Journal of Medicinal Chemistry, 35, 804 (1992), entitled "Novel Inhibitors of Prolyl 4–Hydroxylase. 2,5–Amide Substituted Pyridine-2–Carboxylic Acids".

Primary Examiner—C. Warren Ivy
Assistant Examiner—Zinna N. Davis
Attorney, Agent, or Firm—Raymond R. Wittekind

[57] ABSTRACT

Acylsulfonamido-andsulfonamidopyridine-2-carboxylic acid esters and their pyridine N-oxides, processes for their preparation and their use as medicaments.

The invention relates to acylsulfonamido- and sulfonamidopyridine-2-carboxylic acid esters and their pyridine N-oxides of the formula I

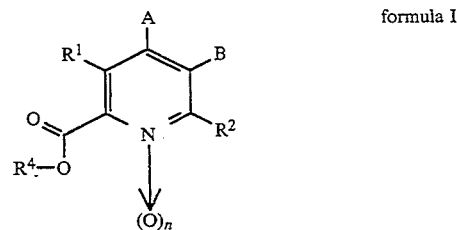

formula I in which

| A = R³ | and | B = X—NR⁵R⁶ or |
| B = R³ | and | A = X—NR⁵R⁶. |

The compounds are suitable as medicaments against fibrotic diseases.

6 Claims, No Drawings

ACYLSULFONAMIDO- AND SULFONAMIDOPYRIDINE-2-CARBOXYLIC ACID ESTERS AND THEIR PYRIDINE N-OXIDES, PROCESSES FOR THEIR PREPARATION AND THEIR USE AS MEDICAMENTS

DESCRIPTION

Acylsulfonamido- and sulfonamidopyridine-2-carboxylic acid esters and their pyridine N-oxides, processes for their preparation and there use as medicaments.

The invention relates to acylsulfonamido- and sulfonamidopyridine-2-carboxylic acid esters and their pyridine N-oxides, and to their use as medicaments against fibrotic diseases.

Compounds which inhibit the enzymes proline hydroxylase and lysine hydroxylase cause very selective inhibition of collagen biosynthesis by influencing collagen-specific hydroxylation reactions. In the course thereof, protein-bound proline or lysine is hydroxylated by the enzymes proline hydroxylase and lysine hydroxylase respectively. If this reaction is suppressed by inhibitors, a hypohydroxylated collagen molecule which is not capable of functioning and can be released by cells into the extracellular space in only a small amount is formed. The hypohydroxylated collagen moreover cannot be incorporated into the collagen matrix and is very readily broken down proteolytically. As a consequence of these effects, the total amount of collagen deposited in the extracellular space is reduced.

Inhibitors of prolyl-hydroxylase are therefore suitable substances in the therapy of diseases where deposition of collagens contributes decisively to the syndrome. These include, inter alia, fibroses of the lungs, liver and skin (sclerodermia) and atherosclerosis.

It is known that the enzyme proline hydroxylase is inhibited effectively by pyridine-2,4-and -2,5-dicarboxylic acid (K. Majamaa et al., Eur. J. Biochem. 138 (1984) 239 to 245). However, these compounds are active as inhibitors in cell cultures only in very high concentrations (Tschank, G. et al., Biochem. J. 238 (1987) 625 to 633).

DE-A 34 32 094 describes pyridine-2,4- and -2,5-dicarboxylic acid diesters having 1 to 6 carbon atoms in the ester alkyl part as medicaments for inhibition of proline hydroxylase and lysine hydroxylase.

However, these lower alkyl diesters have the disadvantage that they are split into the acids too rapidly in the organism and do not arrive at their site of action in the cell in a sufficiently high concentration, and therefore are not particularly suitable for possible administration as medicaments.

DE-A 37 03 959, DE-A 37 03 962 and DE-A 37 03 963 describe, in general form, mixed esters/amides, higher alkyl diesters and diamides of pyridine-2,4- and -2,5-dicarboxylic acid which effectively inhibit collagen biosynthesis in the animal model.

There was thus the object of searching for compounds which have a more potent antifibrotic action than the compounds known to date.

The object is achieved by providing acylsulfonamido- and sulfonamidopyridine-2-carboxylic acid esters and their pyridine N-oxides of the formula I

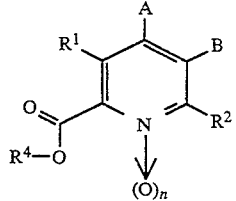

Formula I in which

A=$R^3$ and B=X—$NR^5R^6$ or
B=$R^3$ and A=X—$NR^5R^6$ and
X is a single bond or —CO— and
$R^1$, $R^2$ and $R^3$ are identical or different and are hydrogen, $(C_1-C_6)$-alkyl, $(C_1-C_6)$-alkoxy, halogen, in particular fluorine, chlorine or bromine, nitrile, hydroxyl, amino, optionally mono- or disubstituted by $(C_1-C_4)$-alkyl, hydroxy-$(C_1-C_4)$-alkyl or $(C_1-C_6)$-alkylcarbonyloxy,
$R^4$ is the radical of an alcohol $R^4$OH, in which $R^4$ is, in particular, $(C_1-C_{10})$-acyloxy-$(C_1-C_6)$-alkyl, preferably $(C_1-C_{10})$-alkanoyloxy-$(C_1-C_6)$-alkyl, benzyloxy-$(C_1-C_6)$-alkyl, benzyloxycarbonyloxy-$(C_1-C_6)$-alkyl or alkoxycarbonyloxy-$(C_1-C_6)$-alkyl, a branched or unbranched or cyclic aliphatic $(C_3-C_{16})$-alkyl radical, or a branched or unbranched, optionally cyclic $(C_3-C_{16})$-alkenyl radical, a $(C_2-C_{16})$-alkynyl radical or a $(C_4-C_{16})$-alkenynyl radical, each of which can contain one or more multiple bonds, or a $(C_6-C_{16})$-aryl radical, a $(C_7-C_{16})$-aralkyl radical or a 5- or 6-membered, preferably nitrogen-containing heteroaryl radical or a 5- or 6-membered, preferably nitrogen-containing heteroaralkyl radical, the above radicals carrying, in particular, one or more substituents from the series comprising hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, —$OCF_2Cl$, —$OCF_2$—$CHFCl$, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl,N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-

($C_7$–$C_{16}$)-aralkylcarbamoyl, N-(($C_1$–$C_{10}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkoxy-($C_1$–$C_{10}$)-alkyl)carbamoyl, N-($C_1$–$C_{10}$)-alkyl-N-(($C_6$–$C_{16}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, carbamoyloxy, N-($C_1$–$C_{12}$)-alkylcarbamoyloxy, N,N-di-($C_1$–$C_{12}$)-alkylcarbamoyloxy, N-($C_3$–$C_8$)-cycloalkylcarbamoyloxy, N-($C_6$–$C_{12}$)-arylcarbamoyloxy, N-($C_7$–$C_{16}$)-aralkylcarbamoyloxy, N-($C_1$–$C_{10}$)-alkyl-N-($C_6$–$C_{12}$)-arylcarbamoyloxy, N-($C_1$–$C_{10}$)-alkyl-N-($C_7$–$C_{16}$)-aralkylcarbamoyloxy, N-(($C_1$–$C_{10}$)-alkoxy-($C_1$–$C_{10}$)-alkyl))carbamoyloxy, N-(($C_6$–$C_{16}$)-aryloxy-($C_1$–$C_{10}$)-alkyl)carbamoyloxy, N-(($C_7$–$C_{16}$)-aralkyloxy-($C_1$–$C_{10}$)-alkyl)carbamoyloxy, N-($C_1$–$C_{10}$)-alkyl-N-(($C_1$–$C_{10}$)-alkoxy-($C_1$–$C_{10}$)-alkyl)carbamoyloxy, N-($C_1$–$C_{10}$)-alkyl-N-(($C_6$–$C_{16}$)-aryloxy-($C_1$–$C_{10}$)-alkyl)carbamoyloxy, N-($C_1$–$C_{10}$)-alkyl-N-(($C_7$–$C_{16}$)-aralkyloxy($C_1$–$C_{10}$)-alkyl)carbamoyloxy, amino, ($C_1$–$C_{12}$)-alkylamino, di-($C_1$–$C_{12}$)-alkylamino, ($C_3$–$C_8$)-cycloalkylamino, ($C_3$–$C_{12}$)-alkenylamino, ($C_3$–$C_{12}$)-alkynylamino, N-($C_6$–$C_{12}$)-arylamino, N-($C_7$–$C_{11}$)-aralkylamino, N-alkyl-aralkylamino, N-alkylarylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_6$–$C_{16}$)-aroylamino-($C_1$–$C_8$)-alkyl, ($C_7$–$C_{16}$)-aralkanoylamino-($C_1$–$C_8$)-alkyl, amino-($C_1$–$C_{10}$)-alkyl, N-($C_1$–$C_{10}$)-alkylamino-($C_1$–$C_{10}$)-alkyl, N,N-di-($C_1$–$C_{10}$)-alkylamino-($C_1$–$C_{10}$)-alkyl, ($C_3$–$C_8$)-cycloalkylamino-($C_1$–$C_{10}$)-alkyl, ($C_1$–$C_{12}$)-alkylmercapto, ($C_1$–$C_{12}$)-alkylsulfinyl, ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, sulfamoyl, N-($C_1$–$C_{10}$)-alkylsulfamoyl, N,N-di-($C_1$–$C_{10}$)-alkylsulfamoyl, ($C_3$–$C_8$)-cycloalkylsulfamoyl, N-($C_6$–$C_{16}$)-arylsulfamoyl, N-($C_7$–$C_{16}$)-aralkylsulfamoyl, N-($C_1$–$C_{10}$)-alkyl-N-($C_6$–$C_{16}$)-arylsulfamoyl, N-($C_1$–$C_{10}$)-alkyl-N-($C_7$–$C_{16}$)-aralkylsulfamoyl, ($C_1$–$C_{10}$)-alkyl-sulfonamido, N-(($C_1$–$C_{10}$)-alkyl)-($C_1$–$C_{10}$)-alkylsulfonamido, ($C_7$–$C_{16}$)-aralkylsulfonamido and N-(($C_1$–$C_{10}$)-alkyl-($C_7$–$C_{16}$)-aralkylsulfonamido, it being possible for the radicals which contain an aryl radical to be substituted in turn on the aryl by 1 to 5 identical or different radicals from the series comprising: hydroxyl, halogen, cyano, trifluoromethyl, nitro, carboxyl, ($C_1$–$C_{12}$)-alkyl, ($C_3$–$C_8$)-cycloalkyl, ($C_6$–$C_{12}$)-aryl, ($C_7$–$C_{16}$)-aralkyl, ($C_1$–$C_{12}$)-alkoxy, ($C_1$–$C_{12}$)-alkoxy-($C_1$–$C_{12}$)-alkyl, ($C_1$–$C_{12}$)-alkoxy-($C_1$–$C_{12}$)-alkoxy, ($C_6$–$C_{12}$)-aryloxy, ($C_7$–$C_{16}$)-aralkyloxy, ($C_1$–$C_8$)-hydroxyalkoxy, ($C_1$–$C_{12}$)-alkylcarbonyl, ($C_3$–$C_8$)-cycloalkylcarbonyl, ($C_6$–$C_{12}$)-arylcarbonyl, ($C_7$–$C_{16}$)-aralkylcarbonyl, ($C_1$–$C_{12}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl, ($C_3$–$C_8$)-cycloalkoxycarbonyl, ($C_3$–$C_{12}$)-alkenyloxycarbonyl, ($C_3$–$C_{12}$)-alkynyloxycarbonyl, ($C_1$–$C_{12}$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, cinnamoyloxy, ($C_3$–$C_{12}$)-alkenylcarbonyloxy, ($C_3$–$C_{12}$)-alkynylcarbonyloxy, ($C_1$–$C_{12}$)-alkoxycarbonyloxy, ($C_1$–$C_{12}$)-alkoxy-($C_1$–$C_{12}$)-alkoxycarbonyloxy, ($C_6$–$C_{12}$)-aryloxycarbonyloxy, ($C_7$–$C_{16}$)-aralkyloxycarbonyloxy, ($C_3$–$C_8$)-cycloalkoxycarbonyloxy, ($C_3$–$C_{12}$)-alkenyloxycarbonyloxy, ($C_3$–$C_{12}$)-alkynyloxycarbonyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N-($C_6$–$C_{16}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-(($C_1$–$C_{10}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkoxy-($C_1$–$C_{10}$)-alkyl)carbamoyl, N-($C_1$–$C_{10}$)-alkyl-N-(($C_6$–$C_{16}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, carbamoyloxy, N-($C_1$–$C_{12}$)-alkylcarbamoyloxy, N,N-di-($C_1$–$C_{12}$)-alkylcarbamoyloxy, N-($C_3$–$C_8$)-cycloalkylcarbamoyloxy, N-($C_6$–$C_{16}$)-arylcarbamoyloxy, N-($C_7$–$C_{16}$)-aralkylcarbamoyloxy, N-($C_1$–$C_{10}$)-alkyl-N-($C_6$–$C_{12}$)-arylcarbamoyloxy, N-($C_1$–$C_{10}$)-alkyl-N-($C_7$–$C_{16}$)-aralkylcarbamoyloxy, N-(($C_1$–$C_{10}$)-alkoxy-($C_1$–$C_{10}$)-alkyl)carbamoyloxy, N-(($C_6$–$C_{16}$)-aryloxy-($C_1$–$C_{10}$)-alkyl)carbamoyloxy, N-(($C_7$–$C_{16}$)-aralkyloxy-($C_1$–$C_{10}$)-alkyl)carbamoyloxy, N-($C_1$–$C_{10}$)-alkyl-N-(($C_1$–$C_{10}$)-alkoxy-($C_1$–$C_{10}$)-alkyl)carbamoyloxy, N-($C_1$–$C_{10}$)-alkyl-N-(($C_6$–$C_{16}$)-aryloxy-($C_1$–$C_{10}$)-alkyl)carbamoyloxy, N-($C_1$–$C_{10}$)-alkyl-N-(($C_7$–$C_{16}$)-aralkyloxy-($C_1$–$C_{10}$)-alkyl)carbamoyloxy, amino, ($C_1$–$C_{12}$)-alkylamino, di-($C_1$–$C_{12}$)-alkylamino, ($C_3$–$C_8$)-cycloalkylamino, ($C_3$–$C_{12}$)-alkenylamino, ($C_3$–$C_{12}$)-alkynylamino, N-($C_6$–$C_{12}$)-arylamino, N-($C_7$–$C_{11}$)-aralkylamino, N-alkyl-aralkylamino, N-alkylarylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_6$–$C_{16}$)-aroylamino-($C_1$–$C_8$)-alkyl, ($C_7$–$C_{16}$)-aralkanoylamino-($C_1$–$C_8$)-alkyl, amino-($C_1$–$C_{10}$)-alkyl, N-($C_1$–$C_{10}$)-alkylamino-($C_1$–$C_{10}$)-alkyl, N,N-di-($C_1$–$C_{10}$)-alkylamino-($C_1$–$C_{10}$)-alkyl, ($C_3$–$C_8$)-cycloalkylamino-($C_1$–$C_{10}$)-alkyl, ($C_1$–$C_{12}$)-alkylmercapto, ($C_1$–$C_{12}$)-alkylsulfinyl ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-aralkylmercapto, ($C_7$–$C_{16}$)-aralkylsulfinyl and ($C_7$–$C_{16}$)-aralkylsulfonyl, $R^5$ is hydrogen, ($C_1$–$C_6$)-alkyl or an N-protective group, such as ($C_1$–$C_8$)-alkanoyl, ($C_1$–$C_6$)-alkylcarbamoyl, ($C_1$–$C_6$)-alkoxycarbonyl, benzyloxycarbonyl, ($C_1$–$C_{10}$)-acyloxy-($C_1$–$C_6$)-alkyl, preferably ($C_1$–$C_{10}$)-alkanoyloxy-($C_1$–$C_6$)-alkyl, benzoyloxy-($C_1$–$C_6$)-alkyl, benzyloxycarbonyloxy-($C_1$–$C_6$)- alkyl or $(C_1-C_6)$-alkoxycarbonyloxy-$(C_1-C_6)$-alkyl, a mono-, di-, tri- or tetravalent physiologically usable cation, in particular $Na^\oplus$, $K^\oplus$, $Mg^{2\oplus}$, $Ca^{2\oplus}$, $Al^{3\oplus}$ or an ammonium ion mono-, di- or trisubstituted by $(C_1-C_8)$-hydroxyalkyl, $(C_1-C_4)$-alkoxy-$(C_1-C_8)$-alkyl, phenyl, benzyl or $(C_1-C_8)$-alkyl, which can be mono-, di- or trisubstituted by hydroxyl or $(C_1-C_4)$-alkoxy, or a cation of a basic amino acid derivative, $R^6$ is a radical of the formula II, excluding —SO$_2$H $$-Y-[C-U]_r-D-W \qquad (II)$$

in which

Y is —SO$_2$— or —CO—,

C is a bond or a branched or unbranched aliphatic $(C_1-C_{16})$-alkanediyl or cycloaliphatic $(C_3-C_{10})$-alkanediyl radical or a branched or unbranched $(C_2-C_{16})$-alkenediyl or cycloalkenediyl radical, or a $(C_2-C_{16})$-alkinediyl radical or a $(C_2-C_{16})$-alkeninediyl radical, each of which can contain one or more C—C multiple bonds, U is a bond or hydrogen or a radical from the following series of hetero atom groupings —CO—, —O(CO)—, —(CO)—O—, —(CO)NR—, —NR(CO)—, —O—, —SO—, —SO$_2$— and —NR, in which R is $(C_1-C_3)$-alkyl or hydrogen, r is 1, 2, 3 or 4, D is a bond or hydrogen or a branched or unbranched aliphatic $(C_1-C_{10})$-alkanediyl radical, or a branched or unbranched $(C_1-C_{10})$-alkenediyl radical, a $(C_2-C_{10})$-alkinediyl radical or a $(C_2-C_{10})$-alkeninediyl radical, each of which can contain one or more C—C multiple bonds, W is a bond or hydrogen or a $(C_3-C_{10})$ cycloaliphatic alkyl, alkenyl, alkynyl or alkenynyl radical or a $(C_6-C_{16})$-aryl radical or a 5- or 6-membered heteroaryl radical, in which at least one of the variables C or D or W is not a bond and U only denotes a hetero atom grouping if C is not a bond or if D and/or W are not a bond and C, D and/or W, if these are not a bond or hydrogen, are preferably substituted in turn by a combination of up to 5 identical or different substituents from the series comprising hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—[CH$_2$]$_x$C$_f$H$_{(2f+1-g)}$F$_g$, —OCF$_2$Cl, —OCF$_2$—CHFCl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$-arylcarbamoyloxy, N-$(C_1-C_{10})$-alkyl-N-$(C_7-C_{16})$-aralkylcarbamoyloxy, N-$((C_1-C_{10})$-alkoxy-$(C_1-C_{10})$-alkyl)carbamoyloxy, N-$((C_6-C_{16})$-aryloxy-$(C_1-C_{10})$-alkyl)carbamoyloxy, N-$((C_7-C_{16})$-aralkyloxy-$(C_1-C_{10})$-alkyl)carbamoyloxy, N-$(C_1-C_{10})$-alkyl-N-$((C_1-C_{10})$-alkoxy-$(C_1-C_{10})$-alkyl)carbamoyloxy, N-$(C_1-C_{10})$-alkyl-N-$((C_6-C_{16})$-aryloxy-$(C_1-C_{10})$-alkyl)carbamoyloxy, N-$(C_1-C_{10})$-alkyl-N-$((C_7-C_{16})$-aralkyloxy$(C_1-C_{10})$-alkyl)carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-$(C_1-C_{10})$-alkyl-$(C_7-C_{10})$-aralkylamino, N-$(C_1-C_{10})$-alkyl-N-$(C_6-C_{12})$-arylamino, $(C_1-C_{12})$-alkoxyamino, $(C_1-C_{12})$-alkoxy-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N-$(C_1-C_{10})$-alkylsulfamoyl, N,N-di-$(C_1-C_{10})$-alkylsulfamoyl, $(C_3-C_8)$-cycloalkylsulfamoyl, N-$(C_6-C_{16})$-arylsulfamoyl, N-$(C_7-C_{16})$-aralkylsulfamoyl, N-$(C_1-C_{10})$-alkyl-N-$(C_6-C_{16})$-arylsulfamoyl, N-$(C_1-C_{10})$-alkyl-N-$(C_7-C_{16})$-aralkylsulfamoyl, $(C_1-C_{10})$-alkyl-sulfonamido, N-$((C_1-C_{10})$-alkyl)-$(C_1-C_{10})$-alkylsulfonamido, $(C_7-C_{16})$-aralkylsulfonamido and N-$((C_1-C_{10})$-alkyl-$(C_7-C_{16})$-aralkylsulfonamido, it being possible for the radicals which contain an aryl radical to be substituted in turn on the aryl by 1,2,3,4 or 5 identical or different substituents from the series comprising: hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, —$OCF_2Cl$, —$OCF_2$—$CHFCl$, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$-arylcarbamoyloxy, N-$(C_1-C_{10})$-alkyl-N-$(C_7-C_{16})$-aralkylcarbamoyloxy, N-$((C_1-C_{10})$-alkoxy-$(C_1-C_{10})$-alkyl))carbamoyloxy, N-$((C_6-C_{16})$-aryloxy-$(C_1-C_{10})$-alkyl)carbamoyloxy, N-$((C_7-C_{16})$-aralkyloxy-$(C_1-C_{10})$-alkyl)carbamoyloxy, N-$(C_1-C_{10})$-alkyl-N-$((C_1-C_{10})$-alkoxy-$(C_1-C_{10})$-alkyl)carbamoyloxy, N-$(C_1-C_{10})$-alkyl-N-$((C_6-C_{16})$-aryloxy-$(C_1-C_{10})$-alkyl)carbamoyloxy, N-$(C_1-C_{10})$-alkyl-N-$((C_7-C_{16})$-aralkyloxy$(C_1-C_{10})$-alkyl)carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-$(C_1-C_{10})$-alkyl-N-$(C_7-C_{16})$-aralkylamino, N-$(C_1-C_{10})$-alkyl-N-$(C_6-C_{12})$-arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{16})$-aroylamino$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N-$(C_1-C_{10})$-alkylsulfamoyl, N,N-di-$(C_1-C_{10})$-alkylsulfamoyl, $(C_3-C_8)$-cycloalkylsulfamoyl, N-$(C_6-C_{16})$-arylsulfamoyl, N-$(C_7-C_{16})$-aralkylsulfamoyl, N-$(C_1-C_{10})$-alkyl-N-$(C_6-C_{16})$-arylsulfamoyl, N-$(C_1-C_{10})$-alkyl-N-$(C_7-C_{16})$-aralkylsulfamoyl, $(C_1-C_{10})$-alkyl-sulfonamido, N-$((C_1-C_{10})$-alkyl)-$(C_1-C_{10})$-alkylsulfonamido, $(C_7-C_{16})$-aralkylsulfonamido and N-$((C_1-C_{10})$-alkyl-$(C_7-C_{16})$-aralkylsulfonamido, and n is 0 or 1, f is 1 to 8, preferably 1 to 5, g is 0 or 1 to (2f+1) and x is 0 to 8, preferably 0 or 1, excluding methyl 5-[((methylsulfonyl)amino)carbonyl]-pyridine-2-carboxylate, methyl 5-[((2-propylsulfonyl)amino)carbonyl]-pyridine-2-carboxylate, methyl 5-[((phenylsulfonyl)amino)carbonyl]-pyridine-2-carboxylate, methyl 5-[((benzylsulfonyl)amino)carbonyl]-pyridine-2-carboxylate, methyl 5-[((4-methoxyphenylsulfonyl)amino)carbonyl]-pyridine-2-carboxylate, methyl 5-[((1-naphthylsulfonyl)amino)carbonyl]-pyridine-2-carboxylate, methyl 5-[((4,5-dibromo-2-thienylsulfonyl)aminocarbonyl]-pyridine-2-carboxylate, methyl 5-[((5-chloro-2-thienylsulfonyl)amino)carbonyl]-pyridine-2-carboxylate, methyl 5-[((8-quinolylsulfonyl)amino)carbonyl]-pyridine-2-carboxylate, methyl 5-[((4-(2-(4,7-dichloroquinolyl)phenyl-sulfonyl)amino)carbonyl]-pyridine-2-carboxylate.

Aryl, aryloxy, heteroaryl and heteroaryloxy compounds are to be understood as meaning, in particular, phenyl, biphenyl or naphthyl rings or unsubstituted 5- or 6-membered heteroaromatic rings having 1, 2 or 3 nitrogen and/or oxygen and/or sulfur atoms, such as pyridyl, pyridazyl, pyrimidyl, pyrazyl, imidazolyl, triazolyl, thienyl, oxazolyl and thiazolyl derivatives, and benzo-fused derivatives thereof.

Preferred compounds of the formula I are those in which

X is a single bond or —CO—, $R^1$, $R^2$ and $R^3$ are identical or different and are hydrogen, $(C_1-C_6)$-alkyl, $(C_1-C_6)$-alkoxy, halogen, in particular fluorine or chlorine, hydroxyl or amino, $R^4$ is a radical of an alcohol $R^4OH$, in which $R^4$ is $(C_1-C_{10})$-acyloxy-$(C_1-C_6)$-alkyl, preferably $(C_1-C_{10})$-alkanoyloxy-$(C_1-C_6)$-alkyl, benzoyloxy-$(C_1-C_6)$-alkyl, benzyloxycarbonyloxy-$(C_1-C_6)$-alkyl or $(C_1-C_6)$-alkoxycarbonyloxy-$(C_1-C_6)$-alkyl, a branched or unbranched aliphatic or cycloaliphatic $(C_3-C_{12})$-alkyl radical, a branched or unbranched cyclic $(C_3-C_{12})$-alkenyl radical, a $(C_2-C_{12})$-alkynyl radical or a $(C_4-C_{12})$-alkenynyl radical, each of which can contain one or more multiple bonds, or a $(C_6-C_{16})$-aryl radical, a $(C_6-C_{16})$-aralkyl radical or a heteroaryl or a heteroaralkyl radical, it being possible for the above radicals to carry one or two substituents from the series comprising hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-aryloxy, $(C_7-C_{16})$-aralkyloxy, $(C_1-C_8)$-hydroxyalkyl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$-arylcarbamoyloxy, N-$(C_1-C_{10})$-alkyl-N-$(C_7-C_{16})$-aralkylcarbamoyloxy, N-$((C_1-C_{10})$-alkoxy-$(C_1-C_{10})$-alkyl)carbamoyloxy, N-$((C_6-C_{16})$-aryloxy-$(C_1-C_{10})$-alkyl)carbamoyloxy, N-$((C_7-C_{16})$-aralkyloxy-$(C_1-C_{10})$-alkyl)carbamoyloxy, N-$(C_1-C_{10})$-alkyl-N-$((C_1-C_{10})$-alkoxy-$(C_1-C_{10})$-alkyl)carbamoyloxy, N-$(C_1-C_{10})$-alkyl-N-$((C_6-C_{16})$-aryloxy-$(C_1-C_{10})$-alkyl)carbamoyloxy, N-$(C_1-C_{10})$-alkyl-N-$((C_7-C_{16})$-aralkyloxy-$(C_1-C_{10})$-alkyl)carbamoyloxy, amino, $(C_1-C_{12})$-alkylamino, di-$(C_1-C_{12})$-alkylamino, $(C_3-C_8)$-cycloalkylamino, N-$(C_7-C_{11})$-aralkylamino, N-alkyl-arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino and $(C_7-C_{11})$-aralkanoyl-N-$(C_1-C_{10})$-alkylamino, and it being possible for the radicals which contain an aryl radical to be substituted in turn in the aryl part by 1 to 5 identical or different radicals from the series comprising hydroxyl, halogen, cyano, trifluoromethyl, $(C_1-C_{12})$-alkyl, $(C_3-C_8)$-cycloalkyl, $(C_1-C_{12})$-alkoxy, $(C_1-C_{12})$-alkoxy-$(C_1-C_{12})$-alkoxy, $(C_1-C_{12})$-alkylcarbonyl, $(C_3-C_8)$-cycloalkylcarbonyl, $(C_1-C_{12})$-alkoxycarbonyl, $(C_1-C_{12})$-alkoxy-$(C_1-C_{12})$-alkoxycarbonyl, $(C_3-C_8)$-cycloalkoxycarbonyl, $(C_1-C_{12})$-alkylcarbonyloxy, $(C_3-C_8)$-cycloalkylcarbonyloxy, $(C_1-C_{12})$-alkoxycarbonyloxy, $(C_1-C_{12})$-alkoxy-$(C_1-C_{12})$-alkoxycarbonyloxy, $(C_3-C_8)$-cycloalkoxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$((C_1-C_{10})$-alkoxy-$(C_1-C_{10})$-alkyl)carbamoyl, N-$(C_1-C_{10})$-alkyl-N-$((C_1-C_{10})$-alkoxy-$(C_1-C_{10})$-alkyl)-carbamoyl, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, amino, $(C_1-C_{12})$-alkylamino, di-$(C_1-C_{12})$-alkylamino, $(C_3-C_8)$-cycloalkylamino, $(C_1-C_{12})$-alkanoylamino, $(C_3-C_8)$-cycloalkanoylamino, $(C_1-C_{12})$-alkanoylamino-$(C_1-C_8)$-alkyl, $(C_3-C_8)$-cycloalkanoylamino-$(C_1-C_8)$-alkyl, $(C_1-C_{12})$-alkylmercapto, $(C_1-C_{12})$-alkylsulfinyl and $(C_1-C_{12})$-alkylsulfonyl, $R^5$ is hydrogen, $(C_1-C_3)$-alkyl, $(C_1-C_4)$-alkanoyl or a mono-, di- or trivalent physiologically usable cation, in particular Na$^\oplus$, K$^\oplus$, Mg$^{2\oplus}$, Ca$^{2\oplus}$ or an ammonium ion, optionally mono-, di- or trisubstituted by $(C_1-C_8)$-hydroxyalkyl, $(C_1-C_4)$-alkoxy-$(C_1-C_8)$-alkyl, phenyl, benzyl or $(C_1-C_8)$-alkyl, which can be mono-, di- or trisubstituted by hydroxyl and/or $(C_1-C_4)$-alkoxy, or a cation of a basic amino acid derivative, $R^6$ is a radical of the formula II, excluding —SO$_2$H $$-Y-[C-U]_r-D-W \qquad (II)$$

in which

Y is —SO$_2$—,

C is a bond or a branched or unbranched aliphatic $(C_1-C_{12})$-alkanediyl radical or a branched or unbranched $(C_2-C_{12})$-alkenediyl radical, a $(C_2-C_{12})$-alkinediyl radical or a $(C_2-C_{12})$-alkeninediyl radical, which can contain one or more C—C multiple bonds, U is a bond or hydrogen or a radical from the following series of heteroatom groupings —(CO)NR—, —NR(CO)—, —O—, —SO— or —SO$_2$—, in which R is $(C_2-C_3)$-alkyl or hydrogen, r is 1 or 2, D is a bond or hydrogen or a branched or unbranched aliphatic $(C_1-C_8)$-alkanediyl radical, or a branched or unbranched $(C_2-C_8)$-alkenediyl radical, or a $(C_2-C_8)$-alkinediyl radical and W is a bond or hydrogen or a $(C_3-C_{10})$ cycloaliphatic alkyl, alkenyl, alkynyl or alkenynyl radical or a $(C_6-C_{16})$-aryl radical or a 5- or 6-membered heteroaryl radical, at least one of the variables C or D or W not being a bond and U only being a heteroatom grouping if C is not a bond or if D and/or W are not a bond and C, D and/or W, if these are not a bond or hydrogen, are preferably substituted in turn by a combination of up to 5 identical or different substituents from the series comprising hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, —OCF$_2$Cl, —OCF$_2$—CHFCl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-$(C_1-C_5)$-alkyl-N-$(C_7-C_{10})$-aralkylamino, N-$(C_1-C_5)$-alkyl-N-$(C_6-C_{12})$-arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$arylsulfonyl, $(C_7-C_{16})$-aralkylmercapto, $(C_7-C_{16})$-aralkylsulfinyl and $(C_7-C_{16})$-aralkylsulfonyl, excluding the compounds:

methyl 5-[((methylsulfonyl)amino)carbonyl]-pyridine-2-carboxylate, methyl 5-[((2-propylsulfonyl)amino)carbonyl]-pyridine-2-carboxylate, methyl 5-[((phenylsulfonyl)amino)carbonyl]-pyridine-2-carboxylate, methyl 5-[((benzylsulfonyl)amino)carbonyl]-pyridine-2-carboxylate, methyl 5-[((4-methoxyphenylsulfonyl)amino)carbonyl]-pyridine-2-carboxylate,
methyl 5-[((1-naphthylsulfonyl)amino)carbonyl]-pyridine-2-carboxylate,
methyl 5-[((4,5-dibromo-2-thienylsulfonyl)amino)carbonyl]-pyridine-2-carboxylate,
methyl 5-[((5-chloro-2-thienylsulfonyl)amino)carbonyl]-pyridine-2-carboxylate,
methyl 5-[((8-quinolylsulfonyl)amino)carbonyl]-pyridine-2-carboxylate and
methyl 5-[((4-(2-(4,7-dichloroquinolyl)phenylsulfonyl)amino)carbonyl]-pyridine-2-carboxylate.

Particularly preferred compounds of the formula I are those in which

X is a single bond or —CO—, $R^1$, $R^2$ and $R^3$ are identical or different and are hydrogen or $(C_1-C_3)$-alkyl, $(C_1-C_3)$-alkoxy, hydroxyl, fluorine or chlorine, $R^4$ is the radical of an alcohol $R^4OH$, in which $R^4$ is $(C_1-C_{10})$-acyloxy-$(C_1-C_6)$-alkyl, preferably $(C_1-C_{10})$-alkanoyloxy-$(C_1-C_6)$-alkyl, benzoyloxy-$(C_1-C_6)$-alkyl, benzyloxycarbonyloxy-$(C_1-C_6)$-alkyl or $(C_1-C_6)$-alkoxycarbonyloxy-$(C_1-C_6)$-alkyl, a branched or unbranched or cyclic aliphatic $(C_3-C_{10})$-alkyl radical, or a branched or unbranched cyclic $(C_3-C_{10})$-alkenyl radical or a $(C_2-C_{12})$-alkynyl radical, each of which can contain one or more C—C multiple bonds, or a $(C_6-C_{16})$-aryl radical, a $(C_7-C_{11})$-aralkyl radical or a heteroaryl or heteroalkyl radical, it being possible for the above radicals to carry one or two substituents from the series comprising hydroxyl, $(C_1-C_6)$-alkoxy, $(C_1-C_6)$-alkoxy-$(C_1-C_6)$-alkoxy, $(C_6-C_{12})$-aryloxy, $(C_7-C_{12})$-aralkyloxy, $(C_1-C_8)$-alkylcarbonyl, $(C_3-C_8)$-cycloalkylcarbonyl, $(C_6-C_{12})$-arylcarbonyl, $(C_7-C_{12})$-aralkylcarbonyl, $(C_1-C_8)$-alkoxycarbonyl, $(C_1-C_6)$-alkoxy-$(C_1-C_6)$-alkoxycarbonyl, $(C_6-C_{12})$-aryloxycarbonyl, $(C_7-C_{12})$-aralkoxycarbonyl, $(C_3-C_8)$-cycloalkoxycarbonyl, $(C_1-C_8)$-alkylcarbonyloxy, $(C_3-C_8)$-cycloakylcarbonyloxy, $(C_6-C_{12})$-arylcarbonyloxy, $(C_7-C_{12})$-aralkylcarbonyloxy, $(C_1-C_8)$-alkoxycarbonyloxy, $(C_1-C_6)$-alkoxy-$(C_1-C_6)$-alkoxycarbonyloxy, $(C_6-C_{12})$-aryloxycarbonyloxy, $(C_7-C_{12})$-aralkyloxycarbonyloxy, $(C_3-C_8)$-cycloalkoxycarbonyloxy, carbamoyl, N-$(C_1-C_6)$-alkylcarbamoyl, N,N-di-$(C_1-C_8)$-alkylcarbamoyl, N,N-di-$(C_1-C_8)$-alkylcarbamoyl, N-$(C_3-C_8)$-cycloalkylcarbamoyl, N-$((C_1-C_6)$-alkoxy-$(C_1-C_6)$-alkyl)carbamoyl, amino, $(C_1-C_6)$-alkylamino, di-$(C_1-C_6)$-alkylamino, $(C_3-C_8)$-cycloalkyamino, N-$(C_6-C_{12})$-arylamino, N-$(C_7-C_{11})$-aralkylamino, N-$(C_1-C_5)$-alkyl-$(C_6-C_{12})$-arylamino, $(C_1-C_8)$-alkanoylamino, $(C_3-C_8)$-cycloalkanoylamino, $(C_6-C_{12})$-aroylamino, $(C_7-C_{12})$-aralkanoylamino, $(C_1-C_8)$-alkanoyl-N-$(C_1-C_6)$-alkylamino, $(C_3-C_8)$-cycloakanoyl-N-$(C_1-C_6)$-alkylamino, $(C_6-C_{12})$-aroyl-N-$(C_1-C_6)$-alkylamino and $(C_7-C_{11})$-aralkanoyl-N-$(C_1-C_6)$-alkylamino, and the radicals which contain an aryl radical being substituted, in particular, by up to 3 substituents from the series comprising hydroxyl, fluorine, chlorine, cyano, trifluoromethyl, $(C_1-C_6)$-alkyl, $(C_3-C_8)$-cycloalkyl, $(C_1-C_8)$-alkoxy, $(C_1-C_6)$-alkylcarbonyl, $(C_3-C_8)$-cycloalkylcarbonyl, $(C_1-C_6)$-alkoxycarbonyl, $(C_3-C_8)$-cycloalkoxycarbonyl, $(C_1-C_6)$-alkylcarbonyloxy, $(C_3-C_8)$-cycloalkylcarbonyloxy, $(C_1-C_6)$-alkoxycarbonyloxy, $(C_3-C_8)$-cycloalkoxycarbamoyloxy, carbamoyl, N-$(C_1-C_6)$-alkylcarbamoyl, N,N-di-$(C_1-C_6)$-alkylcarbamoyl, N-$(C_3-C_8)$-cycloalkylcarbamoyl, N-$((C_1-C_6)$-alkoxy-$(C_1-C_6)$-alkyl)carbamoyl, N-$(C_1-C_6)$-alkyl-N-$((C_1-C_6)$-alkoxy-$(C_1-C_6)$-alkyl)carbamoyl, carbamoyloxy, N-$(C_1-C_6)$-alkylcarbamoyloxy, N,N-di-$(C_1-C_6)$-alkylcarbamoyloxy, N-$(C_3-C_8)$-cycloalkylcarbamoyloxy, amino, $(C_1-C_6)$-alkylamino, di-$(C_1-C_6)$-alkylamino, $(C_3-C_8)$-cycloalkylamino, $(C_1-C_6)$-alkanoylamino, $(C_3-C_8)$-cycloalkanoylamino, $(C_1-C_6)$-alkylmercapto, $(C_1-C_6)$-alkylsulfinyl and $(C_1-C_6)$-alkylsulfonyl,
and $R^5$ is hydrogen, $(C_1-C_3)$-alkyl, $(C_1-C_4)$-alkanoyl or a mono-, di- or trivalent physiologically usable cation, in particular $Na^\oplus$, $K^\oplus$, $Mg^{2\oplus}$, $Ca^{2\oplus}$ or an ammonium ion, optionally mono-, di- or trisubstituted by $(C_1-C_8)$-hydroxyalkyl, $(C_1-C_4)$-alkoxy-$(C_1-C_8)$-alkyl, phenyl, benzyl or $(C_1-C_8)$-alkyl, which can be mono-, di- or trisubstituted by hydroxyl and/or $(C_1-C_4)$-alkoxy, $R^6$ is a radical of the formula II, excluding —$SO_2H$ $$—Y—[C—U]_r—D—W \qquad (II)$$

in which

Y is —$SO_2$—,

C is a bond or a $(C_1-C_{16})$-alkanediyl radical,

U is a bond or hydrogen or —O—, r is 1,

D is a bond or hydrogen or an unbranched aliphatic $(C_1-C_8)$-alkanediyl radical, and W is a bond or hydrogen, a $(C_6-C_{12})$-aryl radical or a 5- or 6-membered heteroaryl radical, at least one of the variables C or D or W not being a bond and U only being a hetero atom grouping if C is not bond or if D and/or W are not a bond and C, D and/or W, if these are not a bond or hydrogen, are preferably substituted in turn by up to 3 identical or different substituents from the series comprising hydroxyl, halogen, cyano, trifluoromethyl, nitro, carboxyl, $(C_1-C_8)$-alkyl, $(C_3-C_8)$-cycloalkyl, $(C_6-C_{12})$-aryl, $(C_7-C_{16})$-aralkyl, $(C_3-C_8)$-alkenyl, $(C_3-C_8)$-alkynyl, $(C_1-C_8)$-alkoxy, $(C_1-C_8)$-alkoxy-$(C_1-C_8)$-alkyl, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, $(C_1-C_8)$-alkoxycarbonyl, $(C_6-C_{12})$-aryloxycarbonyl, $(C_7-C_{14})$-aralkoxycarbonyl, $(C_3-C_8)$-cycloalkoxycarbonyl, $(C_1-C_8)$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, amino, $(C_1-C_8)$-alkylamino, di-$(C_1-C_8)$-alkylamino, $(C_3-C_8)$- cycloalkylamino, N-($C_6$-$C_{12}$)-arylamino, N-($C_7$-$C_{11}$)-aralkylamino, N-($C_1$-$C_3$)-alkyl-N-($C_7$-$C_{11}$)-aralkylamino, ($C_1$-$C_{10}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{10}$)-alkanoyl-N-($C_1$-$C_{10}$)-alkylamino, ($C_3$-$C_8$)-cycloalkanoyl-N-($C_1$-$C_{10}$)-alkylamino, ($C_6$-$C_{12}$)-aroyl-N-($C_1$-$C_{10}$)-alkylamino, ($C_7$-$C_{11}$)-aralkanoyl-N-($C_1$-$C_{10}$)-alkylamino, ($C_1$-$C_{12}$)-alkanoylamino-($C_1$-$C_6$)-alkyl, ($C_3$-$C_8$)-cycloalkanoylamino-($C_1$-$C_8$)-alkyl, ($C_6$-$C_{16}$)-aroylamino-($C_1$-$C_6$)-alkyl, ($C_7$-$C_{16}$)-aralkanoylamino-($C_1$-$C_6$)-alkyl, ($C_1$-$C_8$)-alkylmercapto, ($C_1$-$C_8$)-alkylsulfinyl, ($C_1$-$C_8$)-alkylsulfonyl, ($C_6$-$C_{12}$)-arylmercapto, ($C_6$-$C_{12}$)-arylsulfinyl, ($C_6$-$C_{12}$)-arylsulfonyl, ($C_7$-$C_{14}$)-aralkylmercapto, ($C_7$-$C_{14}$)-aralkylsulfinyl and ($C_7$-$C_{14}$)-aralkylsulfonyl, is being possible for the radicals which contain an aryl radical to be substituted in turn on the aryl by 1, 2, 3, 4 or 5 identical or different substituents from the series comprising hydrogen, hydroxyl, halogen, cyano, trifluoromethyl, nitro, carboxyl, ($C_1$-$C_8$)-alkyl, ($C_3$-$C_8$)-cycloalkyl, ($C_6$-$C_{12}$)-aryl, ($C_7$-$C_{16}$)-aralkyl, ($C_3$-$C_{12}$)-alkenyl, ($C_3$-$C_{12}$)-alkynyl, ($C_1$-$C_8$)-alkoxy, ($C_1$-$C_6$)-alkoxy-($C_1$-$C_6$)-alkyl, ($C_6$-$C_{12}$)-aryloxy, ($C_7$-$C_{16}$)-aralkyloxy, —O—$[CH_2]_x C_f H_{(2f+1-g)} F_g$, ($C_1$-$C_{12}$)-alkoxycarbonyl, ($C_3$-$C_8$)-cycloalkoxycarbonyl, ($C_1$-$C_{12}$)-alkylcarbonyloxy, ($C_3$-$C_8$)-cycloalkylcarbonyloxy, carbamoyl, N-($C_1$-$C_8$)-alkylcarbamoyl, N,N-di-($C_1$-$C_8$)-alkylcarbamoyl, N-($C_3$-$C_8$)-cycloalkylcarbamoyl, N-($C_6$-$C_{16}$)-arylcarbamoyl, N-($C_7$-$C_{16}$)-aralkylcarbamoyl, N-($C_1$-$C_8$)-alkyl-N-($C_6$-$C_{16}$)-arylcarbamoyl, N-($C_1$-$C_8$)-alkyl-N-($C_7$-$C_{16}$)-aralkylcabamoyl, N-(($C_1$-$C_6$)-alkoxy-($C_1$-$C_6$)-alkyl)carbamoyl, N-(($C_6$-$C_{16}$)-aryloxy-($C_1$-$C_6$)-alkyl)carbamoyl, N-(($C_7$-$C_{16}$)-aralkyloxy-($C_1$-$C_6$)-alkyl)carbamoyl, N-($C_1$-$C_8$)-alkyl-N-(($C_1$-$C_6$)-alkoxy-($C_1$-$C_6$)-alkyl)carbamoyl, N-($C_1$-$C_8$)-alkyl-N-(($C_6$-$C_{16}$)-aryloxy-($C_1$-$C_6$)-alkyl)carbamoyl, N-($C_1$-$C_8$)-alkyl-N-(($C_7$-$C_{16}$)-aralkyloxy-($C_1$-$C_6$)-alkyl)carbamoyl, amino, ($C_1$-$C_6$)-alkylamino, di-($C_1$-$C_6$)-alkylamino, ($C_3$-$C_8$)-cycloalkylamino, N-($C_6$-$C_{12}$)-arylamino, N-($C_7$-$C_{11}$)-aralkylamino, N-($C_1$-$C_3$)-alkyl-($C_7$-$C_{11}$)-aralkylamino, N-($C_1$-$C_3$)-alkyl-($C_6$-$C_{12}$)-arylamino, ($C_1$-$C_8$)-alkoxy-amino, ($C_1$-$C_8$)-alkanoylamino, ($C_3$-$C_8$)-cycloalkanoylamino, ($C_6$-$C_{12}$)-aroylamino, ($C_7$-$C_{12}$)-aralkanoylamino, ($C_1$-$C_8$)-alkanoyl-N-($C_1$-$C_6$)-alkylamino, ($C_3$-$C_8$)-cycloalkanoyl-N-($C_1$-$C_6$)-alkylamino, ($C_6$-$C_{12}$)-aroyl-N-($C_1$-$C_{10}$)-alkylamino, ($C_7$-$C_{11}$)-aralkanoyl-N-($C_1$-$C_6$)-alkylamino, ($C_1$-$C_8$)-alkanoylamino-($C_1$-$C_4$)-alkyl, ($C_3$-$C_8$)-cycloalkanoylamino-($C_1$-$C_4$)-alkyl, ($C_6$-$C_{12}$)-aroylamino-($C_1$-$C_4$)-alkyl and ($C_7$-$C_{12}$)-aralkanoylamino-($C_1$-$C_4$)-alkyl,
excluding the compounds:
methyl 5-[((methylsulfonyl)amino)carbonyl]-pyridine-2-carboxylate,
methyl 5-[((2-propylsulfonyl)amino)carbonyl]-pyridine-2-carboxylate,
methyl 5-[((phenylsulfonyl)amino)carbonyl]-pyridine-2-carboxylate,
methyl 5-[((benzylsulfonyl)amino)carbonyl]-pyridine-2-carboxylate,
methyl 5-[((4-methoxyphenylsulfonyl)amino)carbonyl]-pyridine-2-carboxylate,
methyl 5-[((1-naphthylsulfonyl)amino)carbonyl]-pyridine-2-carboxylate
methyl 5-[((4,5-dibromo-2-thienylsulfonyl)amino)carbonyl]-pyridine-2-carboxylate,
methyl 5-[((5-chloro-2-thienylsulfonyl)amino)carbonyl]-pyridine-2-carboxylate,
methyl 5-[((8-quinolylsulfonyl)amino)carbonyl]-pyridine-2-carboxylate,
methyl 5-[((4-(2-(4,7-dichloroquinolyl))phenylsulfonyl)amino)carbonyl]-pyridine-2-carboxylate.

Especially preferred compounds of the formula I are those in which

X is a single bond or —CO—, $R^1$, $R^2$ and $R^3$ are hydrogen, $R^4$ is the radical of an alcohol $R^4OH$ and is a branched or unbranched or cyclic aliphatic ($C_3$-$C_9$)-alkyl radical, or a branched or unbranched cyclic ($C_3$-$C_8$)-alkenyl radical or ($C_2$-$C_8$)-alkynyl radical, or a phenyl, benzyl, phenethyl or phenylpropyl radical, the above radicals containing a substituent from the series comprising hydrogen, hydroxyl, ($C_1$-$C_4$)-alkoxy, ($C_1$-$C_6$)-alkoxycarbonyl, ($C_6$-$C_{12}$)-phenoxycarbonyl, ($C_7$-$C_{16}$)-phenylalkylcarbonyl, ($C_3$-$C_8$)-cycloalkoxycarbonyl, ($C_1$-$C_6$)-alkylcarbonyloxy, ($C_3$-$C_8$)-cycloalkylcarbonyloxy, benzoyloxy, ($C_7$-$C_{16}$)-phenylalkylcarbonyloxy and ($C_3$-$C_8$)-cycloalkoxycarbonyloxy, or ($C_1$-$C_6$)-alkoxycarbonyloxy, phenoxycarbonyloxy, ($C_7$-$C_{16}$)-phenylalkylcarbonyloxy or ($C_3$-$C_8$)-cycloalkoxycarbonyloxy, $R^5$ is hydrogen or a mono-, di- or trivalent physiologically usable cation, in particular $Na^{\oplus}$, $K^{\oplus}$, $Mg^{2\oplus}$, $Ca^{2\oplus}$ or $H_3N^{\oplus}C(CH_2OH)_3$ (tris salt), $R^6$ is a radical of the formula II, excluding —$SO_2H$ $$-Y-[C-U]_r-D-W \qquad (II)$$

in which

Y is —$SO_2$—,

C is a bond or ($C_1$-$C_4$)-alkanediyl,

U is a bond, hydrogen or —O—, r is 1,

D is a bond, hydrogen or ($C_1$-$C_4$)-alkanediyl,

W is a bond, hydrogen or a phenyl radical, at least one of the variables C or D or W not being a bond and U only being a hetero atom grouping if C is not a bond or if D and/or W are not a bond, and C, D and/or W are substituted by hydrogen or by 1 or 2 substituents from the following series fluorine, chlorine, ($C_1$-$C_6$)-alkyl, phenyl, ($C_1$-$C_6$)-alkoxy, phenoxy, —O—$[CH_2]_x C_f H_{(2f+1-g)} F_g$, carbamoyl, N-($C_1$-$C_{10}$)-alkylcarbamoyl, N,N-di-($C_1$-$C_8$)-alkylcarbamoyl, N-($C_3$-$C_8$)-cycloalkylcarbamoyl, N-phenylcarbamoyl, N-($C_7$-$C_{16}$)-phenylalkylcarbamoyl, N-($C_1$-$C_8$)-alkyl-N-($C_6$-$C_{16}$)-phenylcarbamoyl, N-($C_1$-$C_8$)-alkyl-N-($C_7$-$C_{16}$)-phenylalkylcarbamoyl, N-(($C_1$-$C_4$)-alkoxy-($C_1$-$C_8$)-alkyl)carbamoyl, N-phenoxy-($C_1$-$C_8$)-alkyl)carbamoyl, N-(($C_7$-$C_{16}$)-phenylalkyloxy-($C_1$-$C_8$)-alkyl)carbamoyl, N-($C_1$-$C_8$)-alkyl-N-(($C_1$-$C_6$)-alkoxy-($C_1$-$C_8$)-alkyl)carbamoyl, N-($C_1$-$C_8$)-alkyl-N-(($C_6$-$C_{12}$)-phenoxy-($C_1$-$C_8$)-alkyl)carbamoyl, N-($C_1$-$C_8$)-alkyl-N-(($C_7$-$C_{16}$)-phenylalkyloxy-($C_1$-$C_8$)-alkyl)carbamoyl, ($C_1$-$C_8$)-alkanoylamino, ($C_3$–$C_8$)-cycloalkanoylamino, ($C_6$–$C_{12}$)-phenylamino, ($C_7$–$C_{11}$)-phenylalkanoylamino, ($C_1$–$C_8$)-alkanoyl-N-($C_1$–$C_{10}$)-alkylamino, ($C_3$–$C_8$)-cycloalkanoyl-N-($C_1$–$C_6$)-alkylamino, benzoyl-N-($C_1$–$C_{10}$)-alkylamino, ($C_7$–$C_{11}$)-phenylalkanoyl-N-($C_1$–$C_6$)-alkylamino, ($C_1$–$C_{10}$)-alkanoylamino-($C_1$–$C_2$)-alkyl, ($C_3$–$C_8$)-cycloalkanoylamino-($C_1$–$C_2$)-alkyl, benzoylamino($C_1$–$C_2$)-alkyl and ($C_7$–$C_{14}$)-phenylalkanoylamino($C_1$–$C_2$)-alkyl, the radicals which contain an aryl radical being substituted in turn by a substituent from the series comprising hydrogen, hydroxyl, fluorine, chlorine, trifluoromethyl, ($C_1$–$C_6$)-alkyl and ($C_1$–$C_8$)-alkoxy, n is 0,
f is 1 to 5,
g is 0 or 1 to (2f+1) and
x is 0 or 1, excluding the compounds
methyl 5-[((methylsulfonyl)amino)carbonyl]-pyridine-2-carboxylate,
methyl 5-[((2-propylsulfonyl)amino)carbonyl]-pyridine-2-carboxylate,
methyl 5-[((phenylsulfonyl)amino)carbonyl]-pyridine-2-carboxylate,
methyl 5-[((benzylsulfonyl)amino)carbonyl]-pyridine-2-carboxylate,
methyl 5-[((4-methoxyphenylsulfonyl)amino)carbonyl]-pyridine-2-carboxylate,
methyl 5-[((1-naphthylsulfonyl)amino)carbonyl]-pyridine-2-carboxylate,
methyl 5-[((4,5-dibromo-2-thienylsulfonyl)amino)carbonyl]-pyridine-2-carboxylate,
methyl 5-[((5-chloro-2-thienylsulfonyl)amino)carbonyl]-pyridine-2-carboxylate,
methyl 5-[((8-quinolylsulfonyl)amino)carbonyl]-pyridine-2-carboxylate and
methyl 5-[((4-(2-(4,7-dichloroquinolyl))phenylsulfonyl)amino)carbonyl]-pyridine-2-carboxylate.

The invention furthermore relates to the use of compounds of the formula I and to their physiologically tolerated salts for the preparation of a medicament against fibrotic diseases.

Finally, the invention relates to the compounds of the formula I for use as medicaments.

The invention particularly relates to the compounds of the formula I for use as fibrosuppressants.

The invention furthermore relates to a process for the preparation of compounds of the formula I.

The invention furthermore relates to a process for the preparation of compounds of the formula I (specifically compounds of the formulae 3 and 8 or their N-oxides 3' and 8'):

a) Compounds in which X is a single bond are prepared as follows (Equation I):

i)
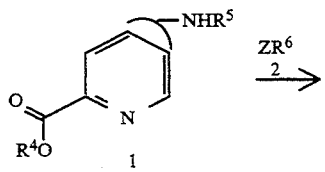

ii)
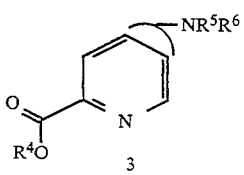

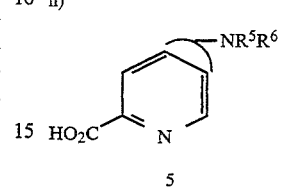

The equation applies both to 2,4-disubstituted pyridine derivatives of the formula I and to the 2,5-derivatives with all the substituents for $R^1$, $R^2$ and $R^3$.

b) Compounds in which X is —CO— are prepared as follows (Equation II):

i)
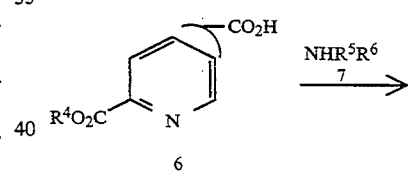

ii)
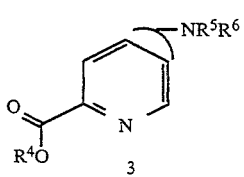

iii)
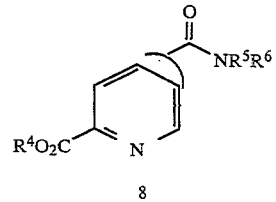

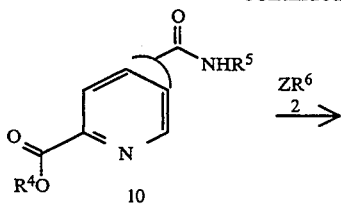

$$\xrightarrow{ZR^6}$$

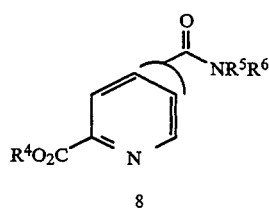

The equation applies both to 2,4-disubstituted pyridine derivatives of the formula I and to the 2,5-derivatives with all the substituents for $R^1$, $R^2$ and $R^3$.

Re Equation I (process a)

i) 5-Aminopyridine-2-carboxylates of the formula 1 are reacted with compounds of the formula 2 in which Z is hydroxyl or a leaving group, which can be detached nucleophilically, and in particular is F, Cl, Br, I or tosylate, to give compounds of the formula 3. This reaction is carried out in a dipolar aprotic organic solvent or a solvent mixture. The following solvents are mentioned in particular: methylene chloride, carbon tetrachloride, butyl acetate, ethyl acetate, toluene, tetrahydrofuran, dimethoxyethane, 1,4-dioxane, acetonitrile, N,N-dimethylformamide, N,N-dimethylacetamide, dimethylsulfoxide, nitromethane and/or pyridine, if appropriate with addition of an acid-binding agent, such as ammonia, triethylamine or tributylamine, at a reaction temperature of 0° to 180° C., preferably 0° to 80° C. If Z is hydroxyl, the method is a condensation method which is known from peptide chemistry (cf. also Method B).

ii) The compounds of the formula 5 are esterified with an alcohol of the formula 4 by methods which are known and customary to the expert to give compounds of the formula 3. This method is used in particular if $R^4$ in the compounds of the formula 3 which result from process i) is lower alkyl, in particular methyl. In this case, these compounds of the formula 3 are first hydrolyzed to the compounds of the formula 5 and then reacted with alcohols of the formula 4 in which $R^4$ is not lower alkyl, in particular methyl.

The starting compounds for process ii), compounds of the formula 5, can be prepared by hydrolysis of the compounds of the formula 1.

The compounds of the formula 3 furthermore can be converted into the pyridine N-oxides 3' by methods which are known to the expert.

General instructions for this oxidation method are described in "E. Klingsberg, Pyridine and its Derivatives, Interscience Publishers, New York, 1961, Part 2, 93". Oxidation with hydrogen peroxide is described, for example, in "E. Ochiai, J. Org. Chem. 18, 534 (1953)". The process conditions can be found in detail in German Patent Applications P 38 26 471.4, 38 28 140.6, 39 24 093.2 and 40 01 002.3 and DE A 37 03 959, 37 03 962 and 37 03 963.

The preparation of the compounds of the formula 1, which are known from the literature, is described by N. Finch et al., J. Med. Che. (1978), Volume 21, page 1269 and Schneider and Harris, J. Org. Chem. (1984), Volume 49, page 3683.

Re Equation II (process b)

i) The pyridine-2-carboxylic acid 5-carboxylates of the formula 6 can be prepared from substituted pyridine-2,5-dicarboxylic acids (see CA: Volume 68, 1968, 68840 h). Suitable conditions are, for example, esterification with methanol in the presence of sulfuric acid, the reaction time being chosen such that complete esterification to the diester product takes place to only a minor degree, or the diester products can be separated off as by-products.

The compounds of the formula 8 are prepared from the compounds of the formula 6 and the amide derivatives of the formula 7, it being expedient to activate the two reactants with auxiliary reagents (Houben-Weyl: Methoden der Organischen Chemie [Methods of Organic Chemistry], Volume IX, Chapter 19, pages 636 to 637).

Reagents which can be used for carboxylic acid reactivation are the substances known to the expert, such as thionyl chloride, oxalyl chloride, pivaloyl chloride or chloroformic acid ester derivatives. It is not always necessary to isolate these activated derivatives of the compounds of the formula 7. It is usually expedient for them to be reacted with the sulfonamide derivatives of the formula 8 in situ after their preparation or as crude products.

The compounds of the formula 7 are expediently first reacted with an inorganic or organic base, such as, for example, sodium hydroxide, carbonate, alkoxide, hydride or amide, potassium hydroxide, carbonate, alkoxide, hydride or amide, ammonia, triethylamine, tributylamine or pyridine, at $-20°$ to $+150°$ C., preferably at 0° to $-80°$ C., and this reaction mixture is reacted with a compound of the formula 6 or the activated form thereof. The reaction is carried out in an inert solvent, such as, for example, methylene chloride, methanol, ethanol, acetone, ethyl acetate, toluene, tetrahydrofuran, acetonitrile, N,N-dimethylformamide, N,N-dimethylacetamide, nitromethane, dimethyl sulfoxide or mixtures of these solvents.

ii) The compounds of the formula 9 are esterified with an alcohol of the formula 4 to give compounds of the formula 8 by methods which are known and customary to the expert (see Method a ii). In this case also, this method is used in particular if $R^4$ in the compounds of the formula 8 which result from process i) is lower alkyl, in particular methyl. In this case, these compounds of the formula 8 are first hydrolyzed to the compounds of the formula 9 and then reacted with alcohols of the formula 4 in which $R^4$ is not lower alkyl, in particular methyl.

iii) This method essentially corresponds to Method a i). Compounds of the formula 10 (preparation, for example, from 6) are reacted with compounds of the formula 2 in which Z is hydroxyl or a leaving group which can be detached nucleophilically, and in particular is F, Cl, Br, I or tosylate, to give compounds of the formula 8. This reaction is carried out in a dipolar aprotic organic solvent or a solvent mixture. The following solvents are mentioned in particular: methylene chloride, carbon tetrachloride, butyl acetate, ethyl acetate, toluene, tetrahydrofuran, dimethoxyethane, 1,4-dioxane, acetonitrile, N,N-dimethylformamide, N,N-dimethylacetamide, dimethyl sulfoxide, nitromethane and/or pyridine, if appropriate with addition of an acid-binding agent, such as ammonia, triethylamine or tributylamine, at a reaction temperature of 0° to 180° C., preferably 0° to 80° C. If Z is hydroxyl, the method is a condensation method which is known from peptide chemistry (cf. also Method B).

The compounds of the formula 8 furthermore can be converted into the pyridine N-oxides 8' by methods which are known to the expert. The information necessary for this is summarized under Method a ii).

Neutral compounds are employed for the preparation of compounds according to the formula I (3, 3', 8, 8') by Equations I and II. If appropriate, salt formation can be carried out after conclusion of the synthesis. Possible salt-forming agents are, preferably, N-alkylamines, (hydroxyalkyl)amines and (alkoxyalkyl)amines, such as, for example, 2-ethanolamine, 3-propanolamine, 2-methoxyethylamine, 2-ethoxyethylamine and α,α,α-tris-(hydroxymethyl)methylamine (=tris buffer or Tromethane) or basic amino acids, such as, for example, histidine, arginine and lysine.

The compounds of the formula I according to the invention have valuable pharmacological properties and exhibit, in particular, antifibrotic activity.

The antifibrotic action can be determined in the model of carbon tetrachloride-induced fibrosis of the liver. For this, rats are treated twice weekly with CCl$_4$ (1 ml/kg)—dissolved in olive oil. The test substance is administered daily, if appropriate even twice daily, perorally or intraperitoneally—dissolved in a suitable tolerated solvent. The extent of the liver fibrosis is determined histologically and the content of collagen in the liver is analyzed by hydroxyproline determination—as described by Kivirikko et al. (Anal. Biochem. 19, 249 et seq. (1967). The activity of the fibrogenesis can be determined by radioimmunological assay of collagen fragments and procollagen peptides in the serum. The compounds according to the invention are active in this model in concentrations of 1 to 100 mg/kg.

The activity of the fibrogenesis can be determined by radioimmunological assay of the N-terminal propeptide of the collagen type III or of the N- or C-terminal cross-linking domains of the collagen type IV (7s-collagen or type IV collagen NC$_1$) in the serum.

For this purpose, the hydroxyproline, procollagen III peptide, 7s-collagen and type IV collagen NC concentrations in the liver of
  a) untreated rats (control)
  b) rats to which carbon tetrachloride was administered (CCl$_4$ control)
  c) rats to which first CCl$_4$ and then a compound according to the invention were administered
were measured (this test method is described by Rouiller, C., Experimental toxic injury of the liver; in The Liver, C. Rouiller, Volume 2, page 335 to 476, New York, Academic Press, 1964).

The compounds of the formula I can be used as medicaments in the form of pharmaceutical preparations which comprise them, if appropriate together with tolerated pharmaceutical excipients. The compounds can be used as medicines, for example in the form of pharmaceutical preparations which comprise these compounds as a mixture with a pharmaceutical, organic or inorganic excipient suitable for enteral, percutaneous or parenteral administration, such as, for example, water, gum arabic, gelatin, lactose, starch, magnesium stearate, talc, vegetable oils, polyalkylene glycols, petroleum jelly and the like.

They can be administered for this purpose orally in doses of 0.1 to 25 mg/kg/day, preferably 1 to 5 mg/kg/day, or parenterally in doses of 0.01 to 5 mg/kg/day, preferably 0.01 to 2.5 mg/kg/day, in particular 0.5 to 1.0 mg/kg/day. In serious cases, the dosage can also be increased. In many cases, however, lower doses are also sufficient. These data relate to an adult weighing 75 kg.

In Examples 1 to 592, corresponding to formula I, X is CO. The methyl pyridine-2-carboxylate derivatives described in the following examples were prepared
  from methyl pyridine-2-carboxylate-5-carbonyl chloride and the corresponding amides of the formula 7/potassium tert-butylate, as described explicitly for Examples 1b, 3, 4 and 68 (Method A), or
  from methyl pyridine-2-carboxylate-5-carboxylic acid, the corresponding amides of the formula 7 and N,N'-dicyclohexylcarbodiimide/4-N,N-dimethylaminopyridine, as described explicitly for Example 32 (Method B).

EXAMPLE 1

2-Propyl 5-[((4-methoxyphenylsulfonyl)amino)carbonyl]-pyridine-2-carboxylate a) Methyl pyridine-2-carboxylate-5-carbonyl chloride 6.48 ml of thionyl chloride and 2 ml of anhydrous N,N-dimethylacetamide were added to 14.5 g (80 mmol) of methyl pyridine-2-carboxylate-5-carboxylic acid in 200 ml of anhydrous toluene. The mixture was heated at 70° C. for 3 hours with stirring. Thereafter, it was concentrated in vacuo and the residue was dissolved in 150 ml of tetrahydrofuran.

b) Methyl 5-[((4-methoxyphenylsulfonyl)amino)carbonyl]-pyridine-2-carboxylate

Method A:

19.75 g (176 mmol) of potassium tert-butylate were added to 16.45 g (88 mmol) of 4-methoxybenzenesulfonamide in 200 ml of tetrahydrofuran at 0° C. After the mixture had been stirred at room temperature for 3 hours, the solution from Example 1a) was added at 0° to 5° C. The mixture was stirred for 3 hours, while warming to room temperature, 300 ml of ethyl acetate were added, the mixture was extracted twice with aqueous NaHCO$_3$ solution, the aqueous phase was acidified with concentrated aqueous hydrochloric acid, extracted 3 times with methylene chloride, dried and concentrated and the residue was crystallized from methanol to give 9.9 g of colorless, crystalline product, melting point 197° to 199° C.

c) 5-[(4-Methoxyphenylsulfonyl)aminocarbonyl]-pyridine-2-carboxylate 3.0 g (8.6 mmol) of the compound from Example 1b) were dissolved in 100 ml of methanol, and 17.2 ml (17.2 mmol) of 1 n NaOH were added at 0° to 5° C. After the mixture had been stirred at room temperature for 4 hours, it was concentrated in vacuo, the residue was taken up in water, 17.2 ml (17.2 mmol) of 1N HCl were added at 0° to 5° C. and the solid was filtered off with suction and washed several times with water to give 2.58 g of the above compound, melting point 234° to 236° C.

d) 4 drops of concentrated sulfuric acid were added to 0.58 g (1.73 mmol) of the above pyridine-2-carboxylic acid derivative in 50 ml of anhydrous 2-propanol, and the mixture was stirred at 80° C. for 56 hours. After cooling, it was concentrated in vacuo, the residue was treated with saturated aqueous NaHCO3 solution and acidified with aqueous hydrochloric acid, and the crystalline crude product was filtered off with suction, washed with water and recrystallized from methanol. This gave 0.47 g of the title compound, melting point 215° to 216° C.

EXAMPLE 2

3-Pentyl 5-[((phenylsulfonyl)amino)carbonyl]-pyridine-2-carboxylate a) Methyl 5-[((phenylsulfonyl)amino)carbonyl]-pyridine-2-carboxylate The compound was obtained analogously to Example 1b) from 3.46 g (22 mmol) of benzenesulfonamide, 2.46 g (22 mmol) of potassium tert-butylate and 4.0 g (20 mmol) of methyl pyridine-2-carboxylate-5-carbonyl chloride. Recrystallization from methanol gave 1.6 g of product, melting point 197° to 198° C.

b) 5-[((Phenylsulfonyl)amino)carbonyl]-pyridine-2-carboxylate 3.5 g (10.94 mmol) of the above compound were stirred under reflux in 150 ml of 1.5N methanolic sodium hydroxide solution for 30 minutes. The mixture was then concentrated in vacuo, the residue was dissolved in a little water/tetrahydrofuran, the solution was acidified to pH 1 with aqueous hydrochloric acid and cooled and the product was filtered off with suction and dried. This gave 2.6 g; melting point 247° to 248° C.

c) 5 drops of concentrated sulfuric acid were added to 0.9 g (2.94 mmol) of 5-[((phenylsulfonyl)amino)carbonyl]-pyridine-2-carboxylate in 30 ml of 3-pentanol, while stirring, and the mixture was heated at 90° C. for 6 hours. The excess 3-pentanol was distilled off in vacuo and the residue was treated with ethyl acetate. The crystalline crude product was combined with the product obtained from the mother liquor by purification by column chromatography (melting point 186° to 187° C.), treated with hot ethyl acetate, cooled, filtered off with suction and washed with ethyl acetate. This gave 0.55 g of the colorless title compound, melting point 182° to 183° C.

EXAMPLE 3

Methyl 5-[((4-n-butoxyphenylsulfonyl)amino)carbonyl]-pyridine-2-carboxylate a) 4-n-Butoxybenzenesulfonamide 100 ml of methanolic ammonia solution were added dropwise to 10 g of 4-n-butoxybenzenesulfonyl chloride, while cooling with ice. After the mixture had been stirred at 20° C. for ½ hour, water was added, the mixture was acidified to pH 1 to 2 and the product was filtered off with suction, melting point 99° to 101° C.

b) 4.6 g (20 mmol) of the above compound, 2.5 g (22 mmol) of potassium tert-butylate and 5.0 g (25 mmol) of methyl pyridine-2-carboxylate-5-carbonyl chloride were reacted analogously to Example 1b). The potassium salt which had precipitated was acidified with 2 n HCl in a dioxane/water mixture. The product which had precipitated was filtered off with suction and dried; yield 1.5 g; melting point 174° to 176° C.

EXAMPLE 4

Methyl 5-[((4-trifluoromethoxyphenylsulfonyl)amino)carbonyl]-pyridine-2-carboxylate a) 4-Trifluoromethoxybenzenesulfonamide was obtained from the corresponding sulfonic acid chloride by reaction with methanolic ammonia solution. Water was added to the crude product, the mixture was acidified and the product was filtered off with suction and dried, melting point 143° to 145° C.

b) 4.8 g (20 mmol) of the above compound, 2.5 g (22 mmol) of potassium tert-butylate in dioxane and 5 g (25 mmol) of methyl pyridine-2-carboxylate-5-carbonyl chloride were reacted analogously to Example 1b). After concentration, the residue was taken up in water, the mixture was acidified and the precipitate was filtered off with suction and dried; 3.4 g of crude product (melting point 210° to 214° C.), which was recrystallized from 75 ml of ethyl acetate to give 1.5 g of colorless crystalline substance, melting point 221° to 223° C.

EXAMPLE 5

Methyl 5-[((4-fluorophenyl)sulfonyl)amino)carbonyl]-pyridine-2-carboxylate

The title compound is obtained analogously to Example 1b) from 4-fluorobenzenesulfonamide and methyl pyridine-2-carboxylate-5-carbonyl chloride; melting point 221° to 223° C.

EXAMPLE 6

Ethyl 5-[((4-methoxyphenylsulfonyl)amino)carbonyl]-pyridine-2-carboxylate

EXAMPLE 7 n-Propyl 5-[((4-methoxyphenylsulfonyl)amino)carbonyl]-pyridine-2-carboxylate

EXAMPLE 8

1-(2-Methylpropyl) 5-[((4-methoxyphenylsulfonyl)amino)carbonyl]-pyridine-2-carboxylate

EXAMPLE 9

3-Pentyl 5-[((4-methoxyphenylsulfonyl)amino)carbonyl]-pyridine-2-carboxylate

EXAMPLE 10

Cyclohexyl 5-[((4-methoxyphenylsulfonyl)amino)carbonyl]-pyridine-2-carboxylate

EXAMPLE 11

Cyclopentyl 5-[((4-methoxyphenylsulfonyl)amino)carbonyl]-pyridine-2-carboxylate

EXAMPLE 12

Methyl 5-[((4-phenoxy-phenylsulfonyl)amino)carbonyl]-pyridine-2-carboxylate, Method A Melting point 194° to 196° C. (from methanol)

EXAMPLE 13

2-Propyl 5-[((4-phenoxy-phenylsulfonyl)amino)carbonyl]-pyridine-2-carboxylate

EXAMPLE 14

Cyclohexyl 5-[((4-phenoxy-phenylsulfonyl)amino)carbonyl]-pyridine-2-carboxylate

EXAMPLE 15

Methyl 5-[((2-phenyl-phenylsulfonyl)amino)carbonyl]-pyridine-2-carboxylate

EXAMPLE 16

2-Propyl 5-[((2-phenyl-phenylsulfonyl)amino)carbonyl]-pyridine-2-carboxylate

EXAMPLE 17

Methyl 5-[((n-butylsulfonyl)amino)carbonyl]-pyridine-2-carboxylate, Method A

Melting point 160° to 162° C. (from diethyl ether)

EXAMPLE 18

2-Propyl 5-[((n-butylsulfonyl)amino)carbonyl]-pyridine-2-carboxylate

EXAMPLE 19

3-Pentyl 5-[((n-butylsulfonyl)amino)carbonyl]-pyridine-2-carboxylate

EXAMPLE 20

Methyl 5-[((4-[3-trifluoromethyl)phenoxy]phenylsulfonyl)amino)carbonyl]-pyridine-2-carboxylate, Method B Melting point 190° to 192° C. (from diisopropyl ether)

EXAMPLE 21

Ethyl 5-[((4-[3-(trifluoromethyl)phenyloxy]phenylsulfonyl)amino)carbonyl]-pyridine-2-carboxylate

EXAMPLE 22

Ethyl 5-[((1-naphthylsulfonyl)amino)carbonyl]-pyridine-2-carboxylate

EXAMPLE 23 n-Butyl 5-[((1-naphthylsulfonyl)amino)carbonyl]-pyridine-2-carboxylate

EXAMPLE 24

2-Propyl 5-[((1-naphthylsulfonyl)amino)carbonyl]-pyridine-2-carboxylate

EXAMPLE 25

3-Pentyl 5-[((1-naphthylsulfonyl)amino)carbonyl]-pyridine-2-carboxylate

EXAMPLE 26

Ethyl 5-[((2-naphthylsulfonyl)amino)carbonyl]-pyridine-2-carboxylate

EXAMPLE 27

Ethyl 5-[((phenylsulfonyl)amino)carbonyl]-pyridine-2-carboxylate

EXAMPLE 28

1-Propyl 5-[((phenylsulfonyl)amino)carbonyl]-pyridine-2-carboxylate

EXAMPLE 29

2-Propyl 5-[((phenylsulfonyl)amino)carbonyl]-pyridine-2-carboxylate

EXAMPLE 30

1-Pentyl 5-[((phenylsulfonyl)amino)carbonyl]-pyridine-2-carboxylate

EXAMPLE 31

1-(2-Methylpropyl) 5-[((phenylsulfonyl)amino)carbonyl]-pyridine-2-carboxylate

EXAMPLE 32

Methyl 5-[((4-((2-phenylethyl)aminocarbonyl)phenylsulfonyl)amino)carbonyl]-pyridine-2-carboxylate a) 4-((2-Phenylethyl)aminocarbonyl)benzenesulfonamide 20.1 g (0.1 mol) of 4-carboxy-benzenesulfonamide were suspended in 300 ml of anhydrous tetrahydrofuran, and 15.2 ml (0.11 mol) of triethylamine were added dropwise at 0° C., while stirring. After 30 minutes, 10.5 ml (0.11 mol) of ethyl chloroformate were added dropwise at 0° C., the mixture was stirred at this temperature for 1 hour and cooled to −10° C., and 12.1 g (0.1 mol, 12.5 ml) of 2-phenylethylamine in 30 ml of anhydrous tetrahydrofuran were added dropwise. After 1 hour at 0° C., the mixture was warmed to 20° C. and concentrated in vacuo and the solid residue was treated with water, filtered off with suction and recrystallized from ethanol to give 20.4 g of product, melting point 243° to 245° C.

b) Method B:

1.8 g (10 mmol) of 2-methyl pyridine-2,5-dicarboxylic acid were suspended in 300 ml of anhydrous acetonitrile, 3.0 g (10 mmol) of the above compound, 2.1 g (10 mmol) of N,N'-dicyclohexylcarbodiimide and 1.2 g (10 mmol) of 4-N,N-dimethylaminopyridine were added at 20° C., while stirring, and the mixture was stirred at 20° C. for 20 hours. The undissolved substance was then filtered off, the filtrate was concentrated in vacuo, the residue was taken up in 200 ml of methylene chloride and the mixture was extracted twice with saturated aqueous NaHCO₃ solution and then with 100 ml of 2N aqueous HCl. The crystalline precipitate was then treated with hot methanol, filtered off with suction and dried. This gave 2.2 g of the ester, melting point 228° to 230° C.

Examples 33 to 67 were prepared by Method B:

EXAMPLE 33

Methyl 5-[((4-benzylaminocarbonyl)phenylsulfonyl)amino)carbonyl]-pyridine-2-carboxylate

EXAMPLE 34

Methyl 5-[((4-((3-phenyl-n-propyl)aminocarbonyl)phenylsulfonyl)amino)carbonyl]-pyridine-2-carboxylate Melting point 240° to 242° C. (from methanol)

EXAMPLE 35

Methyl 5-[((4-((4-phenyl-n-butyl)aminocarbonyl)phenylsulfonyl)amino)carbonyl]-pyridine-2-carboxylate Melting point 223° to 225° C. (from methanol)

EXAMPLE 36

Methyl 5-[((4-((2-(4-methoxyphenyl)ethyl)aminocarbonyl)phenylsulfonyl)amino)carbonyl]-pyridine-2-carboxylate Melting point 240° to 242° C. (from methanol)

EXAMPLE 37

Methyl 5-[((4-((2-(3,4-dimethoxyphenyl)ethyl)aminocarbonyl)phenylsulfonyl)amino)carbonyl]-pyridine-2-carboxylate Melting point 213° to 215° C. (from methanol)

EXAMPLE 38

Methyl 5-[((4-((2-(2-methoxyphenyl)ethyl)aminocarbonyl)phenylsulfonyl)amino)carbonyl]-pyridine-2-carboxylate Melting point 220° to 222° C. (from methanol)

EXAMPLE 39

Methyl 5-[((4-((2-(4-fluorophenyl)ethyl)aminocarbonyl)phenylsulfonyl)amino)carbonyl]-pyridine-2-carboxylate

EXAMPLE 40

Methyl 5-[((4-((2-(4-chlorophenyl)ethyl)aminocarbonyl)phenylsulfonyl)amino)carbonyl]-pyridine-2-carboxylate

EXAMPLE 41

Methyl 5-[((4-(ethylaminocarbonyl)phenylsulfonyl)amino)carbonyl]-pyridine-2-carboxylate

EXAMPLE 42

Methyl 5-[((4-(n-butylaminocarbonyl)phenylsulfonyl)amino)carbonyl]-pyridine-2-carboxylate

EXAMPLE 43

Methyl 5-[((4-(n-hexylaminocarbonyl)phenylsulfonyl)amino)carbonyl]-pyridine-2-carboxylate

EXAMPLE 44

Methyl 5-[((4-(N,N-di-n-butylaminocarbonyl)phenylsulfonyl)amino)carbonyl]-pyridine-2-carboxylate

EXAMPLE 45

Methyl 5-[((4-cyclohexylaminocarbonyl)phenylsulfonyl)amino)carbonyl]-pyridine-2-carboxylate

EXAMPLE 46

Methyl 5-[((4-(2-methoxyethyl)aminocarbonyl)phenylsulfonyl)amino)carbonyl]-pyridine-2-carboxylate

EXAMPLE 47

Methyl 5-[((4-((2-ethoxyethyl)aminocarbonyl)phenylsulfonyl)amino)carbonyl]-pyridine-2-carboxylate

EXAMPLE 48

Methyl 5-[((4-((3-ethoxypropyl)aminocarbonyl)phenylsulfonyl)amino)carbonyl]-pyridine-2-carboxylate 9.9 g of the title compound were obtained by Method B from 5.4 g of methyl pyridine-2-carboxylate-5-carboxylic acid, 6.3 g of N,N'-dicyclohexylcarbodiimide, 3.6 g of 4-N,N-dimethylamino-pyridine and 9 g of 4-((3-ethoxypropyl)aminocarbonyl)benzenesulfonamide (in each case 30 mmol); melting point 194° to 196° C. (from ethyl acetate)

EXAMPLE 49

Methyl 5-[((4-((2-phenoxyethyl)aminocarbonyl)phenylsulfonyl)amino)carbonyl]-pyridine-2-carboxylate

EXAMPLE 50

Methyl 5-[((3-(benzylaminocarbonyl)phenylsulfonyl)amino)carbonyl]-pyridine-2-carboxylate

EXAMPLE 51

Methyl 5-[((3-((3-phenylpropyl)aminocarbonyl)phenylsulfonyl)amino)carbonyl]-pyridine-2-carboxylate

EXAMPLE 52

Methyl 5-[((3-((4-phenyl-n-butyl)aminocarbonyl)phenylsulfonyl)amino)carbonyl]-pyridine-2-carboxylate Melting point 188° to 191° C.

EXAMPLE 53

Methyl 5-[((3-((2-(3,4-dimethoxyphenyl)ethyl)aminocarbonyl)phenylsulfonyl)amino)carbonyl]-pyridine-2-carboxylate

EXAMPLE 54

Methyl 5-[((3-((2-(3-methoxyphenyl)ethyl)aminocarbonyl)phenylsulfonyl)amino)carbonyl]-pyridine-2-carboxylate

EXAMPLE 55

Methyl 5-[((3-((2-(2-methoxyphenyl)ethyl)aminocarbonyl)phenylsulfonyl)amino)carbonyl]-pyridine-2-carboxylate

EXAMPLE 56

Methyl 5-[((3-((2-(4-fluorophenyl)ethyl)aminocarbonyl)phenylsulfonyl)amino)carbonyl]-pyridine-2-carboxylate

EXAMPLE 57

Methyl 5-[((3-((2-(4-chlorophenyl)ethyl)aminocarbonyl)phenylsulfonyl)amino)carbonyl]-pyridine-2-carboxylate

EXAMPLE 58

Methyl 5-[((3-(ethylaminocarbonyl)phenylsulfonyl)amino)carbonyl]-pyridine-2-carboxylate

EXAMPLE 59

Methyl 5-[((3-(n-butylaminocarbonyl)phenylsulfonyl)amino)carbonyl]-pyridine-2-carboxylate

EXAMPLE 60

Methyl 5-[((3-(n-hexylaminocarbonyl)phenylsulfonyl)amino)carbonyl]-pyridine-2-carboxylate

EXAMPLE 61

Methyl 5-[((3-(N,N-di-n-butylaminocarbonyl)phenylsulfonyl)amino)carbonyl]-pyridine-2-carboxylate

EXAMPLE 62

Methyl 5-[((3-(cyclohexylaminocarbonyl)phenylsulfonyl)amino)carbonyl]-pyridine-2-carboxylate

EXAMPLE 63

Methyl 5-[((3-((2-methoxyethyl)aminocarbonyl)phenylsulfonyl)amino)carbonyl]-pyridine-2-carboxylate

EXAMPLE 64

Methyl 5-[((3-((3-ethoxypropyl)aminocarbonyl)phenylsulfonyl)amino)carbonyl]-pyridine-2-carboxylate

EXAMPLE 65

Methyl 5-[((3-((3-methoxypropyl)aminocarbonyl)phenylsulfonyl)amino)carbonyl]-pyridine-2-carboxylate

EXAMPLE 66

Methyl 5-[((3-((2-phenylethyl)aminocarbonyl)phenylsulfonyl)amino)carbonyl]-pyridine-2-carboxylate Melting point 214° to 216° C.

EXAMPLE 67

Methyl 5-[((3-((2-phenoxyethyl)aminocarbonyl)phenylsulfonyl)amino)carbonyl]-pyridine-2-carboxylate

EXAMPLE 68

Methyl 5-[((4-(2-((2-chloro-5-methoxybenzoyl)amino)ethyl)phenylsulfonyl)amino)carbonyl]-pyridine-2-carboxylate (Method A)

The methyl pyridine-2,5-carboxylate-5-carbonyl chloride prepared from 4.0 g (22 mmol) of pyridine-2,5-dicarboxylic acid 2-methyl ester as described in Example 1c) was added, in 50 ml of anhydrous 1,4-dioxane, to the reaction mixture of 7.4 g (20 mmol) of 2-(((2-chloro-5-methoxybenzoyl)amino)ethyl)benzenesulfonamide (prepared from 4-(2-aminoethyl)benzenesulfonamide and 2-chloro-5-methoxybenzoic acid), 2,3 g (20 mmol) of potassium tert-butylate in 150 ml of anhydrous 1,4-dioxane at 40° C. (the mixture had been stirred at 50° C. for 15 minutes for formation of the sulfonamide sodium salt).

The reaction mixture was stirred at 60° C. for 90 minutes and then under reflux for 2 hours, the solvent was distilled off in vacuo, water was added to the residue, the pH was brought to 1 to 2 with aqueous HCl and the mixture was extracted with methylene chloride.

The residue was treated with hot ethyl acetate, filtered off with suction and washed with ethyl acetate. The crude product thus obtained (2.8 g) was treated with 100 ml of cold water and then with 100 ml of hot water and the colorless crystalline product was filtered off with suction. This gave 2.6 g, melting point 187° to 190° C.

EXAMPLE 69

Methyl 5-[((4-(2-(n-pentanoylamino)ethyl)phenylsulfonyl)amino)carbonyl]-pyridine-2-carboxylate (Method B)

Melting point 178° to 180° C. (from aqueous hydrochloric acid)

EXAMPLE 70

Methyl 5-[((4-(2-(n-butanoylamino)ethyl)phenylsulfonyl)amino)carbonyl]-pyridine-2-carboxylate (Method B)

Melting point 195° C.

EXAMPLE 71

Methyl 5-[((4-(2-(benzoylamino)ethyl)phenylsulfonyl)amino)carbonyl]-pyridine-2-carboxylate (Method A)

Melting point 228° to 230° C. (from methanol)

EXAMPLE 72

Methyl 5-[((4-(2-((4-chlorobenzoyl)amino)ethyl)phenylsulfonyl)amino)carbonyl]-pyridine-2-carboxylate Na salt (Method A)

Melting point 260° to 262° C. (from aqueous NaHCO$_3$ solution)

EXAMPLE 73

Methyl 5-[((4-(2-((5-chloro-2-methoxybenzoyl)amino)ethyl)phenylsulfonyl)amino)carbonyl]-pyridine-2-carboxylate (Method A)

Melting point 233° C. (from aqueous hydrochloric acid)

EXAMPLE 74

Methyl 5-[((4-(2-((3-phenyl-n-propionyl)amino)ethyl)phenylsulfonyl)amino)carbonyl]-pyridine-2-carboxylate Na salt (Method A)

Melting point 236° to 238° C. (from aqueous NaHCO$_3$ solution)

EXAMPLE 75

Methyl 5-[((4-(2-((2-phenylacetyl)amino)ethyl)phenylsulfonyl)amino)carbonyl]-pyridine-2-carboxylate (Method B)

EXAMPLE 76

Methyl 5-[((4-(2-((phenoxyacetyl)amino)ethyl)phenylsulfonyl)amino)carbonyl]-pyridine-2-carboxylate (Method B)

Melting point 201° to 203° C. (from methanol)

EXAMPLE 77

Methyl 5-[((4-(2-((4-fluorobenzoyl)amino)ethyl)phenylsulfonyl)amino)carbonyl]-pyridine-2-carboxylate (Method A)

EXAMPLE 78

Methyl 5-[((4-(2-((4-ethoxybenzoyl)amino)ethyl)phenylsulfonyl)amino)carbonyl]-pyridine-2-carboxylate (Method A)

EXAMPLE 79

Methyl 5-[((4-(2-((cyclohexanoyl)amino)ethyl)phenylsulfonyl)amino)carbonyl]-pyridine-2-carboxylate (Method B)

EXAMPLE 80

Methyl 5-[((4-(2-((cyclohexylacetyl)amino)ethyl)phenylsulfonyl)amino)carbonyl]-pyridine-2-carboxylate (Method B)

Melting point 192° to 194° C. (from methanol/diisopropyl ether)

EXAMPLE 81

Methyl 5-[((4-(2-((2-methylpropionyl)amino)ethyl)phenylsulfonyl)amino)carbonyl]-pyridine-2-carboxylate (Method B)

Melting point 193° to 197° C. (from aqueous hydrochloric acid)

EXAMPLE 82

Methyl 5-[((4-(2-(acetylamino)methyl)phenylsulfonyl)amino)carbonyl]-pyridine-2-carboxylate (Method B)

Melting point 232° to 235° C. (from aqueous hydrochloric acid)

EXAMPLE 83

Methyl 5-[((4-(2-((3-methylbutanoyl)amino)ethyl)phenylsulfonyl)amino)carbonyl]-pyridine-2-carboxylate (Method B)

Melting point 176° to 178° C. (from methanol/diisopropyl ether)

EXAMPLE 84

Methyl 5-[((4-(2-((4-methylpentanoyl)amino)ethyl)phenylsulfonyl)amino)carbonyl]-pyridine-2-carboxylate (Method B)

Melting point 204° to 206° C. (from methanol/water)

EXAMPLE 85

Methyl 5-[((4-(2-((3-cyclohexyl-n-propionyl)amino)ethyl)phenylsulfonyl)amino)carbonyl]-pyridine-2-carboxylate

EXAMPLE 86

Ethyl 5-[((4-(2-(n-pentanoylamino)ethyl)phenylsulfonyl)amino)carbonyl]-pyridine-2-carboxylate

EXAMPLE 87

Methyl 5-[((4-(2-((3-methylbutanoyl)amino)methyl)phenylsulfonyl)amino)carbonyl]-pyridine-2-carboxylate (Method B)

Melting point 216° to 218° C. (from methanol)

EXAMPLE 88

Methyl 5-[((4-(2-(4-methylpropionyl)amino)methyl)phenylsulfonyl)amino)carbonyl]-pyridine-2-carboxylate (Method B)

Melting point 225° to 227° C. (from diisopropyl ether)

EXAMPLE 89

Ethyl 5-[((4-(2-((cyclohexyl-n-propionyl)amino)ethyl)phenylsulfonyl)amino)carbonyl]-pyridine-2-carboxylate

EXAMPLE 90

Propyl 5-[((4-(2-(n-pentanoylamino)ethyl)phenylsulfonyl)amino)carbonyl]-pyridine-2-carboxylate

EXAMPLE 91

Propyl 5-[((4-(2-(3-methylbutanoyl)amino)ethyl)phenylsulfonyl)amino)carbonyl]-pyridine-2-carboxylate

EXAMPLE 92

2-Propyl 5-[((4-(2-((4-methylpentanoyl)amino)ethyl)phenylsulfonyl)amino)carbonyl]-pyridine-2-carboxylate

EXAMPLE 93

2-Propyl 5-[((4-(2-((3-cyclohexyl-n-propionyl)amino)ethyl)phenylsulfonyl)amino)carbonyl]-pyridine-2-carboxylate

EXAMPLE 94

1-Pentyl 5-[((4-(n-pentanoylamino)ethyl)phenylsulfonyl)amino)carbonyl]-pyridine-2-carboxylate

EXAMPLE 95

1-Pentyl 5-[((4-(2-((3-methylbutanoyl)amino)ethyl)phenylsulfonyl)amino)carbonyl]-pyridine-2-carboxylate

EXAMPLE 96

1-Pentyl 5[((4-(2-((4-methylpentanoyl)amino)ethyl)phenylsulfonyl)amino)carbonyl]-pyridine-2-carboxylate

EXAMPLE 97

1-Pentyl 5-[((4-(2-((3-cyclohexyl-n-propionyl)amino)ethyl)phenylsulfonyl)amino)carbonyl]-pyridine-2-carboxylate

EXAMPLE 98

3-Pentyl 5-[((4-(2-(n-pentanoylamino)ethyl)phenylsulfonyl)amino)carbonyl]-pyridine-2-carboxylate

EXAMPLE 99

3-Pentyl 5-[((4-(2-((3-methylbutanoyl)amino)ethyl)phenylsulfonyl)amino)carbonyl]-pyridine-2-carboxylate

EXAMPLE 100

3-Pentyl 5-[((4-(2-((4-methylpentanoyl)amino)ethyl)phenylsulfonyl)amino)carbonyl]-pyridine-2-carboxylate

EXAMPLE 101

3-Pentyl 5-[((4-(2-((3-cyclohexyl-n-propionyl)amino)ethyl)phenylsulfonyl)amino)carbonyl]-pyridine-2-carboxylate

EXAMPLE 102

(2,5-Dimethyl-3-pentyl) 5-[((4-(2-(n-pentanoylamino)ethyl)phenylsulfonyl)amino)carbonyl]-pyridine-2-carboxylate

EXAMPLE 103

(2,5-Dimethyl-3-pentyl) 5-[((4-(2-((3-methylbutanoyl)amino)ethyl)phenylsulfonyl)amino)carbonyl]-pyridine-2-carboxylate

EXAMPLE 104

(2,5-Dimethyl-3-pentyl) 5-[((4-(2-((4-methylpentanoyl)amino)ethyl)phenylsulfonyl)amino)carbonyl]-pyridine-2-carboxylate

EXAMPLE 105

(2,5-Dimethyl-3-pentyl) 5-[((4-(2-((3-cyclohexyl-n-propionyl)amino)ethyl)phenylsulfonyl)amino)carbonyl]-pyridine-2-carboxylate

EXAMPLE 106

Cyclohexyl 5-[((4-(2-(n-pentanoylamino)ethyl)phenylsulfonyl)amino)carbonyl]-pyridine-2-carboxylate

EXAMPLE 107

Cyclohexyl 5-[((4-(2-((3-methylbutanoyl)amino)ethyl)phenylsulfonyl)amino)carbonyl]-pyridine-2-carboxylate

EXAMPLE 108

Cyclohexyl 5-[((4-(2-((4-methylpentanoyl)amino)ethyl)phenylsulfonyl)amino)carbonyl]-pyridine-2-carboxylate

EXAMPLE 109

Cyclohexyl 5-[((4-(2-((3-cyclohexyl-n-propionyl)amino)ethylphenylsulfonyl)amino)carbonyl]-pyridine-2-carboxylate

EXAMPLE 110

Benzyl 5-[((4-(2-((3-methylbutanoyl)amino)ethyl)phenylsulfonyl)amino)carbonyl]-pyridine-2-carboxylate

EXAMPLE 111

Benzyl 5-[((4-(2-((4-methylpentanoyl)amino)ethyl)phenylsulfonyl)amino)carbonyl]-pyridine-2-carboxylate

EXAMPLE 112

3-Pentyl 5-[((4-((2-phenylethyl)aminocarbonyl)phenylsulfonyl)amino)carbonyl]-pyridine-2-carboxylate a) 5-[((4-((2-Phenylethyl)aminocarbonyl)phenylsulfonyl)amino)carbonyl]-pyridine-2-carboxylic acid 0.7 g (1.5 mmol) of the methyl ester described in Example 32b) were introduced into 100 ml of 1.5N methanolic NaOH at 20° C., while stirring. When a solution had formed, a crystalline product precipitated. The mixture was then stirred for a further 30 minutes. It was concentrated in vacuo, the residue was dissolved in a mixture of water and tetrahydrofuran, the solution was acidified to pH=1 with aqueous HCl and concentrated in vacuo and the colorless crystalline product was filtered off with suction. This gave 0.6 g, melting point 263° C. (with decomposition).

b) 5 drops of concentrated $H_2SO_4$ were added to 0.5 g (1.1 mmol) of the above carboxylic acid in 30 ml of 3-pentanol and 20 ml of 1,4-dioxane, and the mixture was heated at 90° to 100° C. for 8 hours while stirring. The insoluble material was separated off, the solution was evaporated, and the residue was crystallized by means of water. This crude product was taken up in ethyl acetate, the solution was dried and evaporated, and the residue was chromatographed on silica gel using acetone/n-heptane (3:1). The fractions containing the title compound were evaporated, and the title compound was crystallized by means of diethyl ether. 0.045 g of the title compound was obtained; m.p. 234° to 235° C.

EXAMPLE 113

3-Pentyl 5-[((4-benzylaminocarbonyl)phenylsulfonyl)amino)carbonyl]-pyridine-2-carboxylate

EXAMPLE 114

3-Pentyl 5-[((4-((3-phenyl-n-propyl)aminocarbonyl)phenylsulfonyl)amino)carbonyl]-pyridine-2-carboxylate

EXAMPLE 115

3-Pentyl 5-[((4-((4-phenyl-n-butyl)aminocarbonyl)phenylsulfonyl)amino)carbonyl]-pyridine-2-carboxylate

EXAMPLE 116

3-Pentyl 5-[((4-((2-(4-methoxyphenyl)ethyl)aminocarbonyl)phenylsulfonyl)amino)carbonyl]-pyridine-2-carboxylate

EXAMPLE 117

3-Pentyl 5-[((4-((2-(3,4-dimethoxyphenyl)ethyl)aminocarbonyl)phenylsulfonyl)amino)carbonyl]-pyridine-2-carboxylate

EXAMPLE 118

3-Pentyl 5-[((4-((2-(2-methoxyphenyl)ethyl)aminocarbonyl)phenylsulfonyl)amino)carbonyl]-pyridine-2-carboxylate

EXAMPLE 119

3-Pentyl 5-[((4-((2-(4-fluorophenyl)ethyl)aminocarbonyl)phenylsulfonyl)amino)carbonyl]-pyridine-2-carboxylate

EXAMPLE 120

3-Pentyl 5-[((4-((2-(4-chlorophenyl)ethyl)aminocarbonyl)phenylsulfonyl)amino)carbonyl]-pyridine-2-carboxylate

EXAMPLE 121

3-Pentyl 5-[((4-(ethylaminocarbonyl)phenylsulfonyl)amino)carbonyl]-pyridine-2-carboxylate

EXAMPLE 122

3-Pentyl 5-[((4-(n-butylaminocarbonyl)phenylsulfonyl)amino)carbonyl]-pyridine-2-carboxylate

EXAMPLE 123

3-Pentyl 5-[((4-(n-hexylaminocarbonyl)phenylsulfonyl)amino)carbonyl]-pyridine-2-carboxylate

EXAMPLE 124

3-Pentyl 5-[((4-(N,N-di-n-butylaminocarbonyl)phenylsulfonyl)amino)carbonyl]-pyridine-2-carboxylate

EXAMPLE 125

3-Pentyl 5-[((4-(cyclohexylaminocarbonyl)phenylsulfonyl)amino)carbonyl]-pyridine-2-carboxylate

EXAMPLE 126

3-Pentyl 5-[((4-(2-methoxyethyl)aminocarbonyl)phenylsulfonyl)amino)carbonyl]-pyridine-2-carboxylate

EXAMPLE 127

3-Pentyl 5-[((4-((2-ethoxyethyl)aminocarbonyl)phenylsulfonyl)amino)carbonyl]-pyridine-2-carboxylate

EXAMPLE 128

3-Pentyl 5-[((4-((3-ethoxypropyl)aminocarbonyl)phenylsulfonyl)amino)carbonyl]-pyridine-2-carboxylate

EXAMPLE 129

3-Pentyl 5-[((4-((2-phenoxyethyl)aminocarbonyl)phenylsulfonyl)amino)carbonyl]-pyridine-2-carboxylate

EXAMPLE 130

3-Pentyl 5-[((3-(benzylaminocarbonyl)phenylsulfonyl)amino)carbonyl]-pyridine-2-carboxylate

EXAMPLE 131

3-Pentyl 5-[((3-((3-phenylpropyl)aminocarbonyl)phenylsulfonyl)amino)carbonyl]-pyridine-2-carboxylate

EXAMPLE 132

3-Pentyl 5-[((3-((4-phenyl-n-butyl)aminocarbonyl)phenylsulfonyl)amino)carbonyl]-pyridine-2-carboxylate

EXAMPLE 133

3-Pentyl 5-[((3-((2-(4-methoxyphenyl)ethyl)aminocarbonyl)phenylsulfonyl)amino)carbonyl]-pyridine-2-carboxylate

EXAMPLE 134

3-Pentyl 5-[((3-((2-(3-methoxyphenyl)ethyl)aminocarbonyl)phenylsulfonyl)amino)carbonyl]-pyridine-2-carboxylate

EXAMPLE 135

3-Pentyl 5-[((3-((2-(2-methoxyphenyl)ethyl)aminocarbonyl)phenylsulfonyl)amino)carbonyl]pyridine-2-carboxylate

EXAMPLE 136

3-Pentyl 5-[((3-((2-(4-fluorophenyl)ethyl)aminocarbonyl)phenylsulfonyl)amino)carbonyl]pyridine-2-carboxylate

EXAMPLE 137

3-Pentyl 5-[((3-((2-(4-chlorophenyl)ethyl)aminocarbonyl)phenylsulfonyl)amino)carbonyl]pyridine-2-carboxylate

EXAMPLE 138

3-Pentyl 5-[((3-ethylaminocarbonyl)phenylsulfonyl)amino)carbonyl]pyridine-2-carboxylate

EXAMPLE 139

3-Pentyl 5-[((3-(n-butylaminocarbonyl)phenylsulfonyl)amino)carbonyl]pyridine-2-carboxylate

EXAMPLE 140

3-Pentyl 5[((3-(n-hexylaminocarbonyl)phenylsulfonyl)amino)carbonyl]pyridine-2-carboxylate

EXAMPLE 141

3-Pentyl 5-[((3-(N,N-di-n-butylaminocarbonyl)phenylsulfonyl)amino)carbonyl]pyridine-2-carboxylate

EXAMPLE 142

3-Pentyl 5-[((3-(cyclohexylaminocarbonyl)phenylsulfonyl)amino)carbonyl]pyridine-2-carboxylate

EXAMPLE 143

3-Pentyl 5-[((3-((2-methoxyethyl)aminocarbonyl)phenylsulfonyl)amino)carbonyl]pyridine-2-carboxylate

EXAMPLE 144

3-Pentyl 5-[((3-((3-ethoxypropyl)aminocarbonyl)phenylsulfonyl)amino)carbonyl]pyridine-2-carboxylate

EXAMPLE 145

3-Pentyl 5-[((3-((3-methoxypropyl)aminocarbonyl)phenylsulfonyl)amino)carbonyl]pyridine-2-carboxylate

EXAMPLE 146

3-Pentyl 5-[((3-((2-phenylethyl)aminocarbonyl)phenylsulfonyl)amino)carbonyl]pyridine-2-carboxylate
Melting point 189° to 191° C. (from water)

EXAMPLE 147

3-Pentyl 5-[((3-((2-phenoxyethyl)aminocarbonyl)phenylsulfonyl)amino)carbonyl]pyridine-2-carboxylate

EXAMPLE 148

Ethyl 5-[((4-(benzylaminocarbonyl)phenylsulfonyl)amino)carbonyl]pyridine-2-carboxylate

EXAMPLE 149

Ethyl 5-[((4-((3-phenyl-n-propyl)aminocarbonyl)phenylsulfonyl)amino)carbonyl]pyridine-2-carboxylate

EXAMPLE 150

Ethyl 5-[((4-((4-phenyl-n-butyl)aminocarbonyl)phenylsulfonyl)amino)carbonyl]pyridine-2-carboxylate

EXAMPLE 151

Ethyl 5-[((4-((2-(4-methoxyphenyl)ethyl)aminocarbonyl)phenylsulfonyl)amino)carbonyl]pyridine-2-carboxylate

EXAMPLE 152

Ethyl 5-[((4-((2-(3-methoxyphenyl)ethyl)aminocarbonyl)phenylsulfonyl)amino)carbonyl]pyridine-2-carboxylate

EXAMPLE 153

Ethyl 5-[((4-((2-(2-methoxyphenyl)ethyl)aminocarbonyl)phenylsulfonyl)amino)carbonyl]pyridine-2-carboxylate

EXAMPLE 154

Ethyl 5-[((4-((2-(4-fluorophenyl)ethyl)aminocarbonyl)phenylsulfonyl)amino)carbonyl]pyridine-2-carboxylate

EXAMPLE 155

Ethyl 5-[((4-((2-(4-chlorophenyl)ethyl)aminocarbonyl)phenylsulfonyl)amino)carbonyl]pyridine-2-carboxylate

EXAMPLE 156

Ethyl 5-[((4-(ethylaminocarbonyl)phenylsulfonyl)amino)carbonyl]pyridine-2-carboxylate

EXAMPLE 157

Ethyl 5-[((4-(n-butylaminocarbonyl)phenylsulfonyl)amino)carbonyl]pyridine-2-carboxylate

EXAMPLE 158

Ethyl 5-[((4-(n-hexylaminocarbonyl)phenylsulfonyl)amino)carbonyl]pyridine-2-carboxylate

EXAMPLE 159

Ethyl 5-[((4-(N,N-di-n-butylaminocarbonyl)phenylsulfonyl)amino)carbonyl]-pyridine-2-carboxylate

EXAMPLE 160

Ethyl 5-[((4-(cyclohexylaminocarbonyl)phenylsulfonyl)amino)carbonyl]-pyridine-2-carboxylate

EXAMPLE 161

Ethyl 5-[((4-((2-methoxyethyl)aminocarbonyl)phenylsulfonyl)amino)carbonyl]-pyridine-2-carboxylate

EXAMPLE 162

Ethyl 5-[((4-((2-ethoxyethyl)aminocarbonyl)phenylsulfonyl)amino)carbonyl]-pyridine-2-carboxylate

EXAMPLE 163

Ethyl 5-[((4-((3-ethoxypropyl)aminocarbonyl)phenylsulfonyl)amino)carbonyl]-pyridine-2-carboxylate

EXAMPLE 164

Ethyl 5-[((4-((2-phenylethyl)aminocarbonyl)phenylsulfonyl)amino)carbonyl]-pyridine-2-carboxylate

EXAMPLE 165

Ethyl 5-[((4-((2-phenoxyethyl)aminocarbonyl)phenylsulfonyl)amino)carbonyl]-pyridine-2-carboxylate

EXAMPLE 166

1-Propyl 5-[((3-(benzylaminocarbonyl)phenylsulfonyl)amino)carbonyl]-pyridine-2-carboxylate

EXAMPLE 167

1-Propyl 5-[((3-((phenylpropyl)aminocarbonyl)phenylsulfonyl)amino)carbonyl]-pyridine-2-carboxylate

EXAMPLE 168

1-Propyl 5-[((3-((4-phenyl-n-butanoyl)aminocarbonyl)-phenylsulfonyl)amino)carbonyl]-pyridine-2-carboxylate

EXAMPLE 169

1-Propyl 5-[((3-((2-(4-methoxyphenyl)ethyl)aminocarbonyl)phenylsulfonyl)amino)carbonyl]-pyridine-2-carboxylate

EXAMPLE 170

1-Propyl 5-[((3-((2-(3-methoxyphenyl)ethyl)aminocarbonyl)phenylsulfonyl)amino)carbonyl]-pyridine-2-carboxylate

EXAMPLE 171

1-Propyl 5-[((3-((2-(2-methoxyphenyl)ethyl)aminocarbonyl)phenylsulfonyl)amino)carbonyl]-pyridine-2-carboxylate

EXAMPLE 172

1-Propyl 5-[((3-((2-(4-fluorophenyl)ethyl)aminocarbonyl)phenylsulfonyl)amino)carbonyl]-pyridine-2-carboxylate

EXAMPLE 173

1-Propyl 5-[((3-((2-(4-chlorophenyl)ethyl)aminocarbonyl)phenylsulfonyl)amino)carbonyl]-pyridine-2-carboxylate

EXAMPLE 174

1-Propyl 5-[((3-(ethylaminocarbonyl)phenylsulfonyl)amino)carbonyl]-pyridine-2-carboxylate

EXAMPLE 175

1-Propyl 5-[((3-(n-butylaminocarbonyl)phenylsulfonyl)amino)carbonyl]-pyridine-2-carboxylate

EXAMPLE 176

1-Propyl 5-[((3-(n-hexylaminocarbonyl)phenylsulfonyl)amino)carbonyl]-pyridine-2-carboxylate

EXAMPLE 177

1-Propyl 5-[((3-(N,N-di-n-butylaminocarbonyl)phenylsulfonyl)amino)carbonyl]-pyridine-2-carboxylate

EXAMPLE 178

1-Propyl 5-[((3-(cyclohexylaminocarbonyl)phenylsulfonyl)amino)carbonyl]-pyridine-2-carboxylate

EXAMPLE 179

1-Propyl 5-[((3-((2-methoxyethyl)aminocarbonyl)-phenylsulfonyl)amino)carbonyl]-pyridine-2-carboxylate

EXAMPLE 180

1-Propyl 5-[((3-((2-ethoxyethyl)aminocarbonyl)phenylsulfonyl)amino)carbonyl]-pyridine-2-carboxylate

EXAMPLE 181

1-Propyl 5-[((3-((3-methoxypropyl)aminocarbonyl)-phenylsulfonyl)amino)carbonyl]-pyridine-2-carboxylate

EXAMPLE 182

1-Propyl 5-[((3-((2-phenylethyl)aminocarbonyl)phenylsulfonyl)amino)carbonyl]-pyridine-2-carboxylate

EXAMPLE 183

1-Propyl 5-[((3-((2-phenoxyethyl)aminocarbonyl)-phenylsulfonyl)amino)carbonyl]-pyridine-2-carboxylate

EXAMPLE 184

2-Propyl 5-[((4-(benzylaminocarbonyl)phenylsulfonyl)amino)carbonyl]-pyridine-2-carboxylate

EXAMPLE 185

2-Propyl 5-[((4-((3-phenylpropyl)aminocarbonyl)-phenylsulfonyl)amino)carbonyl]-pyridine-2-carboxylate

EXAMPLE 186

2-Propyl 5-[((4-((4-phenyl-n-butyl)aminocarbonyl)-phenylsulfonyl)amino)carbonyl]-pyridine-2-carboxylate

EXAMPLE 187

2-Propyl 5-[((4-((2-(4-methoxyphenyl)ethyl)aminocarbonyl)phenylsulfonyl)amino)carbonyl]-pyridine-2-carboxylate

EXAMPLE 188

2-Propyl 5-[((4-((2-(3-methoxyphenyl)ethyl)aminocarbonyl)phenylsulfonyl)amino)carbonyl]-pyridine-2-carboxylate

EXAMPLE 189

2-Propyl 5-[((4-((2-(2-methoxyphenyl)ethyl)aminocarbonyl)phenylsulfonyl)amino)carbonyl]-pyridine-2-carboxylate

EXAMPLE 190

2-Propyl 5-[((4-((2-(4-fluorophenyl)ethyl)aminocarbonyl)phenylsulfonyl)amino)carbonyl]-pyridine-2-carboxylate

EXAMPLE 191

2-Propyl 5-[((4-((2-(4-chlorophenyl)ethyl)aminocarbonyl)phenylsulfonyl)amino)carbonyl]-pyridine-2-carboxylate

EXAMPLE 192

2-Propyl 5-[((4-(ethylaminocarbonyl)phenylsulfonyl)amino)carbonyl]-pyridine-2-carboxylate

EXAMPLE 193

2-Propyl 5-[((4-(n-butylaminocarbonyl)phenylsulfonyl)amino)carbonyl]-pyridine-2-carboxylate

EXAMPLE 194

2-Propyl 5-[((4-(n-hexylaminocarbonyl)phenylsulfonyl)amino)carbonyl]-pyridine-2-carboxylate

EXAMPLE 195

2-Propyl 5-[((4-(N,N-di-n-butylaminocarbonyl)phenylsulfonyl)amino)carbonyl]-pyridine-2-carboxylate

EXAMPLE 196

2-Propyl 5-[((4-(cyclohexylaminocarbonyl)phenylsulfonyl)amino)carbonyl]-pyridine-2-carboxylate

EXAMPLE 197

2-Propyl 5-[((4-((2-methoxyethyl)aminocarbonyl)phenylsulfonyl)amino)carbonyl]-pyridine-2-carboxylate

EXAMPLE 198

2-Propyl 5-[((4-((3-ethoxypropyl)aminocarbonyl)phenylsulfonyl)amino)carbonyl]-pyridine-2-carboxylate sodium salt a) 5-[((4-((3-ethoxypropyl)amino)carbonyl)phenylsulfonyl)amino)carbonyl]-pyridine-2-carboxylic acid 3.8 g (8.45 mmol) of the methyl ester described in Example 48 were introduced into 300 ml of 1.5N methanolic sodium hydroxide solution. A clear solution briefly formed. Crystalline material then precipitated. Stirring was continued for 30 minutes, the mixture was concentrated in vacuo, the residue was heated in 250 ml of water on a steam bath, 100 ml of 1,4-dioxane were added to the solution, while hot, the undissolved substance was filtered off hot, the filtrate was acidified to pH 1 with concentrated aqueous HCl and concentrated in vacuo and the product which had precipitated was filtered off with suction, washed with water and dried: 3.3 g of product; melting point 192° to 194° C.

b) 4 drops of concentrated $H_2SO_4$ were added to 1 g (2.30 mmol) of the above pyridine-2-carboxylic acid in 50 ml of 2-propanol and the mixture was heated at 80° C. for 8 hours, while stirring. It was concentrated in vacuo, the oil residue was treated with 80 ml of saturated aqueous $NaHCO_3$ solution, an unidentified solid was separated off, the $NaHCO_3$ phase was acidified to pH 1 with aqueous HCl and the precipitate was filtered off with suction and washed with water. The substance was dissolved in methylene chloride and, after treatment with aqueous $NaHCO_3$ solution, the title compound was isolated in the form of colorless crystals. This gave 0.15 g; melting point 145° C.

EXAMPLE 199

2-Propyl 5-[((4-((3-methoxypropyl)aminocarbonyl)phenylsulfonyl)amino)carbonyl]-pyridine-2-carboxylate

EXAMPLE 200

2-Propyl 5-[((4-((2-phenylethyl)aminocarbonyl)phenylsulfonyl)amino)carbonyl]-pyridine-2-carboxylate

EXAMPLE 201

2-Propyl 5-[((4-((2-phenoxyethyl)aminocarbonyl)phenylsulfonyl)amino)carbonyl]-pyridine-2-carboxylate

EXAMPLE 202

Cyclohexyl 5-[((4-((2-phenylethyl)aminocarbonyl)phenylsulfonyl)amino)carbonyl]-pyridine-2-carboxylate

EXAMPLE 203

Cyclohexyl 5-[((4-(benzylaminocarbonyl)phenylsulfonyl)amino)carbonyl]-pyridine-2-carboxylate

EXAMPLE 204

Cyclohexyl 5-[((4-((3-phenylpropyl)aminocarbonyl)phenylsulfonyl)amino)carbonyl]-pyridine-2-carboxylate

EXAMPLE 205

Cyclohexyl 5-[((4-((4-phenyl-n-butyl)aminocarbonyl)phenylsulfonyl)amino)carbonyl]-pyridine-2-carboxylate

EXAMPLE 206

Cyclohexyl 5-[((4-((2-(4-methoxyphenyl)ethyl)aminocarbonyl)phenylsulfonyl)amino)carbonyl]-pyridine-2-carboxylate

EXAMPLE 207

Cyclohexyl 5-[((4-((2-(3-methoxyphenyl)ethyl)aminocarbonyl)phenylsulfonyl)amino)carbonyl]-pyridine-2-carboxylate

EXAMPLE 208

Cyclohexyl 5-[((4-((2-(2-methoxyphenyl)ethyl)aminocarbonyl)phenylsulfonyl)amino)carbonyl]-pyridine-2-carboxylate

EXAMPLE 209

2-Cyclohexyl 5-[((4-((2-(4-fluorophenyl)ethyl)aminocarbonyl)phenylsulfonyl)amino)carbonyl]-pyridine-2-carboxylate

EXAMPLE 210

Cyclohexyl 5-[((4-((2-(4-chlorophenyl)ethyl)aminocarbonyl)phenylsulfonyl)amino)carbonyl]-pyridine-2-carboxylate

EXAMPLE 211

Cyclohexyl 5-[((4-(ethylaminocarbonyl)phenylsulfonyl)amino)carbonyl]-pyridine-2-carboxylate

EXAMPLE 212

Cyclohexyl 5-[((4-(n-butylaminocarbonyl)phenylsulfonyl)amino)carbonyl]-pyridine-2-carboxylate

EXAMPLE 213

Cyclohexyl 5-[((4-(n-hexylaminocarbonyl)phenylsulfonyl)amino)carbonyl]-pyridine-2-carboxylate

EXAMPLE 214

Cyclohexyl 5-[((4-(N,N-di-n-butylaminocarbonyl)phenylsulfonyl)amino)carbonyl]-pyridine-2-carboxylate

EXAMPLE 215

Cyclohexyl 5-[((4-(cyclohexylaminocarbonyl)phenylsulfonyl)amino)carbonyl]-pyridine-2-carboxylate

EXAMPLE 216

Cyclohexyl 5-[((4-((2-methoxyethyl)aminocarbonyl)phenylsulfonyl)amino)carbonyl]-pyridine-2-carboxylate

EXAMPLE 217

Cyclohexyl 5-[((4-((2-ethoxyethyl)aminocarbonyl)phenylsulfonyl)amino)carbonyl]-pyridine-2-carboxylate

EXAMPLE 218

Cyclohexyl 5-[((4-((3-ethoxypropyl)aminocarbonyl)phenylsulfonyl)amino)carbonyl]-pyridine-2-carboxylate

EXAMPLE 219

Cyclohexyl 5-[((4-((2-phenoxyethyl)aminocarbonyl)phenylsulfonyl)amino)carbonyl]-pyridine-2-carboxylate

EXAMPLE 220

2-Propyl 5-[((3-(benzylaminocarbonyl)phenylsulfonyl)amino)carbonyl]-pyridine-2-carboxylate

EXAMPLE 221

2-Propyl 5-[((3-((3-phenylpropyl)aminocarbonyl)phenylsulfonyl)amino)carbonyl]-pyridine-2-carboxylate

EXAMPLE 222

2-Propyl 5-[((3-((4-phenyl-n-butyl)aminocarbonyl)phenylsulfonyl)amino)carbonyl]-pyridine-2-carboxylate

EXAMPLE 223

2-Propyl 5-[((3-((2-(4-methoxyphenyl)ethyl)aminocarbonyl)phenylsulfonyl)amino)carbonyl]-pyridine-2-carboxylate

EXAMPLE 224

2-Propyl 5-[((3-((2-(3-methoxyphenyl)ethyl)aminocarbonyl)phenylsulfonyl)amino)carbonyl]-pyridine-2-carboxylate

EXAMPLE 225

2-Propyl 5-[((3-((2-(2-methoxyphenyl)ethyl)aminocarbonyl)phenylsulfonyl)amino)carbonyl]-pyridine-2-carboxylate

EXAMPLE 226

2-Propyl 5-[((3-((2-(4-fluorophenyl)ethyl)aminocarbonyl)phenylsulfonyl)amino)carbonyl]-pyridine-2-carboxylate

EXAMPLE 227

2-Propyl 5-[((3-((2-(4-chlorophenyl)ethyl)aminocarbonyl)phenylsulfonyl)amino)carbonyl]-pyridine-2-carboxylate

EXAMPLE 228

2-Propyl 5-[((3-(ethylaminocarbonyl)phenylsulfonyl)amino)carbonyl]-pyridine-2-carboxylate

EXAMPLE 229

2-Propyl 5-[((3-(n-butylaminocarbonyl)phenylsulfonyl)amino)carbonyl]-pyridine-2-carboxylate

EXAMPLE 230

2-Propyl 5-[((3-(n-hexylaminocarbonyl)phenylsulfonyl)amino)carbonyl]-pyridine-2-carboxylate

EXAMPLE 231

2-Propyl 5-[((3-(N,N-di-n-butylaminocarbonyl)phenylsulfonyl)amino)carbonyl]-pyridine-2-carboxylate

EXAMPLE 232

2-Propyl 5-[((3-(cyclohexylaminocarbonyl)phenylsulfonyl)aminocarbonyl]-pyridine-2-carboxylate

EXAMPLE 233

2-Propyl 5-[((3-((2-methoxyethyl)aminocarbonyl)phenylsulfonyl)amino)carbonyl]-pyridine-2-carboxylate

EXAMPLE 234

2-Propyl 5-[((3-((2-ethoxyethyl)aminocarbonyl)phenylsulfonyl)amino)carbonyl]-pyridine-2-carboxylate

EXAMPLE 235

2-Propyl 5-[((3-((3-ethoxypropyl)aminocarbonyl)phenylsulfonyl)amino)carbonyl]-pyridine-2-carboxylate

EXAMPLE 236

2-Propyl 5-[((3-((2-phenylethyl)aminocarbonyl)phenylsulfonyl)amino)carbonyl]-pyridine-2-carboxylate

EXAMPLE 237

2-Propyl 5-[((3-((2-phenoxyethyl)aminocarbonyl)phenylsulfonyl)amino)carbonyl]-pyridine-2-carboxylate

EXAMPLE 238

4-Heptyl 5-[((4-(benzylaminocarbonyl)phenylsulfonyl)amino)carbonyl]-pyridine-2-carboxylate

EXAMPLE 239

4-Heptyl 5-[((4-((3-phenylpropyl)aminocarbonyl)phenylsulfonyl)amino)carbonyl]-pyridine-2-carboxylate

EXAMPLE 240

4-Heptyl 5-[((4-((4-phenyl-n-butyl)aminocarbonyl)phenylsulfonyl)amino)carbonyl]-pyridine-2-carboxylate

EXAMPLE 241

4-Heptyl 5-[((4-((2-(4-methoxyphenyl)ethyl)aminocarbonyl)phenylsulfonyl)amino)carbonyl]-pyridine-2-carboxylate

EXAMPLE 242

4-Heptyl 5-[((4-((2-(3-methoxyphenyl)ethyl)aminocarbonyl)phenylsulfonyl)amino)carbonyl]-pyridine-2-carboxylate

EXAMPLE 243

4-Heptyl 5-[((4-((2-(2-methoxyphenyl)ethyl)aminocarbonyl)phenylsulfonyl)amino)carbonyl]-pyridine-2-carboxylate

EXAMPLE 244

4-Heptyl 5-[((4-((2-(4-fluorophenyl)ethyl)aminocarbonyl)phenylsulfonyl)amino)carbonyl]-pyridine-2-carboxylate

EXAMPLE 245

4-Heptyl 5-[((4-((2-(4-chlorophenyl)ethyl)aminocarbonyl)phenylsulfonyl)amino)carbonyl]-pyridine-2-carboxylate

EXAMPLE 246

4-Heptyl 5-[((4-(ethylaminocarbonyl)phenylsulfonyl)amino)carbonyl]-pyridine-2-carboxylate

EXAMPLE 247

4-Heptyl 5-[((4-(n-butylaminocarbonyl)phenylsulfonyl)amino)carbonyl]-pyridine-2-carboxylate

EXAMPLE 248

4-Heptyl 5-[((4-(n-hexylaminocarbonyl)phenylsulfonyl)amino)carbonyl]-pyridine-2-carboxylate

EXAMPLE 249

4-Heptyl 5-[((4-(N,N-di-n-butylaminocarbonyl)phenylsulfonyl)amino)carbonyl]-pyridine-2-carboxylate

EXAMPLE 250

4-Heptyl 5-[((4-(cyclohexylaminocarbonyl)phenylsulfonyl)amino)carbonyl]-pyridine-2-carboxylate

EXAMPLE 251

4-Heptyl 5-[((4-((2-methoxyethyl)aminocarbonyl)phenylsulfonyl)amino)carbonyl]-pyridine-2-carboxylate

EXAMPLE 252

4-Heptyl 5-[((4-((2-ethoxyethyl)aminocarbonyl)phenylsulfonyl)amino)carbonyl]-pyridine-2-carboxylate

EXAMPLE 253

4-Heptyl 5-[((4-((3-ethoxypropyl)aminocarbonyl)phenylsulfonyl)amino)carbonyl]-pyridine-2-carboxylate

EXAMPLE 254

4-Heptyl 5-[((4-((2-phenylethyl)aminocarbonyl)phenylsulfonyl)amino)carbonyl]-pyridine-2-carboxylate

EXAMPLE 255

4-Heptyl 5-[((4-((2-phenoxyethyl)aminocarbonyl)phenylsulfonyl)amino)carbonyl]-pyridine-2-carboxylate

EXAMPLE 256

2-(2-Methylpropyl) 5-[((4-(benzylaminocarbonyl)phenylsulfonyl)amino)carbonyl]-pyridine-2-carboxylate

EXAMPLE 257

2-(2-Methylpropyl) 5-[((4-((3-phenylpropyl)aminocarbonyl)phenylsulfonyl)amino)carbonyl]-pyridine-2-carboxylate

EXAMPLE 258

2-(2-Methylpropyl) 5-[((4-((4-phenyl-n-butyl)aminocarbonyl)phenylsulfonyl)amino)carbonyl]-pyridine-2-carboxylate

EXAMPLE 259

2-(2-Methylpropyl) 5-[((4-((2-(4-methoxyphenyl)ethyl)aminocarbonyl)phenylsulfonyl)amino)carbonyl]-pyridine-2-carboxylate

EXAMPLE 260

2-(2-Methylpropyl) 5-[((4-((2-(3-methoxyphenyl)ethyl)aminocarbonyl)phenylsulfonyl)amino)carbonyl]-pyridine-2-carboxylate

EXAMPLE 261

2-(2-Methylpropyl) 5-[((4-((2-(2-methoxyphenyl)ethyl)aminocarbonyl)phenylsulfonyl)amino)carbonyl]-pyridine-2-carboxylate

EXAMPLE 262

2-(2-Methylpropyl) 5-[((4-((2(4-fluorophenyl)ethyl)aminocarbonyl)phenylsulfonyl)amino)carbonyl]-pyridine-2-carboxylate

EXAMPLE 263

2-(2-Methylpropyl) 5-[((4-((2-(4-chlorophenyl)ethyl)aminocarbonyl)phenylsulfonyl)amino)carbonyl]-pyridine-2-carboxylate

EXAMPLE 264

2-(2-Methylpropyl) 5-[((4-(ethylaminocarbonyl)phenylsulfonyl)amino)carbonyl]-pyridine-2-carboxylate

EXAMPLE 265

1-(2-Methylpropyl) 5-[((4-(n-butylaminocarbonyl)phenylsulfonyl)amino)carbonyl]-pyridine-2-carboxylate

EXAMPLE 266

1-(2-Methylpropyl) 5-[((4-(n-hexylaminocarbonyl)phenylsulfonyl)amino)carbonyl]-pyridine-2-carboxylate

EXAMPLE 267

1-(2-Methylpropyl) 5-[((4-(N,N-di-n-butylaminocarbonyl)phenylsulfonyl)amino)carbonyl]-pyridine-2-carboxylate

EXAMPLE 268

1-(2-Methylpropyl) 5-[((4-(cyclohexylaminocarbonyl)phenylsulfonyl)amino)carbonyl]-pyridine-2-carboxylate

EXAMPLE 269

1-(2-Methylpropyl) 5-[((4-methoxyethyl)aminocarbonyl)phenylsulfonyl)amino)carbonyl]-pyridine-2-carboxylate

EXAMPLE 270

1-(2-Methylpropyl) 5-[((4-((2-ethoxyethyl)aminocarbonyl)phenylsulfonyl)amino)carbonyl]-pyridine-2-carboxylate

EXAMPLE 271

1-(2-Methylpropyl) 5-[((4(3-(ethoxypropyl)aminocarbonyl)phenylsulfonyl)amino)carbonyl]-pyridine-2-carboxylate

EXAMPLE 272

1-(2-Methylpropyl) 5-[((4-((2-phenylethyl)aminocarbonyl)phenylsulfonyl)amino)carbonyl]-pyridine-2-carboxylate

EXAMPLE 273

1-(2-Methylpropyl) 5-[((4-((2-phenoxyethyl)aminocarbonyl)phenylsulfonyl)amino)carbonyl]-pyridine-2-carboxylate

EXAMPLE 274

3-(2,5-Dimethylpentyl) 5-[((4-benzylaminocarbonyl)-phenylsulfonyl)amino)carbonyl]-pyridine-2-carboxylate

EXAMPLE 275

3-(2,5-Dimethylpentyl) 5-[((4-((3-phenylpropyl)aminocarbonyl)phenylsulfonyl)amino)carbonyl]-pyridine-2-carboxylate

EXAMPLE 276

3-(2,5-Dimethylpentyl) 5-[((4-((4-phenyl-n-butyl)aminocarbonyl)phenylsulfonyl)amino)carbonyl]-pyridine-2-carboxylate

EXAMPLE 277

3-(2,5-Dimethylpentyl) 5-[((4-((2-)4-methoxyphenyl)ethyl)aminocarbonyl)phenylsulfonyl)amino)carbonyl]-pyridine-2-carboxylate

EXAMPLE 278

3-(2,5-Dimethylpentyl) 5-[((4-((2-(3-methoxyphenyl)ethyl)aminocarbonyl)phenylsulfonyl)amino)carbonyl]-pyridine-2-carboxylate

EXAMPLE 279

3-(2,5-Dimethylpentyl) 5-[((4-((2-(2-methoxyphenyl)ethyl)aminocarbonyl)phenylsulfonyl)amino)carbonyl]-pyridine-2-carboxylate

EXAMPLE 280

3-(2,5-Dimethylpentyl) 5-[((4-((2-(4-fluorophenyl)ethyl)aminocarbonyl)phenylsulfonyl)amino)carbonyl]-pyridine-2-carboxylate

EXAMPLE 281

3-(2,5-Dimethylpentyl) 5-[((4-((2-(4-chlorophenyl)ethyl)aminocarbonyl)phenylsulfonyl)amino)carbonyl]-pyridine-2-carboxylate

EXAMPLE 282

3-(2,5-Dimethylpentyl) 5-[((4-(ethylaminocarbonyl)phenylsulfonyl)amino)carbonyl]-pyridine-2-carboxylate

EXAMPLE 283

3-(2,5-Dimethylpentyl) 5-[((4-(n-butylaminocarbonyl)phenylsulfonyl)amino)carbonyl]-pyridine-2-carboxylate

EXAMPLE 284

3-(2,5-Dimethylpentyl) 5-[((4-(n-hexylaminocarbonyl)phenylsulfonyl)amino)carbonyl]-pyridine-2-carboxylate

EXAMPLE 285

3-(2,5-Dimethylpentyl) 5-[((4-(N,N-di-n-butylaminocarbonyl)phenylsulfonyl)amino)carbonyl]-pyridine-2-carboxylate

EXAMPLE 286

3-(2,5-Dimethylpentyl) 5-[((4-(cyclohexylaminocarbonyl)phenylsulfonyl)amino)carbonyl]-pyridine-2-carboxylate

EXAMPLE 287

3-(2,5-Dimethylpentyl) 5-[((4-((2-methoxyethyl)aminocarbonyl)phensylfonyl)amino)carbonyl]-pyridine-2-carboxylate

EXAMPLE 288

3-(2,5-Dimethylpentyl) 5-[((4-((2-ethoxyethyl)aminocarbonyl)phenylsulfonyl)amino)carbonyl]-pyridine-2-carboxylate

EXAMPLE 289

3-(2,5-Dimethylpentyl) 5-[((4-((3-ethoxypropyl)aminocarbonyl)phenylsulfonyl)amino)carbonyl]-pyridine-2-carboxylate

EXAMPLE 290

3-(2,5-Dimethylpentyl) 5-[((4-((2-phenylethyl)aminocarbonyl)phenylsulfonyl)amino)carbonyl]-pyridine-2-carboxylate

EXAMPLE 291

Benzyl 5-[((4-((2-phenoxyethyl)aminocarbonyl)phenylsulfonyl)amino)carbonyl]-pyridine-2-carboxylate

EXAMPLE 292

Benzyl 5-[((4-(benzylaminocarbonyl)phenylsulfonyl)amino)carbonyl]-pyridine-2-carboxylate

EXAMPLE 293

Benzyl 5-[((4-((3-phenylpropyl)aminocarbonyl)phenylsulfonyl)amino)carbonyl]-pyridine-2-carboxylate

EXAMPLE 294

Benzyl 5-[((4-((4-phenyl-n-butyl)aminocarbonyl)-phenylsulfonyl)amino)carbonyl]-pyridine-2-carboxylate

EXAMPLE 295

Benzyl 5-[((4-((2-(4-methoxyphenyl)ethyl)aminocarbonyl)phenylsulfonyl)amino)carbonyl]-pyridine-2-carboxylate

EXAMPLE 296

Benzyl 5-[((4-((2-(3-methoxyphenyl)ethyl)aminocarbonyl)phenylsulfonyl)amino)carbonyl]-pyridine-2-carboxylate

EXAMPLE 297

Benzyl 5-[((4-((2-(2-methoxyphenyl)ethyl)aminocarbonyl)phenylsulfonyl)amino)carbonyl]-pyridine-2-carboxylate

EXAMPLE 298

2-Benzyl 5-[((4-((2-(4-fluorophenyl)ethyl)aminocarbonyl)phenylsulfonyl)amino)carbonyl]-pyridine-2-carboxylate

EXAMPLE 299

Benzyl 5-[((4-((2-(4-chlorophenyl)ethyl)aminocarbonyl)phenylsulfonyl)amino)carbonyl]-pyridine-2-carboxylate

EXAMPLE 300

Benzyl 5-[((4-(ethylaminocarbonyl)phenylsulfonyl)amino)carbonyl]-pyridine-2-carboxylate

EXAMPLE 301

Cyclopentyl 5-[((4-(n-butylaminocarbonyl)phenylsulfonyl)amino)carbonyl]-pyridine-2-carboxylate

EXAMPLE 302

Cyclopentyl 5-[((4-(n-hexylaminocarbonyl)phenylsulfonyl)amino)carbonyl]-pyridine-2-carboxylate

EXAMPLE 303

Cyclopentyl 5-[((4-(N,N-di-n-butylaminocarbonyl)phenylsulfonyl)amino)carbonyl]-pyridine-2-carboxylate

EXAMPLE 304

Cyclopentyl 5-[((4-(cyclohexylaminocarbonyl)phenylsulfonyl)amino)carbonyl]-pyridine-2-carboxylate

EXAMPLE 305

Cyclopentyl 5-[((4-((2-methoxyethyl)aminocarbonyl)phenylsulfonyl)amino)carbonyl]-pyridine-2-carboxylate

EXAMPLE 306

Cyclopentyl 5-[((4-((2-ethoxyethyl)aminocarbonyl)phenylsulfonyl)amino)carbonyl]-pyridine-2-carboxylate

EXAMPLE 307

Cyclopentyl 5-[((4-((3-ethoxypropyl)aminocarbonyl)phenylsulfonyl)amino)carbonyl]-pyridine-2-carboxylate

EXAMPLE 308

Cyclopentyl 5-[((4-((2-phenylethyl)aminocarbonyl)phenylsulfonyl)amino)carbonyl]-pyridine-2-carboxylate

EXAMPLE 309

Cyclopentyl 5-[((4-((2-phenoxyethyl)aminocarbonyl)phenylsulfonyl)amino)carbonyl]-pyridine-2-carboxylate

EXAMPLE 310

Methyl 5-[((2-chloro-4-((2-phenylethyl)aminocarbonyl)phenylsulfonyl)amino)carbonyl]-pyridine-2-carboxylate Na salt Melting point 258° to 260° C. (from ethyl acetate)

EXAMPLE 311

Methyl 5-[((2-chloro-4-((3-ethoxypropyl)aminocarbonyl)phenylsulfonyl)amino)carbonyl]-pyridine-2-carboxylate Melting point 164° to 166° (from diethyl ether)

EXAMPLE 312

Methyl 5-[((4-chloro-3-((3-ethoxypropyl)aminocarbonyl)phenylsulfonyl)amino)carbonyl]-pyridine-2-carboxylate

EXAMPLE 313

Methyl 5-[((4-chloro-3-((2-phenoxyethyl)aminocarbonyl)phenylsulfonyl)amino)carbonyl]-pyridine-2-carboxylate

EXAMPLE 314

2-Propyl 5-[((2-chloro-4-((2-phenylethyl)aminocarbonyl)phenylsulfonyl)amino)carbonyl]-pyridine-2-carboxylate

EXAMPLE 315

2-Propyl 5-[((2-chloro-4-((3-ethoxypropyl)aminocarbonyl)phenylsulfonyl)amino)carbonyl]-pyridine-2-carboxylate

EXAMPLE 316

2-Propyl 5-[((4-chloro-3-((3-ethoxypropyl)aminocarbonyl)phenylsulfonyl)amino)carbonyl]-pyridine-2-carboxylate

EXAMPLE 317

2-Propyl 5-[((4-chloro-3-((2-phenoxyethyl)aminocarbonyl)phenylsulfonyl)amino)carbonyl]-pyridine-2-carboxylate

EXAMPLE 318

2-(Methylbutyl) 5-[((2-chloro-4-((2-phenylethyl)aminocarbonyl)phenylsulfonyl)amino)carbonyl]-pyridine-2-carboxylate

EXAMPLE 319

2-(2-Methylbutyl) 5-[((2-chloro-4-((3-ethoxypropyl)aminocarbonyl)phenylsulfonyl)amino)carbonyl]-pyridine-2-carboxylate

EXAMPLE 320

2-(2-Methylbutyl) 5-[((4-chloro-3-((3-ethoxypropyl)aminocarbonyl)phenylsulfonyl)amino)carbonyl]-pyridine-2-carboxylate

EXAMPLE 321

2-(2-Methylbutyl) 5-[((4-chloro-3-((2-phenylethyl)aminocarbonyl)phenylsulfonyl)amino)carbonyl]-pyridine-2-carboxylate

EXAMPLE 322

2-(2-Methylhexyl) 5-[((2-chloro-4-((2-phenoxyethyl)aminocarbonyl)phenylsulfonyl)amino)carbonyl]-pyridine-2-carboxylate

EXAMPLE 323

2-(2-Methylhexyl) 5-[((2-chloro-4-((3-ethoxypropyl)aminocarbonyl)phenylsulfonyl)amino)carbonyl]-pyridine-2-carboxylate

EXAMPLE 324

2-(2-Methylhexyl) 5-[((2-chloro-4-((2-phenoxyethyl)aminocarbonyl)phenylsulfonyl)amino)carbonyl]-pyridine-2-carboxylate

EXAMPLE 325

2-(2-Methylhexyl) 5-[((2-chloro-4-((3-ethoxypropyl)aminocarbonyl)phenylsulfonyl)amino)carbonyl]-pyridine-2-carboxylate

EXAMPLE 326

Cyclohexyl 5-[((4-chloro-3-((3-ethoxypropyl)aminocarbonyl)phenylsulfonyl)amino)carbonyl]-pyridine-2-carboxylate

EXAMPLE 327
Cyclohexyl 5-[((4-chloro-3-((2-phenoxyethyl)aminocarbonyl)phenylsulfonyl)amino)carbonyl]-pyridine-2-carboxylate

EXAMPLE 328
Cyclohexyl 5-[((2-chloro-4-((2-phenylethyl)aminocarbonyl)phenylsulfonyl)amino)carbonyl]-pyridine-2-carboxylate

EXAMPLE 329
Cyclohexyl 5-[((2-chloro-4-((3-ethoxypropyl)aminocarbonyl)phenylsulfonyl)amino)carbonyl]-pyridine-2-carboxylate

EXAMPLE 330
(Methylcyclohexyl) 5-[((2-chloro-4-((2-phenylethyl)aminocarbonyl)phenylsulfonyl)amino)carbonyl]-pyridine-2-carboxylate

EXAMPLE 331
(Methylcyclohexyl) 5-[((2-chloro-4-((3-ethoxypropyl)aminocarbonyl)phenylsulfonyl)amino)carbonyl]-pyridine-2-carboxylate

EXAMPLE 332
Ethyl 5-[((4-(2-((2-chloro-5-methoxybenzoyl)amino)ethyl)phenylsulfonyl)amino)carbonyl]-pyridine-2-carboxylate

EXAMPLE 333
Ethyl 5-[((4-(2-(acetylamino)ethyl)phenylsulfonyl)amino)carbonyl]-pyridine-2-carboxylate (Method B)
Melting point 245° C. (from aqueous hydrochloric acid)

EXAMPLE 334
Ethyl 5-[((4-(2-(n-butanoylamino)ethyl)phenylsulfonyl)amino)carbonyl]-pyridine-2-carboxylate

EXAMPLE 335
Ethyl 5-[((4-(2-(benzoylamino)ethyl)phenylsulfonyl)amino)carbonyl]-pyridine-2-carboxylate

EXAMPLE 336
Ethyl 5-[((4-(2-((4-chlorobenzoyl)amino)ethyl)phenylsulfonyl)amino)carbonyl]-pyridine-2-carboxylate

EXAMPLE 337
Ethyl 5-[((4-(2-((5-chloro-2-methoxybenzoyl)amino)ethyl)phenylsulfonyl)amino)carbonyl]-pyridine-2-carboxylate

EXAMPLE 338
Ethyl 5-[((4-(2-((3-phenyl-n-propionyl)amino)ethyl)phenylsulfonyl)amino)carbonyl]-pyridine-2-carboxylate

EXAMPLE 339
Ethyl 5-[((4-(2-((2-phenylacetyl)amino)ethyl)phenylsulfonyl)amino)carbonyl]-pyridine-2-carboxylate

EXAMPLE 340
Ethyl 5-[((4-(2-((phenoxyacetyl)amino)ethyl)phenylsulfonyl)amino)carbonyl]-pyridine-2-carboxylate

EXAMPLE 341
Ethyl 5-[((4-(2-((4-fluorobenzoyl)amino)ethyl)phenylsulfonyl)amino)carbonyl]-pyridine-2-carboxylate

EXAMPLE 342
Ethyl 5-[((4-(2-((4-ethoxybenzoyl)amino)ethyl)phenylsulfonyl)amino)carbonyl]-pyridine-2-carboxylate

EXAMPLE 343
Ethyl 5-[((4-(2-((cyclohexanoyl)amino)ethyl)phenylsulfonyl)amino)carbonyl]-pyridine-2-carboxylate

EXAMPLE 344
Ethyl 5-[((4-(2-((cyclohexylacetyl)amino)ethyl)phenylsulfonyl)amino)carbonyl]-pyridine-2-carboxylate

EXAMPLE 345
Ethyl 5-[((4-(2-((2-methylpropionyl)amino)ethyl)phenylsulfonyl)amino)carbonyl]-pyridine-2-carboxylate

EXAMPLE 346
Methyl 5-[((3-(2-((2-chloro-5-methoxybenzoyl)ethyl)phenylsulfonyl)amino)carbonyl]-pyridine-2-carboxylate

EXAMPLE 347
Methyl 5-[((3-(2-(acetylamino)ethyl)phenylsulfonyl)amino)carbonyl]-pyridine-2-carboxylate

EXAMPLE 348
Methyl 5-[((3-(2-(n-butanoylamino)ethyl)phenylsulfonyl)amino)carbonyl]-pyridine-2-carboxylate

EXAMPLE 349
Methyl 5-[((3-(2-(benzoylamino)ethyl)phenylsulfonyl)amino)carbonyl]-pyridine-2-carboxylate

EXAMPLE 350
Methyl 5-[((3-(2-((4-chlorobenzoyl)amino)ethyl)phenylsulfonyl)amino)carbonyl]-2-carboxylate

EXAMPLE 351
Methyl 5-[((3-(2-((5-chloro-2-methoxybenzoyl)amino)ethyl)phenylsulfonyl)amino)carbonyl]-pyridine-2-carboxylate

EXAMPLE 352
Methyl 5-[((3-(2-((3-phenyl-n-propionyl)amino)ethyl)phenylsulfonyl)amino)carbonyl]-pyridine-2-carboxylate

EXAMPLE 353
Methyl 5-[((3-(2-((2-phenylacetyl)amino)ethyl)phenylsulfonyl)amino)carbonyl]-pyridine-2-carboxylate

EXAMPLE 354
Methyl 5-[((3-(2-((phenoxyacetyl)amino)ethyl)phenylsulfonyl)amino)carbonyl]-pyridine-2-carboxylate

EXAMPLE 355
Methyl 5-[((3-(2-((4-fluorobenzoyl)amino)ethyl)phenylsulfonyl)amino)carbonyl]-pyridine-2-carboxylate

EXAMPLE 356

Methyl 5-[((3-(2-((4-ethoxybenzoyl)amino)ethyl)-phenylsulfonyl)amino)carbonyl]-pyridine-2-carboxylate

EXAMPLE 357

Methyl 5-[((3-(2-((cyclohexanoyl)amino)ethyl)phenylsulfonyl)amino)carbonyl]-pyridine-2-carboxylate

EXAMPLE 358

Methyl 5-[((3-(2-((cyclohexylacetyl)amino)ethyl)-phenylsulfonyl)amino)carbonyl]-pyridine-2-carboxylate

EXAMPLE 359

Methyl 5-[((3-(2-((2-methylpropionyl)amino)ethyl)-phenylsulfonyl)amino)carbonyl]-pyridine-2-carboxylate

EXAMPLE 360

2-Propyl 5-[((4-(2-((2-chloro-5-methoxybenzoyl)amino)ethyl)phenylsulfonyl)amino)carbonyl]-pyridine-2-carboxylate

EXAMPLE 361

2-Propyl 5-[((4-(2-(acetylamino)ethyl)phenylsulfonyl)amino)carbonyl]-pyridine-2-carboxylate

EXAMPLE 362

2-Propyl 5-[((4-(2-(n-butanoylamino)ethyl)phenylsulfonyl)amino)carbonyl]-pyridine-2-carboxylate

EXAMPLE 363

2-Propyl 5-[((4-(2-benzoylamino)ethyl)phenylsulfonyl)amino)carbonyl]-pyridine-2-carboxylate

EXAMPLE 364

2-Propyl 5-[((4-((4-chlorobenzoyl)amino)ethyl)phenylsulfonyl)amino)carbonyl]-pyridine-2-carboxylate

EXAMPLE 365

2-Propyl 5-[((4-(2-((5-chloro-2-methoxybenzoyl)amino)ethyl)phenylsulfonyl)amino)carbonyl]-pyridine-2-carboxylate

EXAMPLE 366

2-Propyl 5-[((4-(2-((3-phenyl-n-propionyl)amino)ethyl)-phenylsulfonyl)amino)carbonyl]-pyridine-2-carboxylate

EXAMPLE 367

2-Propyl 5-[((4-(2-((2-phenylacetyl)amino)ethyl)-phenylsulfonyl)amino)carbonyl]-pyridine-2-carboxylate

EXAMPLE 368

2-Propyl 5-[((4-(2-((phenoxyacetyl)amino)ethyl)-phenylsulfonyl)amino)carbonyl]-pyridine-2-carboxylate

EXAMPLE 369

2-Propyl 5-[((4-(2-((4-fluorobenzoyl)amino)ethyl)-phenylsulfonyl)amino)carbonyl]-pyridine-2-carboxylate

EXAMPLE 370

2-Propyl 5-[((4-(2-((4-ethoxybenzoyl)amino)ethyl)-phenylsulfonyl)amino)carbonyl]-pyridine-2-carboxylate

EXAMPLE 371

2-Propyl 5-[((4-(2-((cyclohexanoyl)amino)ethyl)phenylsulfonyl)amino)carbonyl]-pyridine-2-carboxylate

EXAMPLE 372

2-Propyl 5-[((4-(2-(cyclohexylacetyl)amino)ethyl)-phenylsulfonyl)amino)carbonyl]-pyridine-2-carboxylate

EXAMPLE 373

2-Propyl 5-[((4-(2-((2-methylpropionyl)amino)ethyl)-phenylsulfonyl)amino)carbonyl]-pyridine-2-carboxylate

EXAMPLE 374

3-Pentyl 5-[((4-(2-((2-chloro-5-methoxybenzoyl)amino)ethyl)phenylsulfonyl)amino)carbonyl]-pyridine-2-carboxylate a) 5-[((4-(2-((2-Chloro-5-methoxybenzoyl)amino)ethyl)-phenylsulfonyl)amino)carbonyl]-pyridine-2-carboxylate 0.8 g (1.36 mmol) of the methyl ester from Example 68 was hydrolyzed with 30 ml 1N methanolic NaOH analogously to Example 112 a). After the mixture had been concentrated in vacuo, the residue was dissolved in tetrahydrofuran, the solution was acidified with 2N aqueous HCl and concentrated and the residue was treated with water and filtered off with suction. 0.75 g of product was isolated, melting point 149° C. (decomposition)

b) The title compound was obtained analogously to Example 2c). 4 drops of concentrated $H_2SO_4$ were added to 1.04 g (2 mmol) of the above pyridine-2-carboxylic acid in 40 ml of 3-pentanol and the mixture was heated at 80° C. for 24 hours, while stirring. It was concentrated in vacuo and the resinous residue was crystallized with acetone to give 0.32 g of crude product; melting point 174° to 176° C. The mother liquor was concentrated, the residue was dissolved in methylene chloride and the solution was shaken with saturated aqueous $NaHCO_3$ solution. The organic phase was dried and the Na salt of the product was crystallized with acetone. This salt was suspended in tetrahydrofuran, the suspension was acidified with aqueous HCl, the clear solution formed was combined with the crystalline crude product, the mixture was concentrated and the residue was crystallized with ethyl acetate. This gave 0.54 g of colorless product; melting point 164° to 166° C.

EXAMPLE 375

3-Pentyl 5-[((3-(2-(acetylamino)ethyl)phenylsulfonyl)amino)carbonyl]-pyridine-2-carboxylate

EXAMPLE 376

3-Pentyl 5-[((3-(2-(n-butanoylamino)ethyl)phenylsulfonyl)amino)carbonyl]-pyridine-2-carboxylate

EXAMPLE 377

3-Pentyl 5-[((3-(2-(benzoylamino)ethyl)phenylsulfonyl)amino)carbonyl]-pyridine-2-carboxylate

EXAMPLE 378

3-Pentyl 5-[((3-(2-((4-chlorobenzoyl)amino)ethyl)-phenylsulfonyl)amino)carbonyl]-pyridine-2-carboxylate

EXAMPLE 379

3-Pentyl 5-[((3-(2-((5-chloro-2-methoxybenzoyl)amino)ethyl)phenylsulfonyl)amino)carbonyl]-pyridine-2-carboxylate

EXAMPLE 380

3-Pentyl 5-[((3-(2-((3-phenyl-n-propionyl)amino)ethyl)-phenylsulfonyl)amino)carbonyl]-pyridine-2-carboxylate

EXAMPLE 381

3-Pentyl 5-[((3-(2-((2-phenylacetyl)amino)ethyl)phenyl-sulfonyl)amino)carbonyl]-pyridine-2-carboxylate

EXAMPLE 382

3-Pentyl 5-[((3-(2-((phenoxyacetyl)amino)ethyl)phenyl-sulfonyl)amino)carbonyl]-pyridine-2-carboxylate

EXAMPLE 383

3-Pentyl 5-[((3-(2-((4-fluorobenzoyl)amino)ethyl)-phenylsulfonyl)amino)carbonyl]-pyridine-2-carboxylate

EXAMPLE 384

3-Pentyl 5-[((3-(2-((4-ethoxybenzoyl)amino)ethyl)-phenylsulfonyl)amino)carbonyl]-pyridine-2-carboxylate

EXAMPLE 385

3-Pentyl 5-[((3-(2-((cyclohexanoyl)amino)ethyl)phenyl-sulfonyl)amino)carbonyl]-pyridine-2-carboxylate

EXAMPLE 386

3-Pentyl 5-[((3-(2-((cyclohexylacetyl)amino)ethyl)-phenylsulfonyl)amino)carbonyl]-pyridine-2-carboxylate

EXAMPLE 387

3-Pentyl 5-[((3-(2-((2-methylpropionyl)amino)ethyl)-phenylsulfonyl)amino)carbonyl]-pyridine-2-carboxylate

EXAMPLE 388

3-Pentyl 5-[((4-(2-((2-chloro-5-methoxybenzoyl)amino)ethyl)phenylsulfonyl)amino)carbonyl]-pyridine-2-carboxylate

EXAMPLE 389

3-Pentyl 5-[((4-(2-(acetylamino)ethyl)phenylsulfonyl)amino)carbonyl]-pyridine-2-carboxylate

EXAMPLE 390

3-Pentyl 5-[((4-(2-(n-butanoylamino)ethyl)phenylsulfonyl)amino)carbonyl]-pyridine-2-carboxylate

EXAMPLE 391

3-Pentyl 5-[((4-(2-(benzoylamino)ethyl)phenylsulfonyl)amino)carbonyl]-pyridine-2-carboxylate

EXAMPLE 392

3-Pentyl 5-[((4-(2-((4-chlorobenzoyl)amino)ethyl)-phenylsulfonyl)amino)carbonyl]-pyridine-2-carboxylate

EXAMPLE 393

3-Pentyl 5-[((4-(2-((5-chloro-2-methoxybenzoyl)amino)ethyl)phenylsulfonyl)amino)carbonyl]-pyridine-2-carboxylate

EXAMPLE 394

3-Pentyl 5-[((4-(2-((3-phenyl-n-propionyl)amino)ethyl)-phenylsulfonyl)amino)carbonyl]-pyridine-2-carboxylate

EXAMPLE 395

3-Pentyl 5-[((4-(2-(2-phenylacetyl)amino)ethyl)phenyl-sulfonyl)amino)carbonyl]-pyridine-2-carboxylate

EXAMPLE 396

3-Pentyl 5-[((4-(2-((phenoxyacetyl)amino)ethyl)-phenysulfonyl)amino)carbonyl]-pyridine-2-carboxylate

EXAMPLE 397

3-Pentyl 5-[((4-(2-((4-fluorobenzoyl)amino)ethyl)-phenylsulfonyl)amino)carbonyl]-pyridine-2-carboxylate

EXAMPLE 398

3-Pentyl 5[-((4-(2-((4-ethoxybenzoyl)amino)ethyl)-phenylsulfonyl)amino)carbonyl]-pyridine-2-carboxylate

EXAMPLE 399

3-Pentyl 5-[((4-(2-((cyclohexanoyl)amino)ethyl)phenyl-sulfonyl)amino)carbonyl]-pyridine-2-carboxylate

EXAMPLE 400

3-Pentyl 5-[((4-(2-((cyclohexylacetyl)amino)ethyl)-phenylsulfonyl)amino)carbonyl]-pyridine-2-carboxylate

EXAMPLE 401

3-Pentyl 5-[((4-(2-((2-methylpropionyl)amino)ethyl)-phenylsulfonyl)amino)carbonyl]-pyridine-2-carboxylate

EXAMPLE 402

2-(2-Methylhexyl) 5-[((4-(2-((2-chloro-5-methoxybenzoyl)amino)ethyl)phenylsulfonyl)amino)carbonyl]-pyridine-2-carboxylate

EXAMPLE 403

2-(2-Methylhexyl) 5-[((4-(2-(acetylamino)ethyl)phenyl-sulfonyl)amino)carbonyl]-pyridine-2-carboxylate

EXAMPLE 404

2-(2-Methylhexyl) 5-[((4-(2-(n-butanoylamino)ethyl)phenylsulfonyl)amino)carbonyl]-pyridine-2-carboxylate

EXAMPLE 405

2-(2-Methylhexyl) 5-[((4-(2-(benzoylamino)ethyl)-phenylsulfonyl)amino)carbonyl]-pyridine-2-carboxylate

EXAMPLE 406

2-(2-Methylhexyl) 5-[((4-(2-((4-chlorobenzoyl)amino)ethyl)phenylsulfonyl)amino)carbonyl]-pyridine-2-carboxylate

EXAMPLE 407

2-(2-Methylhexyl) 5-[((4-(2-((5-chloro-2-methoxybenzoyl)amino)ethyl)phenylsulfonyl)amino)carbonyl]-pyridine-2-carboxylate

EXAMPLE 408

2-(2-Methylhexyl) 5-[((4-(2-((3-phenyl-n-propionyl)amino)ethyl)phenylsulfonyl)amino)carbonyl]-pyridine-2-carboxylate

EXAMPLE 409

2-(2-Methylhexyl) 5-[((4-(2-((2-phenylacetyl)amino)ethyl)phenylsulfonyl)amino)carbonyl]-pyridine-2-carboxylate

EXAMPLE 410

2-(2-Methylhexyl) 5-[((4-(2-((phenoxyacetyl)amino)ethyl)phenylsulfonyl)amino)carbonyl]-pyridine-2-carboxylate

EXAMPLE 411

2-(2-Methylhexyl) 5-[((4-(2-((4-fluorobenzoyl)amino)ethyl)phenylsulfonyl)amino)carbonyl]-pyridine-2-carboxylate

EXAMPLE 412

2-(2-Methylhexyl) 5-[((4-(2-((4-ethoxybenzoyl)amino)ethyl)phenylsulfonyl)amino)carbonyl]-pyridine-2-carboxylate

EXAMPLE 413

2-(2-Methylhexyl) 5-[((4-(2-((cyclohexanoyl)amino)ethyl)phenylsulfonyl)amino)carbonyl]-pyridine-2-carboxylate

EXAMPLE 414

2-(2-Methylhexyl) 5-[((4-(2-((cyclohexylacetyl)amino)ethyl)phenylsulfonyl)amino)carbonyl]-pyridine-2-carboxylate

EXAMPLE 415

2-(2-Methylhexyl) 5-[((4-(2-((2-methylpropionyl)amino)ethyl)phenylsulfonyl)amino)carbonyl]-pyridine-2-carboxylate

EXAMPLE 416

2-(2-Methylbutyl) 5-[((4-(2-((2-chloro-5-methoxybenzoyl)amino)ethyl)phenylsulfonyl)amino)carbonyl]-pyridine-2-carboxylate

EXAMPLE 417

2-(2-Methylbutyl) 5-[((4-(2-(acetylamino)ethyl)phenylsulfonyl)amino)carbonyl]-pyridine-2-carboxylate

EXAMPLE 418

2-(2-Methylbutyl) 5-[((4-(2-(n-butanoylamino)ethyl)phenylsulfonyl)amino)carbonyl]-pyridine-2-carboxylate

EXAMPLE 419

2-(2-Methylbutyl) 5-[((4-(2-(benzoylamino)ethyl)phenylsulfonyl)amino)carbonyl]-pyridine-2-carboxylate

EXAMPLE 420

2-(2-Methylbutyl) 5-[((4-(2-((4-chlorobenzoyl)amino)ethyl)phenylsulfonyl)amino)carbonyl]-pyridine-2-carboxylate

EXAMPLE 421

2-(2-Methylbutyl) 5-[((4-(2-((5-chloro-2-methoxybenzoyl)amino)ethyl)phenylsulfonyl)amino)carbonyl]-pyridine-2-carboxylate

EXAMPLE 422

2-(2-Methylbutyl) 5-[((4-(2-((3-phenyl-n-propionyl)amino)ethyl)phenylsulfonyl)amino)carbonyl]-pyridine-2-carboxylate

EXAMPLE 423

3-(2,5-Dimethylpentyl) 5-[((4-(2-((2-phenylacetyl)amino)ethyl)phenylsulfonyl)amino)carbonyl]-pyridine-2-carboxylate

EXAMPLE 424

3-(2,5-Dimethylpentyl) 5-[((4-(2-((phenoxyacetyl)amino)ethyl)phenylsulfonyl)amino)carbonyl]-pyridine-2-carboxylate

EXAMPLE 425

3-(2,5-Dimethylpentyl) 5-[((4-(2-((4-fluorobenzoyl)amino)ethyl)phenylsulfonyl)amino)carbonyl]-pyridine-2-carboxylate

EXAMPLE 426

3-(2,5-Dimethylpentyl) 5-[((4-(2-((4-ethoxybenzoyl)amino)ethyl)phenylsulfonyl)amino)carbonyl]-pyridine-2-carboxylate

EXAMPLE 427

3-(2,5-Dimethylpentyl) 5-[((4-(2-((cyclohexanoyl)amino)ethyl)phenylsulfonyl)amino)carbonyl]-pyridine-2-carboxylate

EXAMPLE 428

3-(2,5-Dimethylpentyl) 5-[((4-(2-((cyclohexylacetyl)amino)ethyl)phenylsulfonyl)amino)carbonyl]-pyridine-2-carboxylate

EXAMPLE 429

3-(2,5-Dimethylpentyl) 5-[((4-(2-((2-methylpropionyl)amino)ethyl)phenylsulfonyl)amino)carbonyl]-pyridine-2-carboxylate

EXAMPLE 430

Methyl 5-[((4-(2-((2-ethylbutanoyl)amino)ethyl)phenylsulfonyl)amino)carbonyl]-pyridine-2-carboxylate
Melting point 186° C. (from ethyl acetate)

EXAMPLE 431

3-Pentyl 5-[((4-(2-((2-ethylbutanoyl)amino)ethyl)phenylsulfonyl)amino)carbonyl]-pyridine-2-carboxylate

EXAMPLE 432

2-(2-Methylpentyl) 5-[((4-(2-((4-n-butoxybenzoyl)amino)ethyl)phenylsulfonyl)amino)carbonyl]-pyridine-2-carboxylate

EXAMPLE 433

Benzyl 5-[((4-(2-((2-chloro-5-methoxybenzoyl)amino)ethyl)phenylsulfonyl)amino)carbonyl]-pyridine-2-carboxylate

EXAMPLE 434

Benzyl 5-[((4-(2-(acetylamino)ethyl)phenylsulfonyl)amino)carbonyl]-pyridine-2-carboxylate

EXAMPLE 435

Benzyl 5-[((4-(2-(n-butanoylamino)ethyl)phenylsulfonyl)amino)carbonyl]-pyridine-2-carboxylate

EXAMPLE 436

Benzyl 5-[((4-(2-(benzoylamino)ethyl)phenylsulfonyl)amino)carbonyl]-pyridine-2-carboxylate

EXAMPLE 437

Phenyl 5-[((4-(2-((4-chlorobenzoyl)amino)ethyl)phenylsulfonyl)amino)carbonyl]-pyridine-2-carboxylate

EXAMPLE 438

Phenyl 5-[((4-(2-((5-chloro-2-methoxybenzoyl)amino)ethyl)phenylsulfonyl)amino)carbonyl]-pyridine-2-carboxylate

EXAMPLE 439

Phenyl 5-[((4-(2-((3-phenyl-n-propionyl)amino)ethyl)phenylsulfonyl)amino)carbonyl]-pyridine-2-carboxylate

EXAMPLE 440

4-Methoxybenzyl 5-[((4-(2-((2-phenylacetyl)amino)ethyl)phenylsulfonyl)amino)carbonyl]-pyridine-2-carboxylate

EXAMPLE 441

4-Methoxybenzyl 5-[((4-(2-((phenoxyacetyl)amino)ethyl)phenylsulfonyl)amino)carbonyl]-pyridine-2-carboxylate

EXAMPLE 442

2-Methoxyethyl 5-[((4-(2-((4-fluorobenzoyl)amino)ethyl)phenylsulfonyl)amino)carbonyl]-pyridine-2-carboxylate

EXAMPLE 443

2-Methoxyethyl 5-[((4-(2-((4-ethoxybenzoyl)amino)ethyl)phenylsulfonyl)amino)carbonyl]-pyridine-2-carboxylate

EXAMPLE 444

2-Ethoxyethyl 5-[((4-(2-((cyclohexanoyl)amino)ethyl)phenylsulfonyl)amino)carbonyl]-pyridine-2-carboxylate

EXAMPLE 445

2-Ethoxyethyl 5-[((4-(2-((cyclohexylacetyl)amino)ethyl)phenylsulfonyl)amino)carbonyl]-pyridine-2-carboxylate

EXAMPLE 446

3-Methoxypropyl 5-[((4-(2-((2-methylpropionyl)amino)ethyl)phenylsulfonyl)amino)carbonyl]-pyridine-2-carboxylate

EXAMPLE 447

3-Hydroxypropyl 5-[((4-(2-(2-ethylbutanonyl)amino)ethyl)phenylsulfonyl)amino)carbonyl]-pyridine-2-carboxylate

EXAMPLE 448

(R)-2-Butyl 5-[((4-(2-((2-chloro-5-methoxybenzoyl)amino)ethyl)phenylsulfonyl)amino)carbonyl]-pyridine-2-carboxylate

EXAMPLE 449

(R)-2-Butyl 5-[((4-(2-(acetylamino)ethyl)phenylsulfonyl)amino)carbonyl]-pyridine-2-carboxylate

EXAMPLE 450

(R)-2-Butyl 5-[((4-(2-(n-butanoylamino)ethyl)phenylsulfonyl)amino)carbonyl]-pyridine-2-carboxylate

EXAMPLE 451

(R)-2-Butyl 5-[((4-(2-(benzoylamino)ethyl)phenylsulfonyl)amino)carbonyl]-pyridine-2-carboxylate

EXAMPLE 452

(R)-2-Butyl 5-[((4-(2-((4-chlorobenzoyl)amino)ethyl)phenylsulfonyl)amino)carbonyl]-pyridine-2-carboxylate

EXAMPLE 453

(R)-2-Butyl 5-[((4-(2-((5-chloro-2-methoxybenzoyl)amino)ethyl)phenylsulfonyl)amino)carbonyl]-pyridine-2-carboxylate

EXAMPLE 454

(R)-2-Butyl 5-[((4-(2-((3-phenyl-n-propionyl)amino)ethyl)phenylsulfonyl)amino)carbonyl]-pyridine-2-carboxylate

EXAMPLE 455

(R)-2-Butyl 5-[((4-(2-((2-phenylacetyl)amino)ethyl)phenylsulfonyl)amino)carbonyl]-pyridine-2-carboxylate

EXAMPLE 456

(R)-2-Butyl 5-[((4-(2-((phenoxyacetyl)amino)ethyl)phenylsulfonyl)amino)carbonyl]-pyridine-2-carboxylate

EXAMPLE 457

(R)-2-Butyl 5-[((4-(2-((4-fluorobenzoyl)amino)ethyl)phenylsulfonyl)amino)carbonyl]-pyridine-2-carboxylate

EXAMPLE 458

(R)-2-Butyl 5-[((4-(2-((4-ethoxybenzoyl)amino)ethyl)phenylsulfonyl)amino)carbonyl]-pyridine-2-carboxylate

EXAMPLE 459

(R)-2-Butyl 5-[((4-(2-((cyclohexanoyl)amino)ethyl)phenylsulfonyl)amino)carbonyl]-pyridine-2-carboxylate

EXAMPLE 460

(R)-2-Butyl 5-[((4-(2-((cyclohexylacetyl)amino)ethyl)-phenylsulfonyl)amino)carbonyl]-pyridine-2-carboxylate

EXAMPLE 461

(R)-2-Butyl 5-[((4-(2-(2-methylpropionyl)amino)ethyl)-phenylsulfonyl)amino)carbonyl]-pyridine-2-carboxylate

EXAMPLE 462

(R)-2-Butyl 5-[((4-(2-(2-ethylbutanonyl)amino)ethyl)-phenylsulfonyl)amino)carbonyl]-pyridine-2-carboxylate

EXAMPLE 463

(S)-2-Butyl 5-[((4-(2-((2-chloro-5-methoxybenzoyl)amino)ethyl)phenylsulfonyl)amino)carbonyl]-pyridine-2-carboxylate

EXAMPLE 464

(S)-2-Butyl 5-[((4-(2-(acetylamino)ethyl)phenylsulfonyl)amino)carbonyl]-pyridine-2-carboxylate

EXAMPLE 465

(S)-2-Butyl 5-[((4-(2-(n-butanoylamino)ethyl)phenylsulfonyl)amino)carbonyl]-pyridine-2-carboxylate

EXAMPLE 466

(S)-2-Butyl 5-[((4-(2-(benzoylamino)ethyl)phenylsulfonyl)amino)carbonyl]-pyridine-2-carboxylate

EXAMPLE 467

(S)-2-Butyl 5-[((4-(2-((4-chlorobenzoyl)amino)ethyl)-phenylsulfonyl)amino)carbonyl]-pyridine-2-carboxylate

EXAMPLE 468

(S)-2-Butyl 5-[((4-(2-((5-chloro-2-methoxybenzoyl)amino)ethyl)phenylsulfonyl)amino)carbonyl]-pyridine-2-carboxylate

EXAMPLE 469

(S)-2-Butyl 5-[((4-(2-((3-phenyl-n-propionyl)amino)ethyl)phenylsulfonyl)amino)carbonyl]-pyridine-2-carboxylate

EXAMPLE 470

(S)-2-Butyl 5-[((4-(2-((2-phenylacetyl)amino)ethyl)-phenylsulfonyl)amino)carbonyl]-pyridine-2-carboxylate

EXAMPLE 471

(S)-2-Butyl 5-[((4-(2-((phenoxyacetyl)amino)ethyl)-phenylsulfonyl)amino)carbonyl]-pyridine-2-carboxylate

EXAMPLE 472

(S)-2-Butyl 5-[((4-(2-((4-fluorobenzoyl)amino)ethyl)-phenylsulfonyl)amino)carbonyl]-pyridine-2-carboxylate

EXAMPLE 473

(S)-2-Butyl 5-[((4-(2-((4-ethoxybenzoyl)amino)ethyl)-phenylsulfonyl)amino)carbonyl]-pyridine-2-carboxylate

EXAMPLE 474

(S)-2-Butyl 5-[((4-(2-((cyclohexanoyl)amino)ethyl)-phenylsulfonyl)amino)carbonyl]-pyridine-2-carboxylate

EXAMPLE 475

(S)-2-Butyl 5-[((4-(2-((cyclohexylacetyl)amino)ethyl)-phenylsulfonyl)amino)carbonyl]-pyridine-2-carboxylate

EXAMPLE 476

(S)-2-Butyl 5-[((4-(2-(2-methylpropionyl)amino)ethyl)-phenylsulfonyl)amino)carbonyl]-pyridine-2-carboxylate

EXAMPLE 477

(S)-2-Butyl 5-[((4-(2-(2-ethylbutanonyl)amino)ethyl)-phenylsulfonyl)amino)carbonyl]-pyridine-2-carboxylate

EXAMPLE 478

4-Heptyl 5-[((4-(2-((2-chloro-5-methoxybenzoyl)amino)ethyl)phenylsulfonyl)amino)carbonyl]-pyridine-2-carboxylate

EXAMPLE 479

4-Heptyl 5-[((4-(2-(acetylamino)ethyl)phenylsulfonyl)amino)carbonyl]-pyridine-2-carboxylate

EXAMPLE 480

4-Heptyl 5-[((4-(2-(n-butanoylamino)ethyl)phenylsulfonyl)amino)carbonyl]-pyridine-2-carboxylate

EXAMPLE 481

4-Heptyl 5-[((4-(2-(benzoylamino)ethyl)phenylsulfonyl)amino)carbonyl]-pyridine-2-carboxylate

EXAMPLE 482

4-Heptyl 5-[((4-(2-((4-chlorobenzoyl)amino)ethyl)-phenylsulfonyl)amino)carbonyl]-pyridine-2-carboxylate

EXAMPLE 483

Cyclopentyl 5-[((4-(2-((5-chloro-2-methoxybenzoyl)amino)ethyl)phenylsulfonyl)amino)carbonyl]-pyridine-2-carboxylate

EXAMPLE 484

Cyclopentyl 5-[((4-(2-((3-phenyl-n-propionyl)amino)ethyl)phenylsulfonyl)amino)carbonyl]-pyridine-2-carboxylate

EXAMPLE 485

Cyclohexyl 5-[((4-(2-((2-phenylacetyl)amino)ethyl)-phenylsulfonyl)amino)carbonyl]-pyridine-2-carboxylate

EXAMPLE 486

Cyclohexyl 5-[((4-(2-((phenoxyacetyl)amino)ethyl)-phenylsulfonyl)amino)carbonyl]-pyridine-2-carboxylate

EXAMPLE 487

Cyclohexyl 5-[((4-(2-((4-fluorobenzoyl)amino)ethyl)-phenylsulfonyl)amino)carbonyl]-pyridine-2-carboxylate

EXAMPLE 488

Cyclobutyl 5-[((4-(2-((4-ethoxybenzoyl)amino)ethyl)-phenylsulfonyl)amino)carbonyl]-pyridine-2-carboxylate

EXAMPLE 489

2-(2-Methyl-3-butynyl) 5-[((4-(2-((cyclohexanoyl)amino)ethyl)phenylsulfonyl)amino)carbonyl]-pyridine-2-carboxylate

EXAMPLE 490

2-(2-Methyl-3-butynyl) 5-[((4-(2-((cyclohexylacetyl)amino)ethyl)phenylsulfonyl)amino)carbonyl]-pyridine-2-carboxylate

EXAMPLE 491

2-(2-Methyl-3-butynyl) 5-[((4-(2-(2-methylpropionyl)amino)ethyl)phenylsulfonyl)amino)carbonyl]-pyridine-2-carboxylate

EXAMPLE 492

2-(2-Methyl-3-butynyl) 5-[((4-(2-(2-ethylbutanonyl)amino)ethyl)phenylsulfonyl)amino)carbonyl]-pyridine-2-carboxylate

EXAMPLE 493

1-(2-Butynyl) 5-[((3-(2-((2-chloro-5-methoxybenzoyl)amino)ethyl)phenylsulfonyl)amino)carbonyl]-pyridine-2-carboxylate

EXAMPLE 494

1-(3-Butynyl) 5-[((3-(2-(acetylamino)ethyl)phenylsulfonyl)amino)carbonyl]-pyridine-2-carboxylate

EXAMPLE 495

1-(3-Butenyl) 5-[((3-(2-(n-butanoylamino)ethyl)phenylsulfonyl)amino)carbonyl]-pyridine-2-carboxylate

EXAMPLE 496

1-(3-Butenyl) 5-[((3-(2-(benzoylamino)ethyl)phenylsulfonyl)amino)carbonyl]-pyridine-2-carboxylate

EXAMPLE 497

((1R,2S,5R)-(−)menthyl) 5-[((3-(2-((4-chlorobenzoyl)amino)ethyl)phenylsulfonyl)amino)carbonyl]-pyridine-2-carboxylate

EXAMPLE 498

2-(2-Methyl-3-butynyl) 5-[((3-(2-((5-chloro-2-methoxybenzoyl)amino)ethyl)phenylsulfonyl)amino)carbonyl]-pyridine-2-carboxylate

EXAMPLE 499

2-(2-Methyl-3-butynyl 5-[((3-(2-((3-phenyl-n-propionyl)amino)ethyl)phenylsulfonyl)amino)carbonyl]-pyridine-2-carboxylate

EXAMPLE 500

2-Methoxycarbonyl-2,2-dimethylethyl 5-[((3-(2-((3-phenylacetyl)amino)ethyl)phenylsulfonyl)amino)carbonyl]-pyridine-2-carboxylate

EXAMPLE 501

2-Methoxycarbonyl-2,2-dimethylethyl 5-[((4-(3-((phenoxyacetyl)amino)ethyl)phenylsulfonyl)amino)carbonyl]-pyridine-2-carboxylate

EXAMPLE 502

(1R)-Endo-(+)-fenchyl 5-[((3-(2-((4-fluorobenzoyl)amino)ethyl)phenylsulfonyl)amino)carbonyl]-pyridine-2-carboxylate

EXAMPLE 503

(1R)-Endo-(+)-fenchyl 5-[((3-(2-((4-ethoxybenzoyl)amino)ethyl)phenylsulfonyl)amino)carbonyl]-pyridine-2-carboxylate

EXAMPLE 504

1-Isopropoxycarbonylethyl 5-[((3-(2-((cyclohexanoyl)amino)ethyl)phenylsulfonyl)amino)carbonyl]-pyridine-2-carboxylate

EXAMPLE 505

1-Ethoxycarbonylethyl 5-[((3-(2-((cyclohexylacetyl)amino)ethyl)phenylsulfonyl)amino)carbonyl]-pyridine-2-carboxylate

EXAMPLE 506

(1R,2S,5R)-(−)Menthyl 5-](3-(2-(2-methylpropionyl)amino)ethyl)phenylsulfonyl)amino)carbonyl]-pyridine-2-carboxylate

EXAMPLE 507

(1S,2R,5S)-(+)Menthyl 5-[((3-(2-(2-ethylbutanonyl)amino)ethyl)phenylsulfonyl)amino)carbonyl]-pyridine-2-carboxylate

EXAMPLE 508

Methyl 5-[((4-((4-phenyl-n-butanoyl)amino)phenylsulfonyl)amino)carbonyl]-pyridine-2-carboxylate a) 4-((Phenyl-n-butanoyl)amino)benzenesulfonamide
11.1 g (0.11 mol, 15.2 ml) of triethylamine were added to 16.5 g (0.1 mol) of 4-phenylbutyric acid in 300 ml of anhydrous tetrahydrofuran at 0° C. After 30 minutes, 12 g (0.11 mol, 10.5 ml) of ethyl chloroformate were added dropwise at 0° C. A solution of 18.1 g (0.105 mol) of 4-aminobenzenesulfonamide in 150 ml of anhydrous tetrahydrofuran was added dropwise to this thick suspension at −10° C. The mixture was stirred at 0° C. for 1 hour and at 25° C. for 1 hour and concentrated in vacuo, and the residue was treated with aqueous hydrochloric acid. The crystalline crude product was washed with water and recrystallized from 250 ml of methanol; yield 18 g; melting point 166° to 168° C.

b) 1.8 g (10 mmol) of 2-methylpyridine-2,5-dicarboxylate in 300 ml of acetonitrile were reacted with 3.2 g (10 mmol) of the above benzenesulfonamide, 2.1 g (10 mmol) of N,N'-dicyclohexylcarbodiimide and 1.2 g (10 mmol) of 4-N,N-dimethylaminopyridine analogously to Example 32b).

The undissolved substance was filtered off, the filtrate was concentrated, aqueous hydrochloric acid (pH 1) was added and the finely crystalline product was filtered off with suction. This product was dissolved in N,N-dimethylformamide, and water was added until clouding started. The crystalline crude product was washed with water and dried; 3.3 g; melting point 258° to 264° C. After chromatography with ethyl acetate/methanol (3:1) over silica gel, corresponding fractions were evaporated and the residue was recrystallized from methanol. 1.4 g of colorless crystalline product were isolated; melting point 258° C. (with decomposition).

EXAMPLE 509
Methyl 5-]((4-(3-phenyl-n-propionylamino)phenylsulfonyl)amino)carbonyl]-pyridine-2-carboxylate

EXAMPLE 510
Methyl 5-[((4-(2-phenylacetylamino)phenylsulfonyl)amino)carbonyl]-pyridine-2-carboxylate

EXAMPLE 511
Methyl 5-[((4-(benzoylamino)phenylsulfonyl)amino)carbonyl]-pyridine-2-carboxylate

EXAMPLE 512
Methyl 5-[((4-(acetylamino)phenylsulfonyl)amino)carbonyl]-pyridine-2-carboxylate

EXAMPLE 513
Methyl 5-[((4-(n-propionylamino)phenylsulfonyl)amino)carbonyl]-pyridine-2-carboxylate

EXAMPLE 514
Methyl 5-[((4-(n-hexanoylamino)phenylsulfonyl)amino)carbonyl]-pyridine-2-carboxylate

EXAMPLE 515
Methyl 5-[((4-((2-phenoxyacetyl)amino)phenylsulfonyl)amino)carbonyl]-pyridine-2-carboxylate
Melting point 222° to 224° C.

EXAMPLE 516
Methyl 5-[((4-(n-butanoylamino)phenylsulfonyl)amino)carbonyl]-pyridine-2-carboxylate

EXAMPLE 517
Methyl 5-[((4-(cyclohexanoylamino)phenylsulfonyl)amino)carbonyl]-pyridine-2-carboxylate

EXAMPLE 518
Methyl 5-[((4-(cyclohexylacetyl)amino)phenylsulfonyl)amino)carbonyl]-pyridine-2-carboxylate

EXAMPLE 519
1-Propyl 5-[((4-(4-phenyl-n-butanoylamino)phenylsulfonyl)amino)carbonyl]-pyridine-2-carboxylate

EXAMPLE 520
1-Propyl 5-[((4-(3-phenyl-n-propionylamino)phenylsulfonyl)carbonyl]-pyridine-2-carboxylate

EXAMPLE 521
2-Propyl 5-[((4-(2-phenylacetylamino)phenylsulfonyl)amino)carbonyl]-pyridine-2-carboxylate

EXAMPLE 522
2-Propyl 5-[((4-(benzoylamino)phenylsulfonyl)amino)carbonyl]-pyridine-2-carboxylate

EXAMPLE 523
3-Pentyl 5-[((4-(2-methylpentanoylamino)phenylsulfonyl)amino)carbonyl]-pyridine-2-carboxylate

EXAMPLE 524
3-Pentyl 5-[((4-(n-propionylamino)phenylsulfonyl)amino)carbonyl]-pyridine-2-carboxylate

EXAMPLE 525
3-Pentyl 5-[((4-(n-hexanoylamino)phenylsulfonyl)amino)carbonyl]-pyridine-2-carboxylate

EXAMPLE 526
2-(2-Methylhexyl) 5-[((4-((2-phenoxyacetyl)amino)phenylsulfonyl)amino)carbonyl]-pyridine-2-carboxylate

EXAMPLE 527
2-(2-Methylhexyl) 5-[((4-(n-butanoylamino)phenylsulfonyl)amino)carbonyl]-pyridine-2-carboxylate

EXAMPLE 528
4-Heptyl 5-[((4-(cyclohexanoylamino)phenylsulfonyl)amino)carbonyl]-pyridine-2-carboxylate

EXAMPLE 529
2-Propyl 5-[((4-(cyclohexylacetyl)amino)phenylsulfonyl)amino)carbonyl]-pyridine-2-carboxylate

EXAMPLE 530
Methyl 5-[(((4-phenyl-n-butyl)sulfonyl)amino)carbonyl]-pyridine-2-carboxylate

EXAMPLE 531
Methyl 5-[(((2-phenoxyethyl)sulfonyl)amino)carbonyl]-pyridine-2-carboxylate

EXAMPLE 532
Methyl 5-[((2-(4-fluorophenoxy)ethylsulfonyl)amino)carbonyl]-pyridine-2-carboxylate

EXAMPLE 533
Methyl 5-[((phenylmethylsulfonyl)amino)carbonyl]-pyridine-2-carboxylate

EXAMPLE 534
Methyl 5-[(((2-phenylethyl)sulfonyl)amino)carbonyl]-pyridine-2-carboxylate

EXAMPLE 535
Methyl 5-[(((2-(4-fluorophenyl)ethyl)sulfonyl)amino)carbonyl]-pyridine-2-carboxylate

EXAMPLE 536
Methyl 5-[(((2-(4-methoxyphenyl)ethyl)sulfonyl)amino)carbonyl]-pyridine-2-carboxylate

EXAMPLE 537
Methyl 5-[(((3-phenyl-n-propyl)sulfonyl)amino)carbonyl]-pyridine-2-carboxylate

EXAMPLE 538
Ethyl 5-[(((4-phenyl-n-butyl)sulfonyl)amino)carbonyl]-pyridine-2-carboxylate

EXAMPLE 539
Ethyl 5-[(((2-phenoxyethyl)sulfonyl)amino)carbonyl]-pyridine-2-carboxylate

EXAMPLE 540
Ethyl 5-[(((2-(4-fluorophenoxy)ethyl)sulfonyl)amino)carbonyl]-pyridine-2-carboxylate

EXAMPLE 541

Ethyl 5-[((phenylmethylsulfonyl)amino)carbonyl]-pyridine-2-carboxylate

EXAMPLE 542

Ethyl 5-[(((2-phenylethyl)sulfonyl)amino)carbonyl]-pyridine-2-carboxylate

EXAMPLE 543

Ethyl 5-[(((2-(4-fluorophenyl)ethyl)sulfonyl)amino)carbonyl]-pyridine-2-carboxylate

EXAMPLE 544

Ethyl 5-[(((2-(4-methoxyphenyl)ethyl)sulfonyl)amino)carbonyl]-pyridine-2-carboxylate

EXAMPLE 545

Ethyl 5-[(((3-phenyl-n-propyl)sulfonyl)amino)carbonyl]-pyridine-2-carboxylate

EXAMPLE 546

2-Propyl 5-[(((4-phenyl-n-butyl)sulfonyl)amino)carbonyl]-pyridine-2-carboxylate

EXAMPLE 547

2-Propyl 5-[(((2-phenoxyethyl)sulfonyl)amino)carbonyl]-pyridine-2-carboxylate

EXAMPLE 548

2-Propyl 5-[(((2-(4-fluorophenoxy)ethyl)sulfonyl)amino)carbonyl]-pyridine-2-carboxylate

EXAMPLE 549

2-Propyl 5-[((phenylmethylsulfonyl)amino)carbonyl]-pyridine-2-carboxylate

EXAMPLE 550

2-Propyl 5-[(((2-phenylethyl)sulfonyl)amino)carbonyl]-pyridine-2-carboxylate

EXAMPLE 551

2-Propyl 5-[(((2-(4-fluorophenyl)ethyl)sulfonyl)amino)carbonyl]-pyridine-2-carboxylate

EXAMPLE 552

2-Propyl 5-[(((2-(4-methoxyphenyl)ethyl)sulfonyl)amino)carbonyl]-pyridine-2-carboxylate

EXAMPLE 553

2-Propyl 5-[(((3-phenyl-n-propyl)sulfonyl)amino)carbonyl]-pyridine-2-carboxylate

EXAMPLE 554

Methyl 5-[((4-(2-(acetylamino)methyl)phenylsulfonyl)amino)carbonyl]-pyridine-2-carboxylate

EXAMPLE 555

Methyl 5-[((4-(2-(n-butanoylamino)methyl)phenylsulfonyl)amino)carbonyl]-pyridine-2-carboxylate

EXAMPLE 556

Methyl 5-[((4-(2-(benzoylamino)methyl)phenylsulfonyl)amino)carbonyl]-pyridine-2-carboxylate

EXAMPLE 557

Methyl 5-[((4-(2-((4-chlorobenzoyl)amino)methyl)phenylsulfonyl)amino)carbonyl]-pyridine-2-carboxylate

EXAMPLE 558

Methyl 5-[((4-(2-((5-chloro-2-methoxybenzoyl)amino)methyl)phenylsulfonyl)amino)carbonyl]-pyridine-2-carboxylate

EXAMPLE 559

Methyl 5-[((4-(2-((3-phenyl-n-propionyl)amino)methyl)phenylsulfonyl)amino)carbonyl]-pyridine-2-carboxylate

EXAMPLE 560

Methyl 5-[((4-(2-((2-phenylacetyl)amino)methyl)phenylsulfonyl)amino)carbonyl]-pyridine-2-carboxylate

EXAMPLE 561

Methyl 5-[((4-(2-((phenoxyacetyl)amino)methyl)phenylsulfonyl)amino)carbonyl]-pyridine-2-carboxylate

EXAMPLE 562

Methyl 5-[((4-(2-((4-fluorobenzoyl)amino)methyl)phenylsulfonyl)amino)carbonyl]-pyridine-2-carboxylate

EXAMPLE 563

Methyl 5-[((4-(2-((4-ethoxybenzoyl)amino)methyl)phenylsulfonyl)amino)carbonyl]-pyridine-2-carboxylate

EXAMPLE 564

Methyl 5-[((4-(2-((cyclohexanoyl)amino)methyl)phenylsulfonyl)amino)carbonyl]-pyridine-2-carboxylate

EXAMPLE 565

Methyl 5-[((4-(2-((cyclohexylacetyl)amino)methyl)phenylsulfonyl)amino)carbonyl]-pyridine-2-carboxylate

EXAMPLE 566

Methyl 5-[((4-(2-((2-methylpropionyl)amino)methyl)phenylsulfonyl)amino)carbonyl]-pyridine-2-carboxylate

EXAMPLE 567

Methyl 5-[((3-(2-((2-chloro-5-methoxybenzoyl)amino)methyl)phenylsulfonyl)amino)carbonyl]-pyridine-2-carboxylate

EXAMPLE 568

Methyl 5-[((4-(2-(n-pentanoylamino)methyl)phenylsulfonyl)amino)carbonyl]-pyridine-2-carboxylate

EXAMPLE 569

Methyl 5-[((4-(2-((3-methylbutanoyl)amino)methyl)phenylsulfonyl)amino)carbonyl]-pyridine-2-carboxylate

EXAMPLE 570

Methyl 5-[((4-(2-((4-methylpentanoyl)amino)methyl)-phenylsulfonyl)amino)carbonyl]-pyridine-2-carboxylate

EXAMPLE 571

Methyl 5-[((4-(2-((3-cyclohexyl-n-propionyl)amino)methyl)phenylsulfonyl)amino)carbonyl]-pyridine-2-carboxylate

EXAMPLE 572

2-Propyl 5-[((4-(2-(n-pentanoylamino)methyl)phenylsulfonyl)amino)carbonyl]-pyridine-2-carboxylate

EXAMPLE 573

2-Propyl 5-[((4-(2-((4-methylbutanoyl)amino)methyl)-phenylsulfonyl)amino)carbonyl]-pyridine-2-carboxylate

EXAMPLE 574

2-Propyl 5-[((4-(2-((4-methylpentanoyl)amino)methyl)-phenylsulfonyl)amino)carbonyl]-pyridine-2-carboxylate

EXAMPLE 575

3-Pentyl 5-[((4-(2-(acetylamino)methyl)phenylsulfonyl)amino)carbonyl]-pyridine-2-carboxylate

EXAMPLE 576

2-Propyl 5-[((4-(2-((5-chloro-2-methoxybenzoyl)amino)methyl)phenylsulfonyl)amino)carbonyl]-pyridine-2-carboxylate

EXAMPLE 577

2-Propyl 5-[((4-(2-((3-phenyl-n-propionyl)amino)methyl)phenylsulfonyl)amino)carbonyl]-pyridine-2-carboxylate

EXAMPLE 578

2-Methyl 5-[((4-(2-((2-(3,4-dimethoxyphenyl)acetyl)amino)ethyl)phenylsulfonyl)amino)carbonyl]-pyridine-2-carboxylate (Method B)

Melting point 164° to 169° C. (from methanol/diisopropyl ether)

EXAMPLE 579

2-Propyl 5-[((4-(2-((3,4-dimethoxybenzoyl)amino)ethyl)phenylsulfonyl)amino)carbonyl]-pyridine-2-carboxylate

EXAMPLE 580

2-Propyl 5-[((4-(2-((2,5-dimethoxybenzoyl)amino)ethyl)phenylsulfonyl)amino)carbonyl]-pyridine-2-carboxylate

EXAMPLE 581

2-Propyl 5-[((4-(2-((3,4-dimethoxybenzoyl)amino)ethyl)phenylsulfonyl)amino)carbonyl]-pyridine-2-carboxylate

EXAMPLE 582

2-Propyl 5-[((4-(2-((3,4-dimethoxybenzoyl)amino)ethyl)phenylsulfonyl)amino)carbonyl]-pyridine-2-carboxylate

EXAMPLE 583

2-Propyl 5-[((4-(2-((2,5-dimethoxybenzoyl)amino)ethyl)phenylsulfonyl)amino)carbonyl]-pyridine-2-carboxylate

EXAMPLE 584

2-Propyl 5-[((4-(2-((3,4-dimethoxybenzoyl)amino)ethyl)phenylsulfonyl)amino)carbonyl]-pyridine-2-carboxylate

EXAMPLE 585

2-Propyl 5-[((4-(2-((3,4-dimethoxybenzoyl)amino)ethyl)phenylsulfonyl)amino)carbonyl]-pyridine-2-carboxylate

EXAMPLE 586

2-Propyl 5-[((4-(2-((2,5-dimethoxybenzoyl)amino)ethyl)phenylsulfonyl)amino)carbonyl]-pyridine-2-carboxylate

EXAMPLE 587

2-Propyl 5-[((4-(2-((3,4-dimethoxybenzoyl)amino)ethyl)phenylsulfonyl)amino)carbonyl]-pyridine-2-carboxylate

EXAMPLE 588

2-Propyl 5-[((4-(2-((3,4-dimethoxybenzoyl)amino)ethyl)phenylsulfonyl)amino)carbonyl]-pyridine-2-carboxylate

EXAMPLE 589

2-Propyl 5-[((4-(2-((2,5-dimethoxybenzoyl)amino)ethyl)phenylsulfonyl)amino)carbonyl]-pyridine-2-carboxylate

EXAMPLE 590

2-Propyl 5-[((4-(2-((3,4-dimethoxybenzoyl)amino)ethyl)phenylsulfonyl)amino)carbonyl]-pyridine-2-carboxylate

EXAMPLE 591

2-Propyl 5-[((4-(2-((3,4-dimethoxybenzoyl)amino)ethyl)phenylsulfonyl)amino)carbonyl]-pyridine-2-carboxylate

EXAMPLE 592

2-Propyl 5-[((4-(2-((2,5-dimethoxybenzoyl)amino)ethyl)phenylsulfonyl)amino)carbonyl]-pyridine-2-carboxylate

EXAMPLE 593

Methyl 5-[((4-((2-(4-methoxyphenyl)ethyl)aminocarbonyl)phenylsulfonyl)amino)carbonyl]-pyridine-2-carboxylate $\alpha,\alpha,\alpha$-tris(hydroxymethyl)methylamine salt 0.5 g (1.0 mmol) of the title compound from Example 36) was suspended in 50 ml of a tetrahydrofuran/methylene chloride mixture, and 0.12 g (1 mmol) of $\alpha,\alpha,\alpha$-tris(hydroxymethyl)methylamine was added at 20° C.

The mixture was stirred for 2 hours with gentle heating, complete dissolution occurring. After the mixture had been cooled, it was concentrated in vacuo and the amorphous residue was dried using an oil pump. This gave 0.5 g of the title compound; melting point about 50° C. The product dissolved in water, the pH of the aqueous solution being 7.

In Examples 594 to 598, corresponding to formula I, X is a bond.

EXAMPLE 594 a) Methyl 5-[(4-fluorophenylsulfonyl)amino]-pyridine-2-carboxylate 3.8 g (25 mmol) of methyl 5-amino-pyridine-2-carboxylate were dissolved in 75 ml of anhydrous pyridine, and 5.8 g (30 mmol) of 4-fluorobenzenesulfonyl chloride were added in portions, whereupon the temperature of the reaction solution rose to 35° C. After 1 hour, the mixture was concentrated in vacuo and the residue was triturated with water, filtered off with suction, washed with water and dried. This gave 7.3 g of product, melting point 183° to 185° C.

EXAMPLE 595

2-Propyl 5-[(4-fluorophenylsulfonyl)amino]-pyridine-2-carboxylate

EXAMPLE 596

Methyl 5-[(3,5-bis[trifluoroethyloxy)phenylsulfonyl)amino]-pyridine-2-carboxylate Melting point 158° to 160° C. (from water)

EXAMPLE 597

Methyl 5-[(1-naphthylsulfonyl)amino]-pyridine-2-carboxylate

Melting point 176° to 179° C. (from water)

EXAMPLE 598

Methyl 5-[(4-(3-chloro-2-cyano-phenoxy)phenylsulfonyl)amino]-pyridine-2-carboxylate Melting point 153° to 155° C. (from ethanol)

In Examples 599 to 660, corresponding to formula I, X is —CO—:

EXAMPLE 599

Methyl 5-[((4-(2-(n-hexanoylamino)ethyl)phenylsulfonyl)amino]-pyridine-2-carboxylate

EXAMPLE 600

Methyl 5-[((4-(2-(n-heptanoylamino)ethyl)phenylsulfonyl)amino)carbonyl]-pyridine-2-carboxylate

EXAMPLE 601

Methyl 5-[((4-(2-(n-octanoylamino)ethyl)phenylsulfonyl)amino)carbonyl]-pyridine-2-carboxylate

EXAMPLE 602

1-(2,2-Dimethyl-3-hydroxypropyl) 5-[((4-(2-(acetylamino)ethyl)phenylsulfonyl)amino)carbonyl]-pyridine-2-carboxylate

EXAMPLE 603

1-(2,2-Dimethyl-3-hydroxypropyl) 5-[((4-(2-(n-butanoylamino)ethyl)phenylsulfonyl)amino)carbonyl]-pyridine-2-carboxylate

EXAMPLE 604

1-(2,2-Dimethyl-3-hydroxypropyl) 5-[((4-(2-(n-butanoylamino)ethyl)phenylsulfonyl)amino)carbonyl]-pyridine-2-carboxylate

EXAMPLE 605

1-(2,2-Dimethyl-3-hydroxypropyl) 5-[((4-(2-(n-hexanoylamino)ethyl)phenylsulfonyl)amino)carbonyl]-pyridine-2-carboxylate

EXAMPLE 606

1-(2,2-Dimethyl-3-hydroxypropyl) 5[((4-(2-(4-methylpentanoylamino)ethyl)phenylsulfonyl)amino)carbonyl]-pyridine-2-carboxylate

EXAMPLE 607

1-(2,2-Dimethyl-3-hydroxypropyl) 5-[((4-(2-(n-heptanoylamino)ethyl)phenylsulfonyl)amino)carbonyl]-pyridine-2-carboxylate

EXAMPLE 608

1-(2,2-Dimethyl-3-hydroxypropyl) 5-[((4-(2-(n-octanoylamino)ethyl)phenylsulfonyl)amino)carbonyl]-pyridine-2-carboxylate

EXAMPLE 609

1-(2,2-Dimethyl-3-hydroxypropyl) 5-[((4-(2-((2-methylpropionyl)amino)ethyl)phenylsulfonyl)amino)carbonyl]-pyridine-2-carboxylate

EXAMPLE 610

1-(2,2-Dimethyl-3-hydroxypropyl 5-[((4-(2-(benzoylamino)ethyl)phenylsulfonyl)amino)carbonyl]-pyridine-2-carboxylate

EXAMPLE 611

1-(2,2-Dimethyl-3-hydroxypropyl) 5-[((4-(2-((4-n-butoxybenzoyl)amino)ethyl)phenylsulfonyl)amino)carbonyl]-pyridine-2-carboxylate

EXAMPLE 612

1-(2,2-Dimethyl-3-hydroxypropyl) 5-[((4-(2-((5-chloro-2-methoxybenzoyl)amino)ethyl)phenylsulfonyl)amino)carbonyl]-pyridine-2-carboxylate

EXAMPLE 613

1-(2,2-Dimethyl-3-hydroxypropyl) 5-[((4-(2-((3-phenyl-n-propionyl)amino)ethyl)phenylsulfonyl)amino)carbonyl]-pyridine-2-carboxylate

EXAMPLE 614

1-(2,2-Dimethyl-3-hydroxypropyl) 5-[((4-(2-((2-phenylacetyl)amino)ethyl)phenylsulfonyl)amino)carbonyl]-pyridine-2-carboxylate

EXAMPLE 615

1-(2,2-Dimethyl-3-hydroxypropyl) 5-[((4-(2-((phenoxyacetyl)amino)ethyl)phenylsulfonyl)amino)carbonyl]-pyridine-2-carboxylate

EXAMPLE 616

1-(2,2-Dimethyl-3-hydroxypropyl) 5-[((4-(2-((4-fluorobenzoyl)amino)ethyl)phenylsulfonyl)amino)carbonyl]-pyridine-2-carboxylate

EXAMPLE 617

1-(2,2-Dimethyl-3-hydroxypropyl) 5-[((4-(2-((4-ethoxybenzoyl)amino)ethyl)phenylsulfonyl)amino)carbonyl]-pyridine-2-carboxylate

EXAMPLE 618

1-(2,2-Dimethyl-3-hydroxypropyl) 5-[((4-(2-((cyclohexanoyl)amino)ethyl)phenylsulfonyl)amino)carbonyl]-pyridine-2-carboxylate

EXAMPLE 619

1-(2,2-Dimethyl-3-hydroxypropyl) 5-[((4-(2-((cyclohexylacetyl)amino)ethyl)phenylsulfonyl)amino)carbonyl]-pyridine-2-carboxylate

EXAMPLE 620

1-(2,2-Dimethyl-3-hydroxypropyl) 5-[((3-(2-((2-chloro-5-methoxybenzoyl)amino)ethyl)phenylsulfonyl)amino)carbonyl]-pyridine-2-carboxylate

EXAMPLE 621

1-(2,2-Dimethyl-3-hydroxypropyl) 5-[((4-(2-((2-(3,4-dimethoxyphenyl)acetyl)amino)ethyl)phenylsulfonyl)amino)carbonyl]-pyridine-2-carboxylate

EXAMPLE 622

1-(2-Ethylbutyl) 5-[((4-(2-(acetylamino)ethyl)phenylsulfonyl)amino)carbonyl]-pyridine-2-carboxylate

EXAMPLE 623

1-(2-Ethylbutyl) 5-[((4-(2-(n-butanoylamino)ethyl)phenylsulfonyl)amino)carbonyl]pyridine-2-carboxylate

EXAMPLE 624

1-(2-Ethylbutyl) 5-[((4-(2-(n-pentanoylamino)ethyl)phenylsulfonyl)amino)carbonyl]-pyridine-2-carboxylate

EXAMPLE 625

1-(2-Ethylbutyl) 5-[((4-(2-(n-hexanoylamino)ethyl)phenylsulfonyl)amino)carbonyl]-pyridine-2-carboxylate

EXAMPLE 626

1-(2-Ethylbutyl) 5-[((4-(2-(4-methylpentanoylamino)ethyl)phenylsulfonyl)amino)carbonyl]-pyridine-2-carboxylate

EXAMPLE 627

1-(2-Ethylbutyl) 5-[((4-(2-(n-heptanoylamino)ethyl)phenylsulfonyl)amino)carbonyl]-pyridine-2-carboxylate

EXAMPLE 628

1-(2-Ethylbutyl) 5-[((4-(2-(n-octanoylamino)ethyl)phenylsulfonyl)amino)carbonyl]-pyridine-2-carboxylate

EXAMPLE 629

1-(2-Ethylbutyl) 5-[((4-(2-((2-methylpropionyl)amino)ethyl)phenylsulfonyl)amino)carbonyl]-pyridine-2-carboxylate

EXAMPLE 630

1-(2-Ethylbutyl) 5-[((4-(2-(benzoylamino)ethyl)phenylsulfonyl)amino)carbonyl]-pyridine-2-carboxylate

EXAMPLE 631

1-(2-Ethylbutyl) 5-[((4-(2-((n-butoxybenzoyl)amino)ethyl)phenylsulfonyl)amino)carbonyl]-pyridine-2-carboxylate

EXAMPLE 632

1-(2-Ethylbutyl) 5-[((4-(2-((5-chloro-2-methoxybenzoyl)amino)ethyl)phenylsulfonyl)amino)carbonyl]-pyridine-2-carboxylate

EXAMPLE 633

1-(2-Ethylbutyl) 5-[((4-(2-((3-phenyl-n-propionyl)amino)ethyl)phenylsulfonyl)amino)carbonyl]-pyridine-2-carboxylate

EXAMPLE 634

1-(2-Ethylbutyl) 5-[((4-(2-((2-phenylacetyl)amino)ethyl)phenylsulfonyl)amino)carbonyl]-pyridine-2-carboxylate

EXAMPLE 635

1-(2-Ethylbutyl) 5-[((4-(2-((phenoxyacetyl)amino)ethyl)phenylsulfonyl)amino)carbonyl]-pyridine-2-carboxylate

EXAMPLE 636

1-(2-Ethylbutyl) 5-[((4-(2-((4-fluorobenzoyl)amino)ethyl)phenylsulfonyl)amino)carbonyl]-pyridine-2-carboxylate

EXAMPLE 637

1-(2-Ethylbutyl) 5-[((4-(2-((4-ethoxybenzoyl)amino)ethyl)phenylsulfonyl)amino)carbonyl]-pyridine-2-carboxylate

EXAMPLE 638

1-(2-Ethylbutyl) 5-[((4-(2-((cyclohexanoyl)amino)ethyl)phenylsulfonyl)amino)carbonyl]-pyridine-2-carboxylate

EXAMPLE 639

1-(2-Ethylbutyl) 5-[((4-(2-((cyclohexylacetyl)amino)ethyl)phenylsulfonyl)amino)carbonyl]-pyridine-2-carboxylate

EXAMPLE 640

1-(2-Ethylbutyl) 5-[((3-(2-((2-chloro-5-methoxybenzoyl)amino)ethyl)phenylsulfonyl)amino)carbonyl]-pyridine-2-carboxylate

EXAMPLE 641

1-(2-Ethylbutyl) 5-[((4-(2-((2-(3,4-dimethoxyphenyl)acetyl)amino)ethyl)phenylsulfonyl)amino)carbonyl]-pyridine-2-carboxylate

EXAMPLE 642

1-(2,2-Dimethylpropyl) 5-[((4-(2-(acetylamino)ethyl)phenylsulfonyl)amino)carbonyl]-pyridine-2-carboxylate

EXAMPLE 643

1-(2,2-Dimethylpropyl) 5-[((4-(2-(n-butanoylamino)ethyl)phenylsulfonyl)amino)carbonyl]-pyridine-2-carboxylate

EXAMPLE 644

1-(2,2-Dimethylpropyl) 5-[((4-(2-(n-pentanoylamino)ethyl)phenylsulfonyl)amino)carbonyl]-pyridine-2-carboxylate

EXAMPLE 645

1-(2,2-Dimethylpropyl) 5-[((4-(2-(n-hexanoylamino)ethyl)phenylsulfonyl)amino)carbonyl]-pyridine-2-carboxylate

EXAMPLE 646

1-(2,2-Dimethylpropyl) 5-[((4-(2-(4-methylpentanoylamino)ethyl)phenylsulfonyl)amino)carbonyl]-pyridine-2-carboxylate

EXAMPLE 647

1-(2,2-Dimethylpropyl) 5-[((4-(2-(n-heptanoylamino)ethyl)phenylsulfonyl)amino)carbonyl]-pyridine-2-carboxylate

EXAMPLE 648

1-(2,2-Dimethylpropyl) 5-[((4-(2-(n-octanoylamino)ethyl)phenylsulfonyl)amino)carbonyl]-pyridine-2-carboxylate

EXAMPLE 649

1-(2,2-Dimethylpropyl) 5[((4-(2((2-methylpropionyl)amino)ethyl)phenylsulfonyl)amino)carbonyl]-pyridine-2-carboxylate

EXAMPLE 650

1-(2,2-Dimethylpropyl) 5-[((4-(2-(benzoylamino)ethyl)phenylsulfonyl)amino)carbonyl]-pyridine-2-carboxylate

EXAMPLE 651

1-(2,2-Dimethylpropyl) 5-[((4-(2-((n-butoxybenzoyl)amino)ethyl)phenylsulfonyl)amino)carbonyl]-pyridine-2-carboxylate

EXAMPLE 652

1-(2,2-Dimethylpropyl) 5-]((4-(2-((5-chloro-2-methoxybenzoyl)amino)ethyl)phenylsulfonyl)amino)carbonyl]-pyridine-2-carboxylate

EXAMPLE 652

1-(2,2-Dimethylpropyl) 5-[((4-(2-((5-chloro-2-methoxybenzoyl)amino)ethyl)phenylsulfonyl)amino)carbonyl]-pyridine-2-carboxylate

EXAMPLE 653

1-(2,2-Dimethylpropyl) 5-[((4-(2-((3-phenyl-n-propionyl)amino)ethyl)phenylsulfonyl)amino)carbonyl]-pyridine-2-carboxylate

EXAMPLE 654

1-(2,2-Dimethylpropyl) 5-[((4-(2-((2-phenylacetyl)amino)ethyl)phenylsulfonyl)amino)carbonyl]-pyridine-2-carboxylate

EXAMPLE 655

1-(2,2-Dimethylpropyl) 5-[((4-(2-((phenoxyacetyl)amino)ethyl)phenylsulfonyl)amino)carbonyl]-pyridine-2-carboxylate

EXAMPLE 656

1-(2,2-Dimethylpropyl) 5-[((4-(2-((4-fluorobenzoyl)amino)ethyl)phenylsulfonyl)amino)carbonyl]-pyridine-2-carboxylate

EXAMPLE 657

1-(2,2-Dimethylpropyl) 5-[((4-(2-((4-ethoxybenzoyl)amino)ethyl)phenylsulfonyl)amino)carbonyl]-pyridine-2-carboxylate

EXAMPLE 658

1-(2,2-Dimethylpropyl) 5-[((4-(2-((cyclohexanoyl)amino)ethyl)phenylsulfonyl)amino)carbonyl]-pyridine-2-carboxylate

EXAMPLE 659

1-(2,2-Dimethylpropyl) 5-[((4-(2-((cyclohexylacetyl)amino)ethyl)phenylsulfonyl)amino)carbonyl]-pyridine-2-carboxylate

EXAMPLE 660

1-(2,2-Dimethylpropyl) 5-[((3-(2-(2-chloro-5-methoxybenzoyl)amino)ethyl)phenylsulfonyl)amino)carbonyl]-pyridine-2-carboxylate

We claim:

1. An acylsulfonamido- or sulfonamidopyridine-2-carboxylic acid ester or its pyridine N-oxide of the formula

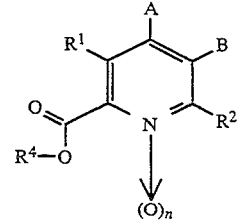

in which

A=$R^3$ and B=X—$NR^5R^6$ and

X is —CO— and $R^1$, $R^2$ and $R^3$ are identical or different and are hydrogen, ($C_1$–$C_6$)-alkyl, ($C_1$–$C_6$)-alkoxy, fluorine, chlorine or bromine, nitrile, hydroxyl, amino, optionally mono-or disubstituted by ($C_1$–$C_4$)-alkyl, hydroxy-($C_1$–$C_4$)-alkyl or ($C_1$–$C_6$)-alkylcarbonyloxy, $R^4$ is the radical of an alcohol $R^4$OH, in which $R^4$ is ($C_1$–$C_{10}$)-alkanoyloxy-($C_1$–$C_6$)-alkyl, benzyloxy-($C_1$–$C_6$)-alkyl, benzyloxycarbonyloxy-($C_1$–$C_6$)-alkyl or alkoxycarbonyloxy-($C_1$–$C_6$)-alkyl, a branched or unbranched cyclic aliphatic ($C_3$–$C_{16}$)-alkyl radical, a branched or unbranched cyclic ($C_3$–$C_{16}$)-alkenyl radical, a ($C_2$–$C_{16}$)-alkynyl radical or a ($C_4$–$C_{16}$)-alkenynyl radical, each of which can contain one or more multiple bonds, or a ($C_6$–$C_{16}$)-aryl radical, a ($C_7$–$C_{16}$)-aralkyl radical or a 5- or 6-membered heteroaryl radical or a 5- or 6-membered heteroaralkyl radical, carrying one or more substituents selected from the series consisting of hydroxyl, halogen, cyano, trifluoromethyl, nitro, carboxyl, ($C_1$–$C_{12}$)-alkyl, ($C_3$–$C_8$)-cycloalkyl, ($C_6$–$C_{12}$)-aryl, ($C_7$–$C_{16}$)-aralkyl, ($C_3$–$C_{12}$)-alkenyl, ($C_3$–$C_{12}$)-alkynyl, ($C_1$–$C_{12}$)-alkoxy, ($C_1$–$C_{12}$)-alkoxy-($C_1$–$C_{12}$)-alkyl, ($C_1$–$C_{12}$)-alkoxy-($C_1$–$C_{12}$)-alkoxy, ($C_6$–$C_{12}$)-aryloxy, ($C_7$–$C_{16}$)-aralkyloxy, ($C_1$–$C_8$)-hydroxyalkyl, —O—[$CH_2$]$_x$$C_f$H$_{(2f+1-g)}$F$_g$, —OCF$_2$Cl, and —OCF$_2$—CHFCl, ($C_1$–$C_{12}$)-alkylcarbonyl, ($C_3$–$C_8$)-cycloalkylcarbonyl, ($C_6$–$C_{12}$)-arylcarbonyl, ($C_7$–$C_{16}$)-aralkylcarbonyl, cinnamoyl, ($C_3$–$C_{12}$)-alkenylcarbonyl, ($C_3$–$C_{12}$)-alkynylcarbonyl, ($C_1$–$C_{12}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl, ($C_3$–$C_8$)-cycloalkoxycarbonyl, ($C_3$–$C_{12}$)-alkenyloxycarbonyl, ($C_3$–$C_{12}$)-alkynyloxycarbonyl, ($C_1$–$C_{12}$)-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkyl)carbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$ arylcarbamoyloxy, N-$(C_7-C_{16})$-aralkylcarbamoyloxy, N-$((C_1-C_{10})$-alkoxy-$(C_1-C_{10})$-alkyl)carbamoyloxy,N-$(C_1-C_{10})$-alkyl-N-$(C_7-C_{16})$-aralkylcarbamoyloxy, N-$((C_1-C_{10})$-alkyl))carbamoyloxy, N-$((C_6-C_{16})$-aryloxy-$(C_1-C_{10})$-alkyl)carbamoyloxy, N-$((C_7-C_{16})$-aralkyloxy-$(C_1-C_{10})$-alkyl)carbamoyloxy, N-$((C_1-C_{10})$-alkyl-N-$(C_1-C_{10})$-alkoxy-$(C_1-C_{10})$-alkyl)carbamoyloxy, N-$(C_1-C_{10})$-alkyl-N-$((C_6-C_{16})$-aryloxy-$(C_1-C_{10})$-alkyl)carbamoyloxy, N-$(C_1-C_{10})$-alkyl-N-$((C_7-C_{16})$-aralkyloxy$(C_1-C_{10})$-alkyl)carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-alkyl-aralkylamino, N-alkyl-arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N,-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfinyl, $(C_6-C_{16})$-arylmercapto, $(C_6-C_{16})$-arylsulfinyl, $(C_6-C_{16})$-arylsulfonyl, $(C_7-C_{16})$-aralkylmercapto, $(C_7-C_{16})$-aralkylsulfinyl, $(C_7-C_{16})$-aralkylsulfonyl, sulfamoyl, N-$(C_1-C_{10})$-alkylsulfamoyl, N,N-di-$(C_1-C_{10})$-alkylsulfamoyl, $(C_3-C_8)$-cycloalkylsulfamoyl, N-$(C_6-C_{16})$-arylsulfamoyl, N-$(C_7-C_{16})$-aralkylsulfamoyl, N-$(C_1-C_{10})$-alkyl-N-$(C_6-C_{16})$-arylsulfamoyl, N-$(C_1-C_{10})$-alkyl-N-$(C_7-C_{16})$-aralkylsulfamoyl, $(C_1-C_{10})$-alkylsulfonamido, N-$((C_1-C_{10})$-alkyl)-$(C_1-C_{10})$-alkylsulfonamido, $(C_7-C_{16})$-aralkylsulfonamido and N-$((C_1-C_{10})$-alkyl-$(C_7-C_{16})$-aralkylsulfonamido, radicals which contain an aryl radical are optionally substituted on the aryl by 1 to 5 identical or different radicals selected from the series consisting of hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, and $(C_1-C_8)$-hydroxyalkoxy, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynycarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-arylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkylcarbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-N-$(C_6-C_{12})$-arylcarbamoyloxy, N-$(C_1-C_{10})$-alkyl-N-$(C_7-C_{16})$-aralkylcarbamoyloxy, N-$((C_1-C_{10})$-alkoxy-$(C_1-C_{10})$-alkyl)carbamoyloxy, N-$(C_1-C_{10})$-alkyl-N-$(C_7-C_{16})$-aralkylcarbamoyloxy, N-$((C_1-C_{10})$-alkoxy-$(C_1-C_{10})$-alkyl)carbamoyloxy, N-$((C_6-C_{16})$-aryloxy-$(C_1-C_{10})$-alkyl)carbamoyloxy, N-$((C_7-C_{16})$-aralkyloxy-$(C_1-C_{10})$-alkyl)carbamoyloxy, N-$(C_1-C_{10})$-alkyl-N-$((C_1-C_{10})$-alkoxy-$(C_1-C_{10})$-alkyl)carbamoyloxy, N-$(C_1-C_{10})$-alkyl-N-$((C_6-C_{16})$-aryloxy-$(C_1-C_{10})$-alkyl)carbamoyloxy, N-$(C_1-C_{10})$-alkyl-N-$((C_7-C_{16})$aralkyloxy$(C_1-C_{10})$-alkyl)carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-alkyl-aralkylamino, N-alkyl-arylamino, $(C_1-C_{12})$-alkoxyamino, $(C_1-C_{12})$-alkoxy-N-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino-$(C_1-C_{10})$-alkyl, $(C_1-C_{12})$-alkylmercapto, $(C_1-C_{12})$-alkylsulfinyl, $(C_1-C_{12})$-alkylsulfonyl, $(C_6-C_{16})$-arylmercapto, $(C_6-C_{16})$-arylsulfinyl, $(C_6-C_{16})$-arylsulfonyl, $(C_7-C_{16})$-aralkymercapto, $(C_7-C_{16})$-aralkylsulfinyl and $(C_7-C_{16})$-aralkylsulfonyl, $R^5$ is hydrogen, $(C_1-C_6)$-alkyl or a N-protective group, $C_1-C_8$-alkanoyl, $(C_1-C_6)$-alkylcarbamoyl, $(C_1-C_6)$-alkoxycarbonyl, benzyloxycarbonyl, and $(C_1-C_{10})$-acyloxy-$(C_1-C_6)$-alkyl, a mono-, di-, tri- or tetravalent physiologically acceptable cation selected from the group consisting of sodium, potassium, magnesium, calcium, aluminum or an ammonium ion, optionally mono-, di- or trisubstituted by $(C_1-C_8)$-hydroxyalkyl, $(C_1-C_{C4})$-alkoxy-$(C_1-C_8)$-alkyl, phenyl, benzyl or $(C_1-C_8)$-alkyl, which can be mono-, di- or trisubstituted by hydroxyl or $(C_1-C_4)$-alkoxy, or a cation of a basic amino acid derivative, $R^6$ is a radical of the formula, excluding —$SO_2H$, —Y—[C—U]$_r$—D—W in which Y is —$SO_2$— or —CO—, C is a bond or a branched or unbranched aliphatic $(C_1-C_{16})$-alkanediyl or cycloaliphatic $(C_3-C_{10})$-alkanediyl radical or a branched or unbranched $(C_2-C_{16})$-alkenediyl or cycloalkenediyl radical, or a $(C_2-C_{16})$-alkinediyl radical or a $(C_2-C_{16})$-alkeninediyl radical, each of which can contain one or more C—C multiple bonds, U is a bond or hydrogen or a radical from the following series of heteroatom groupings —CO—, —O(CO)—, —(CO)—O—, —(CO)NR—, —NR(CO)—, —O—, —SO—, —$SO_2$—, and —NR, in which R is $(C_1-C_3)$-alkyl or hydrogen, r is 1, 2, 3 or 4, D is a bond or hydrogen or a branched or unbranched aliphatic $(C_1-C_{10})$-alkanediyl radical, or a branched or unbranched $(C_1-C_{10})$-alkenediylradical, a $(C_2-C_{10})$-alkinediyl radical or a $(C_2-C_{10})$-alkeninediyl radical, each of which can contain one or more C—C multiple bonds, W is a bond or hydrogen or a $(C_3-C_{10})$-cycloaliphatic alkyl, alkenyl, alkynyl or alkenynyl radical or a $(C_6-C_{16})$-aryl radical or a 5- or 6-membered heteroaryl radical, in which at least one of the variable C or D or W is not a bond and U only denotes a heteroatom grouping if C is not a bond or if D and/or W are not a bond and C, D or W, if these are not a bond or hydrogen, are substituted by a combination of up to 5 identical or different substituents selected from the series comprising hydroxyl, halogen, cyano, trifluoromethyl, nitro, carboxyl, $(C_1-C_{12})$-alkyl, $(C_3-C_8)$-cycloalkyl, $(C_6-C_{12})$-aryl, $(C_7-C_{16})$-aralkyl, $(C_3-C_{12})$-alkenyl, $(C_3-C_{12})$-alkynyl, $(C_1-C_{12})$-alkoxy, $(C_1-C_{12})$-alkoxy-$(C_1-C_{12})$-alkyl, $(C_1-C_{12})$-alkoxy-$(C_1-C_{12})$-alkoxy, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, —$OCF_2Cl$, and —$OCF_2$—CHFCl, $(C_1-C_{12})$-alkylcarbonyl, $(C_3-C_8)$-cycloalkylcarbonyl, $(C_6-C_{12})$-arylcarbonyl, $(C_7-C_{16})$-aralkylcarbonyl, cinnamoyl, $(C_3-C_{12})$-alkenylcarbonyl, $(C_3-C_{12})$-alkynylcarbonyl, $(C_1-C_{12})$-alkoxycarbonyl, $(C_1-C_{12})$-alkoxy-$(C_1-C_{12})$-alkoxycarbonyl, $(C_6-C_{12})$-aryloxycarbonyl, $(C_7-C_{16})$-aralkoxycarbonyl, $(C_3-C_8)$-cycloalkoxycarbonyl, $(C_3-C_{12})$-alkenyloxycarbonyl, $(C_3-C_{12})$-alkynyloxycarbonyl, $(C_1-C_{12})$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, $(C_3-C_{12})$-alkenylcarbonyloxy, $(C_3-C_{12})$-alkynylcarbonyloxy, $(C_1-C_{12})$-alkoxycarbonyloxy, $(C_1-C_{12})$-alkoxy-$(C_1-C_{12})$-alkoxycarbonyloxy, $(C_6-C_{12})$-aryloxycarbonyloxy, $(C_7-C_{16})$-aralkyloxycarbonyloxy, $(C_3-C_8)$-cycloalkoxycarbonyloxy, $(C_3-C_{12})$-alkenyloxycarbonyloxy, $(C_3-C_{12})$-alkynyloxycarbonyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbamoyl, N-$(C_1-C_{10})$-alkyl-N-$(C_7-C_{16})$-aralkylcarbamoyl, N-$((C_1-C_{10})$-alkoxy-$(C_1-C_{10})$-alkyl)carbamoyl, N-$((C_6-C_{16})$-aryloxy-$(C_1-C_{10})$-alkyl)carbamoyl, N-$((C_7-C_{16})$-aralkyloxy-$(C_1-C_{10})$-alkyl)carbamoyl, N-$(C_1-C_{10})$-alkyl-N-$((C_1-C_{10})$-alkoxy-$(C_1-C_{10})$-alkyl)carbamoyl, N-$(C_1-C_{10})$-alkyl-N-$((C_6-C_{16})$-aryloxy-$(C_1-C_{10})$-alkyl)carbamoyl, N-$(C_1-C_{10})$-alkyl-N-$((C_7-C_{16})$-aralkyloxy-$(C_1-C_{10})$-alkyl)carbamoyl, carbamoyloxy, N-$(C_1-C_{12})$-alkylcarbamoyloxy, N,N-di-$(C_1-C_{12})$-alkylcarbamoyloxy, N-$(C_3-C_8)$-cycloalkylcarbamoyloxy, N-$(C_6-C_{16})$-arylcarbamoyloxy, N-$(C_7-C_{16})$-aralkylcarbamoyloxy, N-$(C_1-C_{10})$-alkyl-$(C_6-C_{12})$-aryl)carbamoyloxy, N-$(C_1-C_{10})$-alkyl-N-$(C_7-C_{16})$-aralkylcarbamoyloxy, N-$((C_1-C_{10})$-alkoxy-$(C_1-C_{10})$-alkyl))carbamoyloxy, N-$((C_6-C_{16})$-aryloxy-$(C_1-C_{10})$-alkyl)carbamoyloxy, N-$((C_7-C_{16})$-aralkyloxy-$(C_1-C_{10})$-alkyl)carbamoyloxy, N-$(C_1-C_{10})$-alkyl-N-$((C_1-C_{10})$-alkoxy-$(C_1-C_{10})$-alkyl)carbamoyloxy, N-$(C_1-C_{10})$-alkyl-N-$((C_6-C_{16})$-aryloxy-$(C_1-C_{10})$-alkyl)carbamoyloxy, N-$(C_1-C_{10})$-alkyl-N-$((C_7-C_{16})$-aralkyloxy-$(C_1-C_{10})$-alkyl)carbamoyloxy, amino, $(C_1-C_{12})$-alkylamino, di-$(C_1-C_{12})$-alkylamino, $(C_3-C_8)$-cycloalkylamino, $(C_3-C_{12})$-alkenylamino, $(C_3-C_{12})$-alkynylamino, N-$(C_6-C_{12})$-arylamino, N-$(C_7-C_{11})$-aralkylamino, N-$(C_1-C_{10})$-alkyl-$(C_7-C_{10})$-aralkylamino, N-$(C_1-C_{10})$-alkyl-N-$(C_6-C_{12})$-arylamino, $(C_1-C_{12})$-alkoxyamino, $(C_1-C_{12})$-alkoxy-$(C_1-C_{10})$-alkylamino, $(C_1-C_{12})$-alkanoylamino, $(C_3-C_8)$-cycloalkanoylamino, $(C_6-C_{12})$-aroylamino, $(C_7-C_{16})$-aralkanoylamino, $(C_1-C_{12})$-alkanoyl-N-$(C_1-C_{10})$-alkylamino, $(C_3-C_8)$-cycloalkanoyl-N-$(C_1-C_{10})$-alkylamino, $(C_6-C_{12})$-aroyl-N-$(C_1-C_{10})$-alkylamino, $(C_7-C_{11})$-aralkanoyl-N-$(C_1-C_{10})$-alkylamino, $(C_1-C_{12})$-alkanoylamino-$(C_1-C_8)$-alkyl, $(C_3-C_8)$-cycloalkanoylamino-$(C_1-C_8)$-alkyl, $(C_6-C_{16})$-aroylamino-$(C_1-C_8)$-alkyl, $(C_7-C_{16})$-aralkanoylamino-$(C_1-C_8)$-alkyl, amino-$(C_1-C_{10})$-alkyl, N-$(C_1-C_{10})$-alkylamino-$(C_1-C_{10})$-alkyl, N,N-di-$(C_1-C_{10})$-alkylamino-$(C_1-C_{10})$-alkyl, $(C_3-C_8)$-cycloalkylamino- ($C_1$–$C_{10}$)-alkyl, ($C_1$–$C_{12}$)-alkylmercapto, ($C_1$–$C_{12}$)-alkylsulfinyl, ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, sulfamoyl, N-($C_1$–$C_{10}$)-alkylsulfamoyl, N,N-di-($C_1$–$C_{10}$)-alkylsulfamoyl, ($C_3$–$C_8$)-cycloalkylsulfamoyl, N-($C_6$–$C_{16}$)-arylsulfamoyl, N-($C_7$–$C_{16}$)-aralkylsulfamoyl, N-($C_1$–$C_{10}$)-alkyl-N-($C_6$–$C_{16}$)-arylsulfamoyl, N-($C_1$–$C_{10}$)-alkyl-N-($C_7$–$C_{16}$)-aralkylsulfamoyl, ($C_1$–$C_{10}$)-alkylsulfonamido, N-(($C_1$–$C_{10}$)-alkyl)-($C_1$–$C_{10}$)-alkylsulfonamido, ($C_7$–$C_{16}$)-aralkylsulfonamido and N-(($C_1$–$C_{10}$)-alkyl-($C_7$–$C_{16}$)-aralkylsulfonamido,
the radicals which contain an aryl radical substituted on the aryl by 1, 2, 3, 4 or 5 identical or different substituents selected from the series consisting of hydroxyl, halogen, cyano, trifluoromethyl, nitro, carboxyl, ($C_1$–$C_{12}$)-alkyl, ($C_3$–$C_8$)-cycloalkyl, ($C_6$–$C_{12}$)-aryl, ($C_7$–$C_{16}$)-aralkyl, ($C_3$–$C_{12}$)-alkenyl, ($C_3$–$C_{12}$)-alkynyl, ($C_1$–$C_{12}$)-alkoxy, ($C_1$–$C_{12}$)-alkoxy-($C_1$–$C_{12}$)-alkyl, ($C_1$–$C_{12}$)-alkoxy-($C_1$–$C_{12}$)-alkoxy, ($C_6$–$C_{12}$)-aryloxy, ($C_7$–$C_{16}$)-aralkyloxy, ($C_1$–$C_8$)-hydroxyalkyl, —O—$[CH_2]_xC_fH_{(2f+1-g)}F_g$, —$OCF_2Cl$, and —$OCF_2$—$CHFCl$, ($C_1$–$C_{12}$)-alkylcarbonyl, ($C_3$–$C_8$)-cycloalkylcarbonyl, ($C_6$–$C_{12}$)-arylcarbonyl, ($C_7$–$C_{16}$)-aralkylcarbonyl, cinnamoyl, ($C_3$–$C_{12}$)-alkenylcarbonyl, ($C_3$–$C_{12}$)-alkynylcarbonyl, ($C_1$–$C_{12}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl, ($C_3$–$C_8$)-cycloalkoxycarbonyl, ($C_3$–$C_{12}$)-alkenyloxycarbonyl, ($C_3$–$C_{12}$)-alkynyloxycarbonyl, ($C_1$–$C_{12}$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, cinnamoyloxy, ($C_3$–$C_{12}$)-alkenylcarbonyloxy, ($C_3$–$C_{12}$)-alkynylcarbonyloxy, ($C_1$–$C_{12}$)-alkoxycarbonyloxy, ($C_1$–$C_{12}$)-alkoxy-($C_1$–$C_{12}$)-alkoxycarbonyloxy, ($C_6$–$C_{12}$)-aryloxycarbonyloxy, ($C_7$–$C_{16}$)-aralkyloxycarbonyloxy, ($C_3$–$C_8$)-cycloalkoxycarbonyloxy, ($C_3$–$C_{12}$)-alkenyloxycarbonyloxy, ($C_3$–$C_{12}$)-alkynyloxycarbonyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N-($C_6$–$C_{16}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-(($C_1$–$C_{10}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkoxy-($C_1$–$C_{10}$)-alkyl)carbamoyl, N-($C_1$–$C_{10}$)-alkyl-N-(($C_6$–$C_{16}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, carbamoyloxy, N-($C_1$–$C_{12}$)-alkylcarbamoyloxy, N,N-di-($C_1$–$C_{12}$)-alkylcarbamoyloxy, N-($C_3$–$C_8$)-cycloalkylcarbamoyloxy, N-($C_6$–$C_{16}$)-arylcarbamoyloxy, N-($C_7$–$C_{16}$)-aralkylcarbamoyloxy, N-($C_1$–$C_{10}$)-alkyl-N-($C_6$–$C_{12}$)-arylcarbamoyloxy, N-($C_1$–$C_{10}$)-alkyl-N-($C_7$–$C_{16}$)-aralkylcarbamoyloxy, N-(($C_1$–$C_{10}$)-alkoxy-($C_1$–$C_{10}$)-alkyl)carbamoyloxy, N-(($C_6$–$C_{16}$)-aryloxy-($C_1$–$C_{10}$)-alkyl)carbamoyloxy, N-(($C_7$–$C_{16}$)-aralkyloxy-($C_1$–$C_{10}$)-alkyl)carbamoyloxy, N-($C_1$–$C_{10}$)-alkyl-N-(($C_1$–$C_{10}$)-alkoxy-($C_1$–$C_{10}$)-alkyl)carbamoyloxy, N-($C_1$–$C_{10}$)-alkyl-N-(($C_6$–$C_{16}$)-aryloxy-($C_1$–$C_{10}$)-alkyl)carbamoyloxy, N-($C_1$–$C_{10}$)-alkyl-N-(($C_7$–$C_{16}$)-aralkyloxy($C_1$–$C_{10}$)-alkyl)carbamoyloxy, amino, ($C_1$–$C_{12}$)-alkylamino, di-($C_1$–$C_{12}$)-alkylamino, ($C_3$–$C_8$)-cycloalkylamino, ($C_3$–$C_{12}$)-alkenylamino, ($C_3$–$C_{12}$)-alkynylamino, N-($C_6$–$C_{12}$)-arylamino, N-($C_7$–$C_{11}$)-aralkylamino, N-($C_1$–$C_{10}$)-alkyl-N-($C_7$–$C_{16}$)-aralkylamino, N-($C_1$–$C_{10}$)-alkyl-N-($C_6$–$C_{12}$)-arylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_6$–$C_{16}$)-aroylamino-($C_1$–$C_8$)-alkyl, ($C_7$–$C_{16}$)-aralkanoylamino-($C_1$–$C_8$)-alkyl, amino-($C_1$–$C_{10}$)-alkyl, N-($C_1$–$C_{10}$)-alkylamino-($C_1$–$C_{10}$)-alkyl, N,N-di-($C_1$–$C_{10}$)-alkylamino-($C_1$–$C_{10}$)-alkyl, ($C_3$–$C_8$)-cycloalkylamino-($C_1$–$C_{10}$)-alkyl, ($C_1$–$C_{12}$)-alkylmercapto, ($C_1$–$C_{12}$)-alkylsulfinyl, ($C_1$–$C_{12}$)-alkylsulfonyl, ($C_6$–$C_{16}$)-arylmercapto, ($C_6$–$C_{16}$)-arylsulfinyl, ($C_6$–$C_{16}$)-arylsulfonyl, ($C_7$–$C_{16}$)-aralkylmercapto, ($C_7$–$C_{16}$)-aralkylsulfinyl, ($C_7$–$C_{16}$)-aralkylsulfonyl, sulfamoyl, N-($C_1$–$C_{10}$)-alkylsulfamoyl, N,N-di-($C_1$–$C_{10}$)-alkylsulfamoyl, ($C_3$–$C_8$)-cycloalkylsulfamoyl, N-($C_6$–$C_{16}$)-arylsulfamoyl, N-($C_7$–$C_{16}$)-aralkylsulfamoyl, N-($C_1$–$C_{10}$)-alkyl-N-($C_6$–$C_{16}$)-arylsulfamoyl, N-($C_1$–$C_{10}$)-alkyl-N-($C_7$–$C_{16}$)-aralkylsulfamoyl, ($C_1$–$C_{10}$)-alkyl-sulfonamido, N-(($C_1$–$C_{10}$)-alkyl)-($C_1$–$C_{10}$)-alkylsulfonamido, ($C_7$–$C_{16}$)-aralkylsulfonamido and N-(($C_1$–$C_{10}$)-alkyl-($C_7$–$C_{16}$)-aralkylsulfonamido,
and
n is 0 or 1,
f is 1 to 8,
g is 0 or 1 to (2f+1) and
x is 0 to 8, excluding
methyl 5-[((methylsulfonyl)amino)carbonyl]-pyridine-2-carboxylate,
methyl 5-[((2-propylsulfonyl)amino)carbonyl]-pyridine-2-carboxylate,
methyl 5-[((phenylsulfonyl)amino)carbonyl]-pyridine-2-carboxylate,
methyl 5[((benzylsulfonyl)amino)carbonyl]-pyridine-2-carboxylate,
methyl 5-[((4-methoxyphenylsulfonyl)amino)carbonyl]-pyridine-2-carboxylate,
methyl 5-[((1-naphthylsulfonyl)amino)carbonyl]-pyridine-2-carboxylate,
methyl 5-[((4-,5-dibromo-2-thienylsulfonyl)amino)carbonyl]-pyridine-2-carboxylate,
methyl 5-[((5-chloro-2-thienylsulfonyl)amino)carbonyl]-pyridine-2-carboxylate,
methyl 5-[((8-quinolylsulfonyl)amino)carbonyl]-pyridine-2-carboxylate,
methyl 5-[((4-(2-(4,7-dichloroquinolyl)phenylsulfonyl)amino)carbonyl]-pyridine-2-carboxylate.

2. A compound according to claim 1, in which X is —CO—, $R^1$, $R^2$ and $R^3$ are identical or different and are hydrogen ($C_1$–$C_6$)-alkyl, ($C_1$–$C_6$)-alkoxy, fluorine or chlorine, hydroxyl or amino, $R^4$ is a radical of an alcohol $R^4OH$, in which $R^4$ is ($C_1$–$C_{10}$)-acyloxy-($C_1$–$C_6$)-alkyl ($C_1$–$C_{10}$)-alkanoyloxy-($C_1$–$C_6$)-alkyl, benzoyloxy-($C_1$–$C_6$)-alkyl, benzyloxycarbonyloxy-($C_1$–$C_6$)-alkyl or ($C_1$–$C_6$)-alkoxycarbonyloxy-($C_1$–$C_6$)-alkyl, a branched or unbranched aliphatic or cycloaliphatic ($C_3$–$C_{12}$)-alkyl radical, a branched or unbranched cyclic ($C_3$–$C_{12}$)-alkenyl radical, a ($C_2$–$C_{12}$)-alkynyl radical or a ($C_4$–$C_{12}$)-alkenynyl radical, each of which can contain one or more multiple bonds, or a ($C_6$–$C_{16}$)-aryl radical, a ($C_6$–$C_{16}$)-aralkyl radical or a heteroaryl or a heteroaralkyl radical, the above radicals to carry one or two substituents selected from the series consisting of hydroxyl, halogen, cyano, trifluoromethyl, nitro, carboxyl, ($C_1$–$C_{12}$)-alkyl, ($C_3$–$C_8$)-cycloalkyl, ($C_6$–$C_{12}$)-aryl, ($C_7$–$C_{16}$)-aralkyl, ($C_3$–$C_{12}$)-alkenyl, ($C_3$–$C_{12}$)-alkynyl, ($C_1$–$C_{12}$)-alkoxy, ($C_1$–$C_{12}$)-alkoxy-($C_1$–$C_{12}$)-alkyl, ($C_1$–$C_{12}$)-alkoxy-($C_1$–$C_{12}$)-aryloxy, ($C_7$–$C_{16}$)-aralkyloxy, and ($C_1$–$C_8$)-hydroxyalkyl, ($C_1$–$C_{12}$)-alkylcarbonyl, ($C_3$–$C_8$)-cycloalkylcarbonyl, ($C_6$–$C_{12}$)-arylcarbonyl, ($C_7$–$C_{16}$)-aralkylcarbonyl, cinnamoyl, ($C_3$–$C_{12}$)-alkenylcarbonyl, ($C_3$–$C_{12}$)-alkynylcarbonyl, ($C_1$–$C_{12}$)-alkoxycarbonyl, ($C_1$–$C_{12}$)-alkoxy-($C_1$–$C_{12}$)-alkoxycarbonyl, ($C_6$–$C_{12}$)-aryloxycarbonyl, ($C_7$–$C_{16}$)-aralkoxycarbonyl, ($C_3$–$C_8$)-cycloalkoxycarbonyl, ($C_3$–$C_{12}$)-alkenyloxycarbonyl, ($C_3$–$C_{12}$)-alkynyloxycarbonyl, ($C_1$–$C_{12}$)-alkylcarbonyloxy, ($C_3$–$C_8$)-cycloalkylcarbonyloxy, ($C_6$–$C_{12}$)-arylcarbonyloxy, ($C_7$–$C_{16}$)-aralkylcarbonyloxy, cinnamoyloxy, ($C_3$–$C_{12}$)-alkenylcarbonyloxy, ($C_3$–$C_{12}$)-alkynylcarbonyloxy, ($C_1$–$C_{12}$)-alkoxycarbonyloxy, ($C_1$–$C_{12}$)-alkoxy-($C_1$–$C_{12}$)-alkoxycarbonyloxy, ($C_6$–$C_{12}$)-aryloxycarbonyloxy, ($C_7$–$C_{16}$)-aralkyloxycarbonyloxy, ($C_3$–$C_8$)-cycloalkoxycarbonyloxy, ($C_3$–$C_{12}$)-alkenyloxycarbonyloxy, ($C_3$–$C_{12}$)-alkynyloxycarbonyloxy, carbamoyl, N-($C_1$–$C_{12}$)-alkylcarbamoyl, N,N-di-($C_1$–$C_{12}$)-alkylcarbamoyl, N-($C_3$–$C_8$)-cycloalkylcarbamoyl, N-($C_6$–$C_{16}$)-arylcarbamoyl, N-($C_7$–$C_{16}$)-aralkylcarbamoyl, N-($C_1$–$C_{10}$)-alkyl-N-($C_6$–$C_{16}$)-arylcarbamoyl, N-($C_1$–$C_{10}$)-alkyl-N-($C_7$–$C_{16}$)-aralkylcarbamoyl, N-(($C_1$–$C_{10}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkoxy-($C_1$–$C_{10}$)-alkyl)carbamoyl, N-($C_1$–$C_{10}$)-alkyl-N-(($C_6$–$C_{16}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, carbamoyloxy, N-($C_1$–$C_{12}$)-alkylcarbamoyloxy, N,N-di-($C_1$–$C_{12}$)-alkylcarbamoyloxy, N-($C_3$–$C_8$)-cycloalkylcarbamoyloxy, N-($C_6$–$C_{16}$)-arylcarbamoyloxy, N-($C_7$–$C_{16}$)-aralkylcarbamoyloxy, N-($C_1$–$C_{10}$)-alkyl-N-($C_6$–$C_{12}$)-arylcarbamoyloxy, N-($C_1$–$C_{10}$)-alkyl-N-($C_7$–$C_{16}$)-aralkylcarbamoyloxy, N-(($C_1$–$C_{10}$)-alkoxy-($C_1$–$C_{10}$)-alkyl))carbamoyloxy, N-(($C_6$–$C_{16}$)-aryloxy-($C_1$–$C_{10}$)-alkyl)carbamoyloxy, N-(($C_7$–$C_{16}$)-aralkyloxy-($C_1$–$C_{10}$)-alkyl)carbamoyloxy, N-($C_1$–$C_{10}$)-alkyl-N-(($C_1$–$C_{10}$)-alkoxy-($C_1$–$C_{10}$)-alkyl)carbamoyloxy, N-($C_1$–$C_{10}$)-alkyl-N-(($C_6$–$C_{16}$)-aryloxy-($C_1$–$C_{10}$)-alkyl)carbamoyloxy, N-($C_1$–$C_{10}$)-alkyl-N-(($C_7$–$C_{16}$)-aralkyloxy($C_1$–$C_{10}$)-alkyl)carbamoyloxy, amino, ($C_1$–$C_{12}$)-alkylamino, di-($C_1$–$C_{12}$)-alkylamino, ($C_3$–$C_8$)-cycloalkylamino, N-($C_7$–$C_{11}$)-aralkylamino, N-alkylarylamino, ($C_1$–$C_{12}$)-alkoxyamino, ($C_1$–$C_{12}$)-alkoxy-N-($C_1$–$C_{10}$)-alkylamino, ($C_1$–$C_{12}$)-alkanoylamino, ($C_3$–$C_8$)-cycloalkanoylamino, ($C_6$–$C_{12}$)-aroylamino, ($C_7$–$C_{16}$)-aralkanoylamino, ($C_1$–$C_{12}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino and ($C_7$–$C_{11}$)-aralkanoyl-N-($C_1$–$C_{10}$)-alkylamino, and the radicals which contain an aryl radical can be substituted in the aryl part by 1 to 5 identical or different radicals selected from the series consisting of hydroxyl, halogen, cyano, trifluoromethyl, ($C_1$–$C_{12}$)-alkyl, ($C_3$–$C_8$)-cycloalkyl, ($C_1$–$C_{12}$)-alkoxy, ($C_1$–$C_{12}$)-alkoxy-($C_1$–$C_{12}$)-alkoxy, ($C_1$–$C_{12}$)-alkylcarbonyl, ($C_3$–$C_8$)-cycloalkylcarbonyl, ($C_1$–$C_{12}$)-alkoxycarbonyl, ($C_1$–$C_{12}$)-alkoxy-($C_1$–$C_{12}$)-alkoxycarbonyl, ($C_3$–$C_8$)-cycloalkoxycarbonyl, ($C_1$–$C_{12}$)-alkylcarbonyloxy, ($C_3$–$C_8$)-cycloalkylcarbonyloxy, ($C_1$–$C_{12}$)-alkoxycarbonyloxy, ($C_1$–$C_{12}$)-alkoxy-($C_1$–$C_{12}$)-alkoxycarbonyloxy, ($C_3$–$C_8$)-cycloalkoxycarbonyloxy, carbamoyl, N-($C_1$–$C_{12}$)-alkylcarbamoyl N,N-di-($C_1$–$C_{12}$)-alkylcarbamoyl, N-($C_3$–$C_8$)-cycloalkylcarbamoyl, N-(($C_1$–$C_{10}$)-alkoxy-($C_1$–$C_{10}$)-alkyl)carbamoyl, N-($C_1$–$C_{10}$)-alkyl-N-(($C_1$–$C_{10}$)-alkoxy-($C_1$–$C_{10}$)-alkyl)carbamoyl, carbamoyloxy, N-($C_1$–$C_{12}$)-alkylcarbamoyloxy, N,N-di-($C_1$–$C_{12}$)-alkylcarbamoyloxy, N-($C_3$–$C_8$)-cycloalkylcarbamoyloxy, amino, ($C_1$–$C_{12}$)-alkylamino, di-($C_1$–$C_{12}$)-alkylamino, ($C_3$–$C_8$)-cycloalkylamino, ($C_1$–$C_{12}$)-alkanoylamino, ($C_3$–$C_8$)-cycloalkanoylamino, ($C_1$–$C_{12}$)-alkanoylamino-($C_1$–$C_8$)-alkyl, ($C_3$–$C_8$)-cycloalkanoylamino-($C_1$–$C_8$)-alkyl, ($C_1$–$C_{12}$)-alkylmercapto, ($C_1$–$C_{12}$)-alkylsulfinyl and ($C_1$–$C_{12}$)-alkylsulfonyl, $R^5$ is hydrogen, ($C_1$–$C_3$)-alkyl, ($C_1$–$C_4$)-alkanoyl or a mono-, di- or trivalent physiologically acceptable cation selected from sodium, potassium, magnesium, calcium or an ammonium ion, optionally mono-, di- or trisubstituted by ($C_1$–$C_8$)-hydroxyalkyl, ($C_1$–$C_4$)-alkoxy-($C_1$–$C_8$)-alkyl, phenyl, benzyl or ($C_1$–$C_8$)-alkyl, which can be mono-, di-or trisubstituted by hydroxyl and/or ($C_1$–$C_4$)-alkoxy, or a cation of a basic amino acid derivative, $R^6$ is a radical of the formula, excluding —$SO_2$—H, —Y—[C—U]$_r$—D—W in which
Y is —$SO_2$—,
C is a bond or a branched or unbranched aliphatic ($C_1$–$C_{12}$)-alkanediyl radical or a branched or unbranched ($C_2$–$C_{12}$)-alkenediyl radical, a ($C_2$–$C_{12}$)-alkinediyl radical or a ($C_2$–$C_{12}$)-alkeninediyl radical, which can contain one or more C—C multiple bonds,
U is a bond or hydrogen or a radical from the following series of heteroatom groupings —(CO)NR—, —NR(CO)—, —O—, —SO—, or —$SO_2$—, in which R is ($C_2$–$C_3$)-alkyl or hydrogen,
r is 1 or 2,
D is a bond or hydrogen or a branched or unbranched aliphatic ($C_1$–$C_8$)-alkanediyl radical, or a branched or unbranched ($C_2$–$C_8$)-alkenediyl radical, a ($C_2$–$C_8$)-alkinediyl radical and W is a bond or hydrogen or a ($C_3$-$C_{10}$)-cycloaliphatic alkyl, alkenyl, alkynyl or alkenynyl radical or a ($C_6$-$C_{16}$)-aryl radical or a 5- or 6-membered heteroaryl radical, at least one of the variables C or D or W not being a bond and U only being a heteroatom grouping if C is not a bond or if D and/or W are not a bond and C, D or W, if these are not a bond or hydrogen, are substituted by a combination of up to 5 identical or different substituents selected from the series consisting of hydroxyl, halogen, cyano, trifluoromethyl, nitro, carboxyl, ($C_1$-$C_{12}$)-alkyl, ($C_3$-$C_8$)-cycloalkyl, ($C_6$-$C_{12}$)-aryl, ($C_7$-$C_{16}$)-aralkyl, ($C_3$-$C_{12}$)-alkenyl, ($C_3$-$C_{12}$)-alkynyl, ($C_1$-$C_{12}$)-alkoxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_6$-$C_{12}$)-aryloxy, ($C_7$-$C_{16}$)-aralkyloxy, ($C_1$-$C_8$)-hydroxyalkyl, —O—[$CH_2$]$_x$$C_f$H$_{(2f+1-g)}$F$_g$, —OCF$_2$Cl, and —OCF$_2$—CHFCl, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_3$-$C_{12}$)-alkenylcarbonyl, ($C_3$-$C_{12}$)-alkynylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_3$-$C_{12}$)-alkenyloxycarbonyl, ($C_3$-$C_{12}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_3$-$C_{12}$)-alkenylcarbonyloxy, ($C_3$-$C_{12}$)-alkynylcarbonyloxy, carbamoyl, N-($C_1$-$C_{12}$)-alkylcarbamoyl, N,N-di-($C_1$-$C_{12}$)-alkylcarbamoyl, N-($C_3$-$C_8$)-cycloalkylcarbamoyl, N-($C_6$-$C_{16}$)-arylcarbamoyl, N-($C_7$-$C_{16}$)-aralkylcarbamoyl, N-($C_1$-$C_{10}$)-alkyl-N-($C_6$-$C_{16}$)-arylcarbamoyl, N-($C_1$-$C_{10}$)-alkyl-N-($C_7$-$C_{16}$)-aralkylcarbamoyl, N-(($C_1$-$C_{10}$)-alkoxy-($C_1$-$C_{10}$)-alkyl)carbamoyl, N-(($C_6$-$C_{16}$)-aryloxy-($C_1$-$C_{10}$)-alkyl)carbamoyl, N-(($C_7$-$C_{16}$)-aralkyloxy-($C_1$-$C_{10}$)-alkyl)carbamoyl, N-($C_1$-$C_{10}$)-alkyl-N-(($C_1$-$C_{10}$)-alkoxy-($C_1$-$C_{10}$)-alkyl)carbamoyl, N-($C_1$-$C_{10}$)-alkyl-N-(($C_6$-$C_{16}$)-aryloxy-($C_1$-$C_{10}$)-alkyl)carbamoyl, N-($C_1$-$C_{10}$)-alkyl-N-(($C_7$-$C_{16}$)-aralkyloxy-($C_1$-$C_{10}$)-alkyl)-carbamoyl, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N-($C_6$-$C_{12}$)-arylamino, N-($C_7$-$C_{11}$)-aralkylamino, N-($C_1$-$C_5$)-alkyl-($C_7$-$C_{10}$)-aralkylamino, N-($C_1$-$C_5$)-alkyl-N-($C_6$-$C_{12}$)-arylamino, ($C_1$-$C_{12}$)-alkoxyamino, ($C_1$-$C_{12}$)-alkoxy-N-($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N-($C_1$-$C_{10}$)-alkylamino, ($C_3$-$C_8$)-cycloalkanoyl-N-($C_1$-$C_{10}$)-alkylamino, ($C_6$-$C_{12}$)-aroyl-N-($C_1$-$C_{10}$)-alkylamino, ($C_7$-$C_{11}$)-aralkanoyl-N-($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)-alkyl, ($C_6$-$C_{16}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N-($C_1$-$C_{10}$)-alkylamino-($C_1$-$C_{10}$)-alkyl, N,N,-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{16}$)-arylmercapto, ($C_6$-$C_{16}$)-arylsulfinyl, ($C_6$-$C_{16}$)-arylsulfonyl, ($C_7$-$C_{16}$)-aralkylmercapto, ($C_7$-$C_{16}$)-aralkylsulfinyl and ($C_7$-$C_{16}$)-aralkylsulfonyl, the radicals which contain an aryl radical can be substituted on the aryl by 1, 2, 3, 4 or 5 identical or different substituents selected from the series consisting of hydrogen, hydroxyl, halogen, cyano, trifluoromethyl, nitro, carboxyl, ($C_1$-$C_{12}$)-alkyl, ($C_3$-$C_8$)-cycloalkyl, ($C_6$-$C_{12}$)-aryl, ($C_7$-$C_{16}$)-aralkyl, ($C_3$-$C_{12}$)-alkenyl, ($C_3$-$C_{12}$)-alkynyl, ($C_1$-$C_{12}$)-alkoxy, ($C_1$-$C_{12}$)-alkoxy-($C_1$-$C_{12}$)-alkyl, ($C_1$-$C_{12}$)-alkoxy-($C_1$-$C_{12}$)-alkoxy, ($C_6$-$C_{12}$)-aryloxy, ($C_7$-$C_{16}$)-aralkyloxy, ($C_1$-$C_8$)-hydroxyalkyl, —O—[$CH_2$]$_x$$C_f$H$_{(2f+1-g)}$F$_g$, —OCF$_2$Cl, and —OCF$_2$—CHFCl, ($C_1$-$C_{12}$)-alkylcarbonyl, ($C_3$-$C_8$)-cycloalkylcarbonyl, ($C_6$-$C_{12}$)-arylcarbonyl, ($C_7$-$C_{16}$)-aralkylcarbonyl, cinnamoyl, ($C_3$-$C_{12}$)-alkenylcarbonyl, ($C_3$-$C_{12}$)-alkynylcarbonyl, ($C_1$-$C_{12}$)-alkoxycarbonyl, ($C_1$-$C_{12}$)-alkoxy-($C_1$-$C_{12}$)-alkoxycarbonyl, ($C_6$-$C_{12}$)-aryloxycarbonyl, ($C_7$-$C_{16}$)-aralkoxycarbonyl, ($C_3$-$C_8$)-cycloalkoxycarbonyl, ($C_3$-$C_{12}$)-alkenyloxycarbonyl, ($C_3$-$C_{12}$)-alkynyloxycarbonyl, ($C_1$-$C_{12}$)-alkylcarbonyloxy, ($C_3$-$C_8$)-cycloalkylcarbonyloxy, ($C_6$-$C_{12}$)-arylcarbonyloxy, ($C_7$-$C_{16}$)-aralkylcarbonyloxy, cinnamoyloxy, ($C_3$-$C_{12}$)-alkenylcarbonyloxy, ($C_3$-$C_{12}$)-alkynylcarbonyloxy, carbamoyl, N-($C_1$-$C_{12}$)-alkylcarbamoyl, N,N-di-($C_1$-$C_{12}$)-alkylcarbamoyl, N-($C_3$-$C_8$)-cycloalkylcarbamoyl, N-($C_6$-$C_{16}$)-arylcarbamoyl, N-($C_7$-$C_{16}$)-aralkylcarbamoyl, N-($C_1$-$C_{10}$)-alkyl-N-($C_6$-$C_{16}$)-arylcarbamoyl, N-($C_1$-$C_{10}$)-alkyl-N-($C_7$-$C_{16}$)-aralkylcarbamoyl, N-(($C_1$-$C_{10}$)-alkoxy-($C_1$-$C_{10}$)-alkyl)carbamoyl, N-(($C_6$-$C_{16}$)-aryloxy-($C_1$-$C_{10}$)-alkyl)carbamoyl, N-(($C_7$-$C_{16}$)-aralkyloxy-($C_1$-$C_{10}$)-alkyl)carbamoyl, N-($C_1$-$C_{10}$)-alkyl-N-(($C_1$-$C_{10}$)-alkoxy-($C_1$-$C_{10}$)-alkyl)carbamoyl, N-($C_1$-$C_{10}$)-alkyl-N-(($C_6$-$C_{16}$)-aryloxy-($C_1$-$C_{10}$)-alkyl)carbamoyl, N-($C_1$-$C_{10}$)-alkyl-N-(($C_7$-$C_{16}$)-aralkyloxy-($C_1$-$C_{10}$)-alkyl)-carbamoyl, amino, ($C_1$-$C_{12}$)-alkylamino, di-($C_1$-$C_{12}$)-alkylamino, ($C_3$-$C_8$)-cycloalkylamino, ($C_3$-$C_{12}$)-alkenylamino, ($C_3$-$C_{12}$)-alkynylamino, N-($C_6$-$C_{12}$)-arylamino, N-($C_7$-$C_{11}$)-aralkylamino, N-($C_1$-$C_5$)-alkyl-($C_7$-$C_{10}$)-aralkylamino, N-($C_1$-$C_5$)-alkyl-N-($C_6$-$C_{12}$)-arylamino, ($C_1$-$C_{12}$)-alkoxyamino, ($C_1$-$C_{12}$)-alkoxy-N-($C_1$-$C_{10}$)-alkylamino, ($C_1$-$C_{12}$)-alkanoylamino, ($C_3$-$C_8$)-cycloalkanoylamino, ($C_6$-$C_{12}$)-aroylamino, ($C_7$-$C_{16}$)-aralkanoylamino, ($C_1$-$C_{12}$)-alkanoyl-N-($C_1$-$C_{10}$)-alkylamino, ($C_3$-$C_8$)-cycloalkanoyl-N-($C_1$-$C_{10}$)-alkylamino, ($C_6$-$C_{12}$)-aroyl-N-($C_1$-$C_{10}$)-alkylamino, ($C_7$-$C_{11}$)-aralkanoyl-N-($C_1$-$C_{10}$)-alkylamino, ($C_1$-$C_{12}$)-alkanoylamino-($C_1$-$C_8$)-alkyl, ($C_3$-$C_8$)-cycloalkanoylamino-($C_1$-$C_8$)-alkyl, ($C_6$-$C_{16}$)-aroylamino-($C_1$-$C_8$)-alkyl, ($C_7$-$C_{16}$)-aralkanoylamino-($C_1$-$C_8$)-alkyl, amino-($C_1$-$C_{10}$)-alkyl, N-($C_1$-$C_{10}$)-alkylamino-($C_1$-$C_{10}$)-alkyl, N,N,-di-($C_1$-$C_{10}$)-alkylamino-($C_1$-$C_{10}$)-alkyl, ($C_3$-$C_8$)-cycloalkylamino-($C_1$-$C_{10}$)-alkyl, ($C_1$-$C_{12}$)-alkylmercapto, ($C_1$-$C_{12}$)-alkylsulfinyl, ($C_1$-$C_{12}$)-alkylsulfonyl, ($C_6$-$C_{16}$)-arylmercapto, ($C_6$-$C_{16}$)-arylsulfinyl, ($C_6$-$C_{16}$)-arylsulfonyl, ($C_7$-$C_{16}$)-aralkylmercapto, $(C_7-C_{16})$-aralkylsulfinyl and $(C_7-C_{16})$-aralkylsulfonyl,
excluding the compounds:
methyl 5-[((methylsulfonyl)amino)carbonyl]-pyridine-2-carboxylate,
methyl 5-[((2-propylsulfonyl)amino)carbonyl]-pyridine-2-carboxylate,
methyl 5-[((phenylsulfonyl)amino)carbonyl]-pyridine-2-carboxylate,
methyl 5-[((benzylsulfonyl)amino)carbonyl]-pyridine-2-carboxylate,
methyl 5-[((4-methoxyphenylsulfonyl)amino)carbonyl]-pyridine-2-carboxylate,
methyl 5-[((1-naphthylsulfonyl)amino)carbonyl]-pyridine-2-carboxylate,
methyl 5-[((4-, 5-dibromo-2-thienylsulfonyl)amino)carbonyl]-pyridine-2-carboxylate,
methyl 5-[((5-chloro-2-thienylsulfonyl)amino)carbonyl]-pyridine-2-carboxylate,
methyl 5-[((8-quinolysulfonyl)amino)carbonyl]-pyridine-2-carboxylate and
methyl 5-[((4-(2-(4,7-dichloroquinolyl)phenylsulfonyl)amino)carbonyl]-pyridine-2-carboxylate.

3. A compound as claimed in claim 1, in which
X is —CO—,
$R^1$, $R^2$ and $R^3$ are identical or different and are hydrogen, or $(C_1-C_3)$-alkyl, $(C_1-C_3)$-alkoxy, hydroxyl, fluorine or chlorine,
$R^4$ is a radical of an alcohol $R^4OH$, in which $R^4$ is $(C_1-C_{10})$-acyloxy-$(C_1-C_6)$-alkyl $(C_1-C_{10})$-alkanoyloxy-$(C_1-C_6)$-alkyl, benzoyloxy-$(C_1-C_6)$-alkyl, benzyloxycarbonyloxy-$(C_1-C_6)$-alkyl or $(C_1-C_6)$-alkoxycarbonyloxy-$(C_1-C_6)$-alkyl, a branched or unbranched or cyclic aliphatic $(C_3-C_{10})$-alkyl radical, or a branched or unbranched cyclic $(C_3-C_{10})$-alkenyl radical or a $(C_2-C_{12})$-alkynyl radical, each of which can contain one or more C-C multiple bonds, or a $(C_6-C_{16})$-aryl radical, a $(C_7-C_{11})$-aralkyl radical or a heteroaryl or heteroalkyl radical, the above radicals to carry one or two substituents selected from the series consisting of hydroxyl, $(C_1-C_6)$-alkoxy, $(C_1-C_6)$-alkoxy-$(C_1-C_6)$-alkoxy-$(C_6-C_{12})$-aryloxy, and $(C_7-C_{12})$-aralkyloxy, $(C_1-C_8)$-alkylcarbonyl, $(C_3-C_8)$-cycloalkylcarbonyl, $(C_6-C_{12})$-arylcarbonyl, $(C_7-C_{12})$-aralkylcarbonyl, $(C_1-C_8)$-alkoxycarbonyl, $(C_1-C_6)$-alkoxy-$(C_1-C_6)$-alkoxycarbonyl, $(C_6-C_{12})$-aryloxycarbonyl, $(C_7-C_{12})$-aralkoxycarbonyl, $(C_3-C_8)$-cycloalkoxycarbonyl, $(C_1-C_8)$-alkylcarbonyloxy, $(C_3-C_8)$-cycloalkylcarbonyloxy, $(C_6-C_{12})$-arylcarbonyloxy, $(C_7-C_{12})$-aralkylcarbonyloxy, $(C_1-C_8)$-alkoxycarbonyloxy, $(C_1-C_6)$-alkoxy-$(C_1-C_6)$-alkoxycarbonyloxy, $(C_6-C_{12})$-aryloxycarbonyloxy, $(C_7-C_{12})$-aralkyloxycarbonyloxy, $(C_3-C_8)$-cycloalkoxycarbonyloxy, carbamoyl, N-$(C_1-C_8)$-alkylcarbamoyl, N,N-di-$(C_1-C_8)$-alkylcarbamoyl, N-$(C_3-C_8)$-cycloalkylcarbamoyl, N-(($C_1-C_6$)-alxoxy-($C_1-C_{10}$)-alkyl)carbamoyl, amino, $(C_1-C_6)$-alkylamino, di-$(C_1-C_6)$-alkylamino, $(C_3-C_8)$-cycloalkylamino, N-$(C_6-C_{12})$-arylamino, N-$(C_7-C_{11})$-aralkylamino, N-$(C_1-C_5)$-alkyl-$(C_6-C_{12})$-arylamino, $(C_1-C_8)$-alkanoylamino, $(C_3-C_8)$-cycloalkanoylamino, $(C_6-C_{12})$-aroylamino, $(C_7-C_{12})$-aralkanoylamino, $(C_1-C_8)$-alkanoyl-N-$(C_1-C_6)$-alkylamino, $(C_3-C_8)$-cycloalkanoyl-N-$(C_1-C_6)$-alkylamino, $(C_6-C_{12})$-aroyl-N-$(C_1-C_6)$-alkylamino and $C_7-C_{11}$-aralkanoyl-N-$(C_1-C_6)$-alkylamino, the radicals which contain an aryl radical being substituted by up to 3 substituents selected from the series consisting of hydroxyl, fluorine, chlorine, cyano, trifluoromethyl, $(C_1-C_6)$-alkyl, $(C_3-C_8)$-cycloalkyl, and $(C_1-C_8)$-alkoxy, $(C_1-C_6)$-alkylcarbonyl, $(C_3-C_8)$-cycloalkylcarbonyl, $(C_1-C_6)$-alkoxycarbonyl, $(C_3-C_8)$-cycloalkoxycarbonyl, $(C_1-C_6)$-alkylcarbonyloxy, $(C_3-C_8)$-cycloalkylcarbonyloxy, $(C_1-C_6)$alkoxycarbonyloxy, $(C_3-C_8)$cycloalkoxycarbamoyloxy, carbamoyl, N-$(C_1-C_6)$-alkylcarbamoyl, N,N-di-$(C_1-C_6)$-alkylcarbamoyl, N-$(C_3-C_8)$-cycloalkylcarbamoyl, N-(($C_1-C_6$)-alkoxy-$(C_1-C_6)$-alkyl)carbamoyl, N-$(C_1-C_6)$-alkyl-N-(($C_1-C_6$)-alkoxy-$(C_1-C_6)$-alkyl)-carbamoyl, carbamoyloxy, N-$(C_1-C_6)$-alkylcarbamoyloxy, N,N-di-$(C_1-C_6)$-alkylcarbamoyloxy, N-$(C_3-C_8)$-cycloalkylcarbamoyloxy, amino, $(C_1-C_6)$-alkylamino, di-$(C_1-C_6)$-alkylamino, $(C_3-C_8)$-cycloalkylamino, $(C_1-C_6)$-alkanoylamino, $(C_3-C_8)$-cycloalkanoylamino, $(C_1-C_6)$-alkylmercapto, $(C_1-C_6)$-alkylsulfinyl and $(C_1-C_6)$-alkylsulfonyl, and $R^5$ is hydrogen, $(C_1-C_3)$-alkyl, $(C_1-C_4)$-alkanoyl or a mono-, di- or trivalent physiologically acceptable cation selected from the group consisting of sodium, potassium, magnesium, calcium and an ammonium ion, mono-, di- or trisubstituted by $(C_1-C_8)$-hydroxyalkyl, $(C_1-C_4)$-alkoxy-$(C_1-C_8)$-alkyl, phenyl, benzyl or $(C_1-C_8)$-alkyl, which can be mono- di- or trisubstituted by hydroxyl and/or $(C_1-C_4)$-alkoxy, $R^6$ is a radical of the formula, excluding —$SO_2$—H, $$-Y-[C-U]_r-D-W$$

in which
Y is —$SO_2$—,
C is a bond or a $(C_1-C_{16})$-alkanediyl radical
U is a bond or hydrogen or —O—,
r is 1,
D is a bond or hydrogen or an unbranched aliphatic $(C_1-C_8)$-alkanediyl radical, and
W is a bond or hydrogen, a $(C_6-C_{12})$-aryl radical or a 5- or 6-membered heteroaryl radical, at least one of the variables C or D or W not being a bond and U only being a heteroatom grouping if C is not a bond or if D and/or W are not a bond and
C, D or W, if these are not a bond or hydrogen, are substituted in turn by up to 3 identical or different substituents from the series selected from the group consisting of hydroxyl, halogen, cyano, trifluoromethyl, nitro, carboxyl, $(C_1-C_8)$-alkyl, $(C_3-C_8)$-cycloalkyl, $(C_6-C_{12})$-aryl, $(C_7-C_{16})$-aralkyl, $(C_3-C_8)$-alkenyl, $(C_3-C_8)$-alkynyl, $(C_1-C_8)$-alkoxy, $(C_1-C_8)$-alkoxy-$(C_1-C_8)$-alkyl, $(C_6-C_{12})$-aryloxy, $(C_7-C_{16})$-aralkyloxy, $(C_1-C_8)$-hydroxyalkyl, —O—$[CH_2]_xC_fH_{(2f+1-g)}F_g$, $(C_1-C_8)$-alkoxycarbonyl, $(C_6-C_{12})$-aryloxycarbonyl, $(C_7-C_{14})$-aralkoxycarbonyl, $(C_3-C_8)$-cycloalkoxycarbonyl, $(C_1-C_8)$-alkylcarbonyloxy, $(C_3-C_8)$-cycloalkylcarbonyloxy, $(C_6-C_{12})$-arylcarbonyloxy, $(C_7-C_{16})$-aralkylcarbonyloxy, cinnamoyloxy, carbamoyl, N-$(C_1-C_{12})$-alkylcarbamoyl, N,N-di-$(C_1-C_{12})$-alkylcarbamoyl, N-$(C_3-C_8)$-cycloalkylcarbamoyl, N-$(C_6-C_{16})$-arylcarbamoyl, N-$(C_7-C_{16})$-aralkylcarbamoyl, N-$(C_1-C_{10})$-alkyl-N-$(C_6-C_{16})$-arylcarbmoyl, N-$(C_1-C_{10})$-alkyl-N-

($C_7$–$C_{16}$)-aralkylcarbamoyl, N-(($C_1$–$C_{10}$)-alkoxy-($C_1$–$C_{10}$)-alkyl)carbamoyl, N-(($C_6$–$C_{16}$)-aryloxy-($C_1$–$C_{10}$)-alkyl)carbamoyl, N-(($C_7$–$C_{16}$)-aralkyloxy-($C_1$–$C_{10}$)-alkyl)carbamoyl, N-($C_1$–$C_{10}$)-alkyl-N-(($C_1$–$C_{10}$)-alkyl)carbamoyl, N-($C_1$–$C_{10}$)-alkyl-N-(($C_6$–$C_{16}$)-aryloxy-($C_1$–$C_{10}$)-alkyl)carbamoyl, N-($C_1$–$C_{10}$)-alkyl-N-(($C_7$–$C_{16}$)-aralkyloxy-($C_1$–$C_{10}$)-alkyl)carbamoyl, amino, ($C_1$–$C_8$)-alkylamino, di-($C_1$–$C_8$)-alkylamino, ($C_3$–$C_8$)-cycloalkylamino, N-($C_6$–$C_{12}$)-arylamino, N-($C_7$–$C_{11}$)-aralkylamino, N-($C_1$–$C_3$)-alkyl-N-($C_7$–$C_{11}$)-aralkylamino, ($C_1$–$C_{10}$)-alkanoylamino-($C_3$–$C_8$)-cycloalkanoylamino-($C_6$–$C_{12}$)-aroylamino-, ($C_7$–$C_{16}$)-aralkanoylamino-($C_1$–$C_{10}$)-alkanoyl-N-($C_1$–$C_{10}$)-alkylamino, ($C_3$–$C_8$)-cycloalkanoyl-N-($C_1$–$C_{10}$)-alkylamino, ($C_6$–$C_{12}$)-aroyl-N-($C_1$–$C_{10}$)-alkylamino, ($C_7$–$C_{11}$)-aralkanoyl-N-($C_1$–$C_{10}$)-alkylamino, ($C_1$–$C_{12}$)-alkanoylamino-($C_1$–$C_6$)-alkyl, ($C_3$–$C_8$)-cycloalkanoylamino-($C_1$–$C_8$)-alkyl, ($C_6$–$C_{16}$)-aroylamino-($C_1$–$C_6$)-alkyl, ($C_7$–$C_{16}$)-aralkanoylamino-($C_1$–$C_6$)-alkyl, ($C_1$–$C_8$)-alkylmercapto, ($C_1$–$C_8$)-alkylsulfinyl, ($C_1$–$C_8$)-alkylsulfonyl, ($C_6$–$C_{12}$)-arylmercapto, ($C_6$–$C_{12}$)-arylsulfinyl, ($C_6$–$C_{12}$)-arylsulfonyl, ($C_7$–$C_{14}$)-aralkylmercapto, ($C_7$–$C_{14}$)-aralkylsulfinyl and ($C_7$–$C_{14}$)-aralkylsulfonyl, the radicals which contain an aryl radical can be substituted on the aryl by 1, 2, 3, 4 or 5 identical or different substituents selected from the series consisting of hydrogen, hydroxyl, halogen, cyano, trifluoromethyl, nitro, carboxyl, ($C_1$–$C_8$)-alkyl, ($C_3$–$C_8$)-cycloalkyl, ($C_6$–$C_{12}$)-aryl, ($C_7$–$C_{16}$)-aralkyl, ($C_3$–$C_{12}$)-alkenyl, ($C_3$–$C_{12}$)-alkynyl, ($C_1$–$C_8$)-alkoxy, ($C_1$–$C_6$)-alkoxy-($C_1$–$C_6$)-alkyl, ($C_6$–$C_{12}$)-aryloxy, $C_7$–$C_{16}$-aralkyloxy, and —O—[$CH_2$]$_x$$C_fH_{(2f+1-g)}F_g$, ($C_1$–$C_{12}$)-alkoxycarbonyl, ($C_3$–$C_8$)-cycloalkoxycarbonyl, ($C_1$–$C_{12}$)-alkylcarbonyloxy, ($C_3$–$C_8$)-cycloalkylcarbonyloxy, carbamoyl, N-($C_1$–$C_8$)-alkylcarbamoyl, N,N-di-($C_1$–$C_8$)-alkylcarbamoyl, N-($C_3$–$C_8$)-cycloalkylcarbamoyl, N-($C_6$–$C_{16}$)-arylcarbamoyl, N-($C_7$–$C_{16}$)-aralkylcarbamoyl, N-($C_1$–$C_8$)-alkyl-N-($C_6$–$C_{16}$)-arylcarbamoyl, N-($C_1$–$C_8$)-alkyl-N-($C_7$–$C_6$)-aralkylcarbamoyl, N-(($C_1$–$C_6$)-alkoxy-($C_1$–$C_6$)-alkyl)carbamoyl, N-(($C_6$–$C_6$)-aryloxy-($C_1$–$C_6$)-alkyl)carbamoyl, N-(($C_7$–$C_{16}$)-aralkyloxy-($C_1$–$C_6$)-alkyl)carbamoyl, N-($C_1$–$C_8$)-alkyl-N-(($C_1$–$C_6$)-alkoxy-($C_1$–$C_6$)-alkyl)carbamoyl, N-($C_1$–$C_8$)-alkyl-N-(($C_6$–$C_{16}$)-aryloxy-($C_1$–$C_6$)-alkyl)carbamoyl, N-($C_1$–$C_8$)-alkyl-N-(($C_7$–$C_{16}$)-aralkyloxy-($C_1$–$C_6$)-alkyl)carbamoyl, amino, ($C_1$–$C_6$)-alkylamino, di-($C_1$–$C_6$)-alkylamino, ($C_3$–$C_8$)-cycloalkylamino, N-($C_6$–$C_{12}$)-arylamino, N-($C_7$–$C_{11}$)-aralkylamino, N-($C_1$–$C_3$)-alkyl-($C_7$–$C_{11}$)-aralkylamino, N-($C_1$–$C_3$)-alkyl-($C_6$–$C_{12}$)-arylamino, ($C_1$–$C_8$)-alkoxyamino, ($C_1$–$C_8$)-alkanoylamino-($C_3$–$C_8$)-cycloalkanoylamino-($C_6$–$C_{12}$)-aroylamino-, ($C_7$–$C_{12}$)-aralkanoylamino-($C_1$–$C_8$)-alkanoyl-N-($C_1$–$C_6$)-alkylamino, ($C_3$–$C_8$)-cycloalkanoyl- N-($C_1$–$C_6$)-alkylamino, ($C_6$–$C_{12}$)-aroyl-N-($C_1$–$C_{10}$)-alkylamino-($C_7$–$C_{11}$)-aralkanoyl-N-($C_1$–$C_6$)-alkylamino, ($C_1$–$C_8$)-alkanoylamino-($C_1$–$C_4$)-alkyl, ($C_3$–$C_8$)-cycloalkanoylamino-($C_1$–$C_4$)-alkyl, ($C_6$–$C_{12}$)-aroylamino- ($C_1$–$C_4$)-alkyl and ($C_7$–$C_{12}$)-aralkanoylamino-($C_1$–$C_4$)-alkyl, excluding the compounds:

methyl 5-[((methylsulfonyl)amino)carbonyl]-pyridine-2-carboxylate, methyl 5-[((2-propylsulfonyl)amino)carbonyl]-pyridine-2-carboxylate, methyl 5-[((phenylsulfonyl)amino)carbonyl]-pyridine-2-carboxylate, methyl 5-[((benzylsulfonyl)amino)carbonyl]-pyridine-2-carboxylate, methyl 5-[((4-methoxyphenylsulfonyl)amino)carbonyl]-pyridine-2-carboxylate, methyl 5-[((1-naphthylsulfonyl)amino)carbonyl]-pyridine-2-carboxylate, methyl 5-[((4-,5-dibromo-2-thienylsulfonyl)amino)carbonyl]-pyridine-2-carboxylate, methyl 5-[((5-chloro-2-thienylsulfonyl)amino)carbonyl]-pyridine-2-carboxylate, methyl 5-[((8-quinolysulfonyl)amino)carbonyl]-pyridine-2-carboxylate, methyl 5-[((4-(2-(4,7-dichloroquinolyl)phenylsulfonyl)amino)carbonyl]-pyridine-2-carboxylate.

4. A compound according to claim 1, in which
X is —CO—, $R^1$, $R^2$ and $R^3$ are hydrogen, $R^4$ is the radical of an alcohol $R^4OH$ and is a branched or unbranched or cyclic aliphatic ($C_3$–$C_9$)-alkyl radical, or a branched or unbranched cyclic ($C_3$–$C_8$)-alkenyl radical or ($C_2$–$C_8$)-alkynyl radical, or a phenyl, benzyl, phenethyl or phenylpropyl radical, the above radicals containing a substituent selected from the series consisting of hydrogen, hydroxyl, ($C_1$–$C_4$)-alkoxy, ($C_1$–$C_6$)-alkoxycarbonyl, ($C_6$–$C_{12}$)-phenoxycarbonyl, ($C_7$–$C_{16}$)-phenylalkylcarbonyl, ($C_3$–$C_8$)-cycloalkoxycarbonyl, ($C_1$–$C_6$)-alkycarbonyloxy, ($C_3$–$C_8$)-cycloalkylcarbonyloxy, benzoyloxy, ($C_7$–$C_{16}$)-phenylalkylcarbonyloxy and ($C_3$–$C_8$)-cycloalkoxycarbonyloxy, or ($C_1$–$C_6$)-alkoxycarbonyloxy, phenoxycarbonyloxy, ($C_7$–$C_{16}$)-phenylalkylcarbonyloxy or ($C_3$–$C_8$)-cycloalkoxycarbonyloxy, $R^5$ is hydrogen or a mono-, di- or trivalent physiologically acceptable cation selected from sodium, potassium, magnesium, calcium and $H_3N^{\oplus}C(CH_2)OH)_3$ (tris salt), $R^6$ is a radical of the formula, excluding —$SO_2H$, —Y—[C—U]$_r$—D—W in which
Y is —$SO_2$—, C is a bond or ($C_1$–$C_4$)-alkanediyl, U is bond, hydrogen or —O—, r is 1, D is a bond, hydrogen or ($C_1$–$C_4$)-alkanediyl, W is a bond, hydrogen or a phenyl radical, at least one of the variables C or D or W not being a bond and U only being a heteroatom grouping if C is not a bond or if D and/or W are not a bond, and C, D or W are substituted by hydrogen or by 1 or 2 substituents from the following series fluorine, chlorine, ($C_1$–$C_6$)-alkyl, phenyl, ($C_1$–$C_6$)-alkoxy, phenoxy, —O—[$CH_2$]$_x$$C_fH_{(2f+1-g)}F_g$, carbamoyl, N-($C_1$–$C_{10}$)-alkylcarbamoyl, N,N-di(C$_1$–$C_8$)-alkylcarbamoyl, N-($C_3$–$C_8$)-cycloalkylcarbamoyl, N-phenylcarbamoyl, N-($C_7$–$C_{16}$)-phenylalkylcarbamoyl, N-($C_1$–$C_8$)-alkyl-N-($C_6$–$C_{16}$)-phenylcarbamoyl, N-($C_1$–$C_8$)-alkyl-N-($C_7$–$C_{16}$)-phenylalkylcarbamoyl, N-(($C_1$–$C_4$)- alkoxy-$(C_1-C_8)$-alkyl)carbamoyl, N-phenoxy-$(C_1-C_8)$-alkyl)carbamoyl, N-$((C_7-C_{16})$-phenylalkyloxy-$(C_1-C_8)$-alkyl)carbamoyl, N-$(C_1-C_8)$-alkyl-N-$((C_1-C_6)$-alkoxy-$(C_1-C_8)$-alkyl)carbamoyl, N-$(C_1-C_8)$-alkyl-N-$((C_6-C_{12})$-phenoxy-$(C_1-C_8)$-alkyl)carbamoyl, N-$(C_1-C_8)$-alkyl-N-$((C_7-C_{16})$-phenylalkyloxy-$(C_1-C_8)$-alkyl)carbamoyl, $(C_1-C_8)$-alkanoylamino, $(C_3-C_8)$-cycloalkanoylamino, $(C_6-C_{12})$-phenylamino, $(C_7-C_{11})$-phenylalkanoylamino, $(C_1-C_8)$-alkanoyl-N-$(C_1C_{10})$-alkylamino, $(C_3-C_8)$-cycloalkanoyl-N-$(C_1-C_6)$-alkylamino, benzoyl-N-$(C_1-C_{10})$-alkylamino, $(C_7-C_{11})$-phenylalkanoyl-N-$(C_1-C_6)$-alkylamino, $(C_1-C_{10})$-alkanoylamino-$(C_1-C_2)$-alkyl, $(C_3-C_8)$-cycloalkanoylamino-$(C_1-C_2)$-alkyl, benzoylamino-$(C_1-C_2)$-alkyl and $(C_7-C_{14})$-phenylalkanoylamino-$(C_1-C_2)$-alkyl, the radicals which contain an aryl radical substituted by a substituent from the series consisting of hydrogen, hydroxyl, fluorine, chlorine, trifluoromethyl, $(C_1-C_6)$-alkyl and $(C_1-C_8)$-alkoxy, n is 0,
f is 1 to 5,
g is 0 or 1 to (2f+1) and
x is 0 or 1,
excluding the compounds:
methyl 5-[((methylsulfonyl)amino)carbonyl]-pyridine-2-carboxylate,
methyl 5-[((2-propylsulfonyl)amino)carbonyl]-pyridine-2-carboxylate,
methyl 5-[((phenylsulfonyl)amino)carbonyl]-pyridine-2-carboxylate,
methyl 5-[((benzylsulfonyl)amino)carbonyl]-pyridine-2-carboxylate,
methyl 5-[((4-methoxyphenylsulfonyl)amino)carbonyl]-pyridine-2-carboxylate,
methyl 5-[((1-naphthylsulfonyl)amino)carbonyl]-pyridine-2-carboxylate,
methyl 5-[((4-,5-dibromo-2-thienylsulfonyl)amino)carbonyl]-pyridine-2-carboxylate,
methyl 5-[((5-chloro-2-thienylsulfonyl)amino)carbonyl]-pyridine-2-carboxylate,
methyl 5-[((8-quinolysulfonyl)amino)carbonyl]-pyridine-2-carboxylate,
methyl 5-[((4-(2-(4,7-dichloroquinolyl)phenylsulfonyl)amino)carbonyl]-pyridine-2-carboxylate.

5. A method of suppressing fibroses in mammals comprising administering to a mammal requiring fibroses suppression, a fibroses suppressing effective amount of a compound or a pharmaceutically acceptable acid addition salt thereof according to claim 1.

6. A fibroses suppressing composition comprising a carrier and as the active ingredient, a fibroses suppressing effective amount of a compound or a pharmaceutically acceptable acid addition salt thereof according to claim 1.

* * * * *